US007368556B2

(12) United States Patent
Nassif et al.

(10) Patent No.: US 7,368,556 B2
(45) Date of Patent: *May 6, 2008

(54) **DNA AND PROTEINS OR PEPTIDES SPECIFIC OF BACTERIA OF THE *NEISSERIA MENINGITIDIS* SPECIES, METHODS FOR OBTAINING THEM AND BIOLOGICAL APPLICATIONS THEREOF**

(75) Inventors: Xavier Nassif, Paris (FR); Colin Tinsley, Paris (FR)

(73) Assignee: Institut National de la Sante et de la Recherche Medicale (INSERM), Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 11/638,574

(22) Filed: Dec. 14, 2006

(65) Prior Publication Data
US 2007/0105225 A1    May 10, 2007

Related U.S. Application Data

(60) Division of application No. 11/045,208, filed on Jan. 31, 2005, which is a division of application No. 09/928,457, filed on Aug. 14, 2001, now Pat. No. 7,029,845, which is a continuation of application No. 09/214,759, filed as application No. PCT/FR97/01295 on Jul. 11, 1997, now abandoned.

(30) Foreign Application Priority Data
Jul. 12, 1996  (FR)  ................................. 96 08768

(51) Int. Cl.
*C12Q 1/68*  (2006.01)
(52) U.S. Cl. ............... 536/23.7; 536/24.32; 536/24.33; 435/6; 435/183; 435/252.3; 435/320.1; 435/69.3; 514/44

(58) Field of Classification Search ..................... None
See application file for complete search history.

(56) References Cited

U.S. PATENT DOCUMENTS 5,445,933 A    8/1995  Eadie et al.

(Continued)

FOREIGN PATENT DOCUMENTS

EP    0 301 992    2/1989

(Continued)

OTHER PUBLICATIONS

Zhou et al, "Sequence diversity within the argF, fbp and recA genes of natural isolates of *Neisseria meningitidis*: interspecies recombination within the argF gene", Mol Microbiol. Aug. 1992, 6 (15), pp. 2135-2146, England.

(Continued)

*Primary Examiner*—Mark Navarro
*Assistant Examiner*—Ginny Allen Portner
(74) *Attorney, Agent, or Firm*—Nixon & Vanderhye P.C.

(57) ABSTRACT

The DNA of the invention are characterised in that they concern the whole or part of genes, with their reading frame, to be found in *Neisseria meningitidis*, but not in *Neisseria gonorrhoeae*, or in *Neisseria lactamica* except the genes involved in the biosynthesis of the polysaccharide capsule, frp A, frp C, opc, por A, rotamase the sequence IC1106, IgA protease, pilline, pilC, transferrin binding proteins and opacity proteins. The invention also concerns the polypeptides corresponding to these DNA and the antibodies directed against these polypeptides. It is applicable in the prevention and the detection of meningococcus induced infections and meningitis.

22 Claims, 9 Drawing Sheets

U.S. PATENT DOCUMENTS

Figure 2:
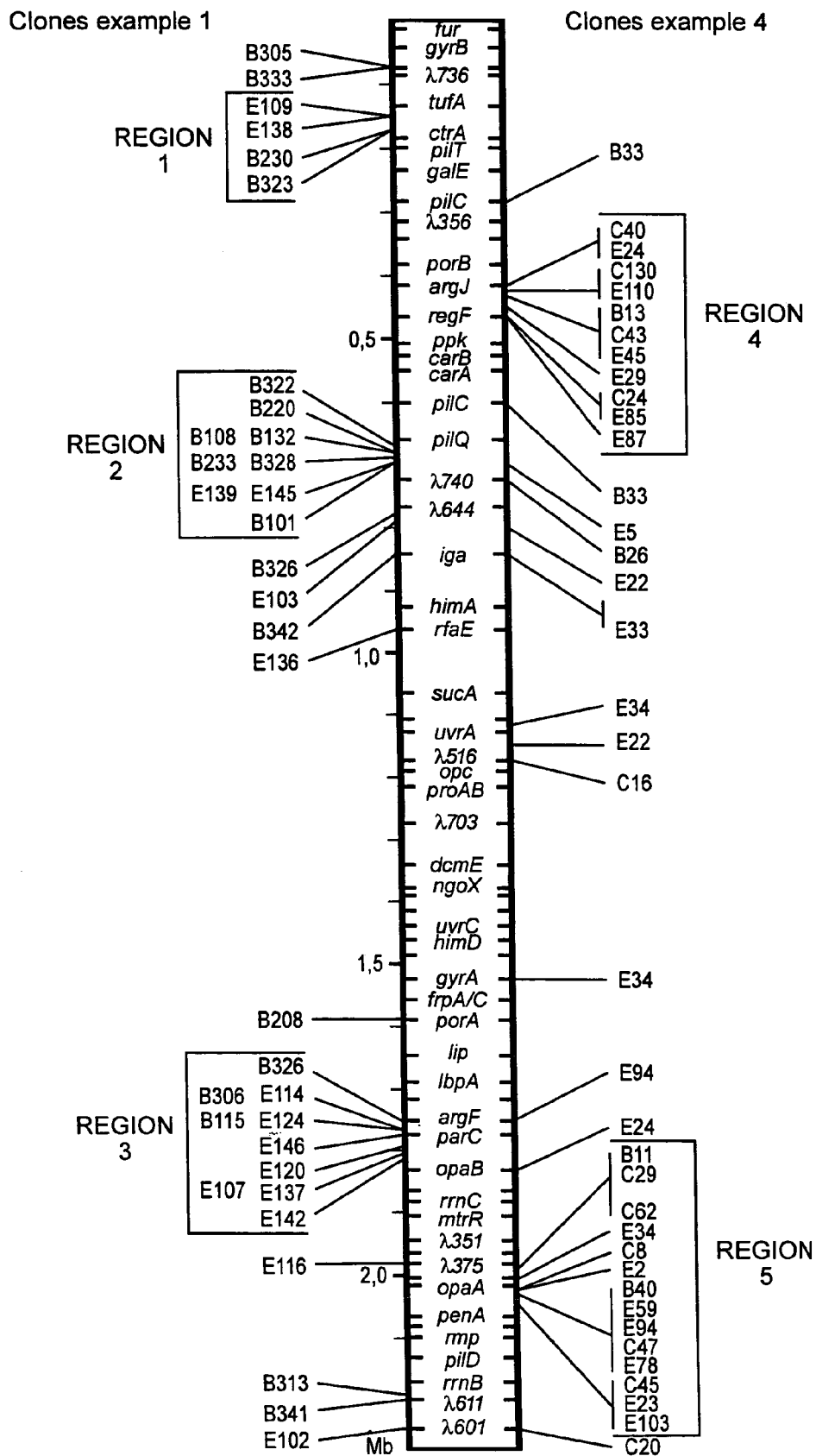

| | | | |
|---|---|---|---|
| 5,523,217 | A | 6/1996 | Lupski et al. |
| 5,747,252 | A | 5/1998 | Yang et al. |
| 6,835,384 | B1 * | 12/2004 | Aujame et al. .......... 424/250.1 |
| 7,026,157 | B1 * | 4/2006 | Stojiljkovic et al. ..... 435/252.3 |
| 7,029,845 | B2 * | 4/2006 | Nassif et al. .................. 435/6 |

FOREIGN PATENT DOCUMENTS

| | | |
|---|---|---|
| EP | 0 337 896 | 10/1989 |
| EP | 0 452 596 | 10/1991 |
| EP | 548012 A | 6/1993 |
| WO | WO 88/03957 | 6/1988 |
| WO | WO 90/15621 | 12/1990 |
| WO | WO 94/05703 | 3/1994 |
| WO | 9407356 A | 4/1994 |

OTHER PUBLICATIONS

Devi et al, "Antibodies to poly[(2—8)-alpha-N-acetylneuraminic acid] and poly[(2—9)-alpha-N-acetylneuraminic acid] are elicited by immunization of mice with *Escherichia coli* K92 conjugates: potential vaccines for groups B and C meningococci and *E. coli* K1.", Proc Natl Acad Sci USA, Aug. 15, 1991, 88 (16, pp. 1715-1719.

Wolff et al, "Identification and characterization of specific sequences encoding pathogenicity associated proteins in the genome of commensal *Neisseria* species", FEMS Microbiol Lett, Jan. 15, 1995, 125 (2-3), pp. 255-263, Netherlands.

Petering et al, "Genes associated with meningococcal capsule complex are also found in *Neisseria gonorrhoeae*", J BACTERIOL, Jun. 1996, 178 (11) pp. 3342-3345, United States.

Frosch et al, "Evidence for a common molecular origin of the capsule gene loci in gram-negative bacteria expressing group II capsular polysaccharides", Mol Microbiol, May 1991, 5 (5), pp. 1251-1263, England.

Frosch et al, "Phospholipid substitution of capsular polysaccharides and mechanisms of capsule formation in *Neisseria meningitidis*", Mol Microbiol, May 1993, 8 (3), pp. 483-493, England.

Frosch et al, "Conserved outer-membrane protein of *Neisseria-meningitides* involved in capsule expression" Infection and Immunity, 1992, 60, pp. 798-803.

Strathdee et al, "Identification of Epidemiologic markers for *Neisseria-meningitidis* using difference analysis", GENE, 1995, 166, pp. 105-110.

Lauerman et al, "Avian mycoplasma identification using polymerase chain reaction amplicon and restriction fragment length polymorphism analysis", Avian Dis, Oct.-Dec. 1995, 39, (4) pp. 804-811 . United States.

Weiss, E et al, The Immune system and infectious diseases, 1975, vol. 4, pp. 423-440 (abstract).

Moore, TD et al, Infection Immunity, vol. 63(4), pp. 1603-1607 Apr. 1995 (abstract).

Bautsch, W, FEMS Microbiology Lett., Mar. 1, 1993, vol. 107 (2-3), pp. 191-197.

Versalovic, J et al, Methods in Molecular and Cellular Biology, vol. 5(2), pp. 96-104, 1995.

Dempsey, Jo Ann Fanney et al, Journal of Bacteriology, Nov. 1995, vol. 177(22), pp. 6390-6400.

Wolff, K. et al, FEMS microbiology leters, Jan. 15, 1995, vol. 125(2-3), pp. 255-263.

Martin, P.R. et al, accession No. M65216, created date in EMBL May 2, 1992.

Gaher, M. et al, Molecular Microbiology, Jan. 1996, vol. 19(2), pp. 249-259.

Dempsey, Jo Ann F. et al, Journal of Bacteriology, Apr. 1994, vol. 176(7).

Serizawa, H. et al, Nucleic Acids Research, vol. 15(3), pp. 1153-1163, 1987.

Welcher, Andrew A. et al, Nucleic Acids Research, vol. 14(24), pp. 10027-10044, Dec. 22, 1986.

Gaher, Martin et al, Molecular Microbiology, vol. 19(2), pp. 249-259, 1996.

Swanson, J. et al, Infection and Immunity, vol. 10(3), pp. 633-644, Sep. 1974.

Knight et al., "Identification and Characterization of a Novel Insertion Sequence, IS 1106, Downstream of the porA Gene in B15 *Neisseria meningitidis*", Molecular Microbiology (1992) 6(11), pp. 1565-1573.

Dempsey, J. et al, Journal of Bacteriology, vol. 177, No. 22, Nov. 1995, pp. 6390-6400 (Nov. 1995).

Virji, M. et al, Molecular Microbiology, vol. 6(19), Oct. 1992, pp. 2785-2795 (abstract).

Virji, M. et al, Molecular Microbiology, Vo. 10(3), pp. 499-510, Nov. 1993 (abstract).

Frosch et al., "Phospholipid Substitution of Capsular Polysaccharides and Mechanisms of Capsule Formation in *Neisseria meningitidis*", Molecular Microbiology (1993)8(3), pp. 483-493.

Schutte et al., "Isolation of YAC Insert Sequences by Representational Difference Analysis", Nucleic Acids Research, 1995, vol. 23, No. 20, pp. 4127-4133.

Lisitsyn et al., "Cloning the Differences Between Two Complex Genomes", Science, vol. 259, Feb. 12, 1993, pp. 946-951.

Tinsley et al., "Analysis of the Genetic Difference between *Neisseria meningitidis* and *Neisseria gonorrhoeae*: Two closely related Bacteria Expressing two Different Pathogenicities", Proc. Natl. Acad, Sci., USA, vol. 93, pp. 11109-11114, Oct. 1996 Microbiology.

* cited by examiner

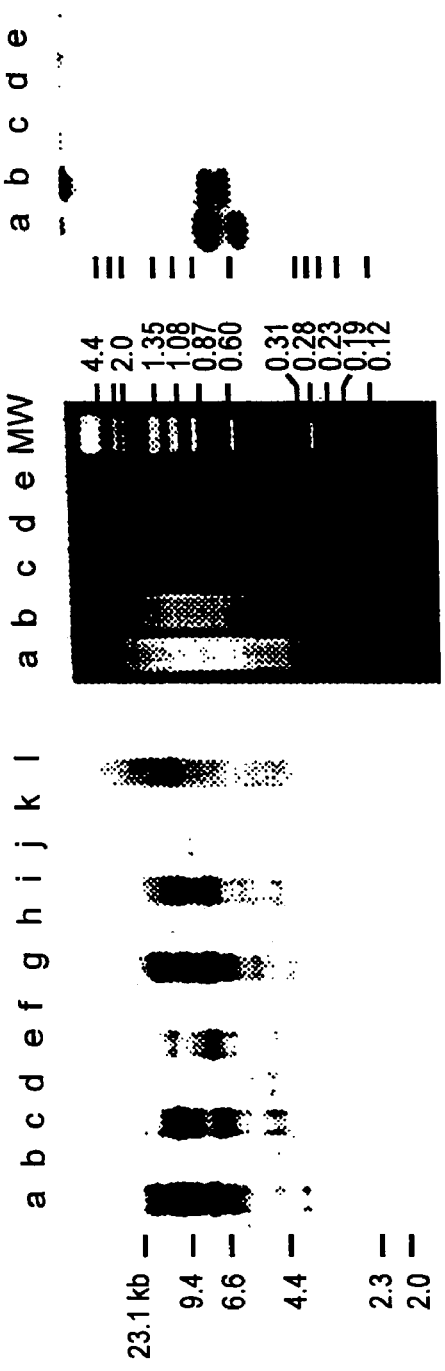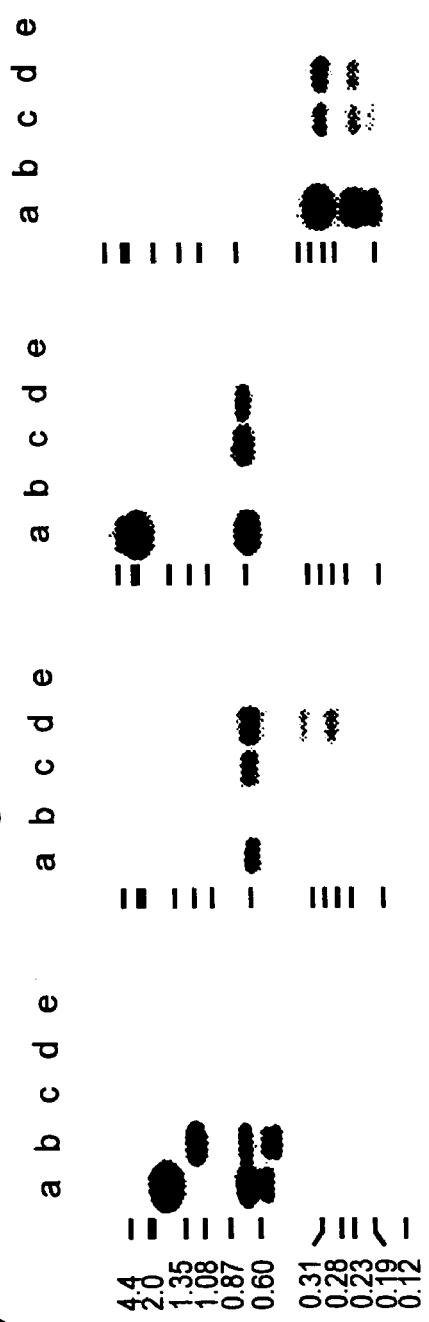

1 2 3 4 5 6 7 8 9 10 11 12
Nm Nl Nm Nl Nm Ng Nm Ng Nm Ng Nc Nm 1 2 3 4 5 6 7 8 9 10 11 12
Nm Nl Nm Nl Nm Ng Nm Ng Nm Ng Nc Nm

DNA AND PROTEINS OR PEPTIDES SPECIFIC OF BACTERIA OF THE *NEISSERIA MENINGITIDIS* SPECIES, METHODS FOR OBTAINING THEM AND BIOLOGICAL APPLICATIONS THEREOF

The present application is a divisional of U.S. application Ser. No. 11/045,208, filed Jan. 31, 2005 (pending), which is a divisional of U.S. application Ser. No. 09/928,457, filed Aug. 14, 2001 (U.S. Pat. No. 7,029,845), which is a continuation of application Ser. No. 09/214,759, filed Apr. 22, 1999 (abandoned), which is a 371 application of PCT/FR97/01295, filed Jul. 11, 1997, and claims benefit of FR 96 08768, filed Jul. 12, 1996, the entire contents of each of which is hereby incorporated by reference.

The invention relates to DNAs and to proteins and peptides which are specific to bacteria of the species *Neisseria meningitidis* (abbreviated below to Nm), to the process for obtaining them and to their biological uses, in particular for the prevention and detection of meningococcal infections and meningitis.

It is known that Nm is one of the main agents of cerebrospinal meningitis.

Studies conducted in the United States have shown that 5 to 10% of the population are asymptomatic carriers of the Nm strain(s). The transmission factors of Nm are poorly known. For a proportion of persons infected, Nm penetrates the bloodstream, where it can cause meningococcaemia and/or progress to the cerebrospinal stream, to cause meningitis. Without fast antibiotic treatment, the infection can develop like lightning and become fatal.

Compared with other pathogens, Nm has the characteristic of being able to cross the haemato-encephalic barrier to colonize the meninges. The study of the pathogenicity of Nm is therefore important not only in the context of meningitis, but also in the context of any disease which affects the brain.

The benefit of having available tools specific to this species of bacteria for the uses envisaged above is therefore understood.

Genetically, Nm is very close to bacteria of the species *Neisseria gonorrhoeae* (abbreviated to Ng below) and of the species *Neisseria lactamica* (abbreviated to Nl below). However, their pathogenicity is very different.

Nm colonizes the nasopharynx, and then crosses the pharyngeal epithelium to invade the submucous space, thus being responsible for septicaemia and meningitis.

Ng is especially responsible for infections located in the genitourinary tract. It colonizes the genital mucosa, and then crosses the epithelium, subsequently invading the subepithelium, where it multiplies and is responsible for a severe inflammatory reaction. Disseminated gonococcal infections are possible, but remain rare and are the result of only some strains.

As regards Nl, it is considered that this is a non-pathogenic strain, since it is not responsible for a localized or general invasion.

A first consideration thus led to taking into account the fact that Nm and Ng, while being bacteria very close to one another, have different pathogenic potencies.

Since the genome of these bacteria has a high homology, only limited parts of the genome of Nm and Ng must code for specific virulence factors responsible for their pathogenesis.

It is clear that Nm has, compared with Ng, DNA sequences which are specific to it and which must be involved in the expression of its specific pathogenic potency.

The species Nm is subdivided into serogroups based on the nature of the capsular polysaccharides.

At least 13 serogroups have been defined, among which serogroups A, B and C are responsible for about 90% of meningitis cases. Groups A and C are found in epidemic forms of the disease. Group B is the serogroup generally isolated the most in Europe and the United States.

The capsule, which is present in Nm and absent from Ng, has served as the basis for formulating meningococcal antimeningitis vaccines.

The polysaccharides of the Nm capsule have been used to formulate a vaccine which has proved to be effective in preventing in adults the meningitis caused by meningococci of serogroups A, C, W135 and Y.

However, the polysaccharide of Nm group C has proved to be weakly immunogenic in children of less than two years, while the polysaccharide of Nm group B is non-immunogenic in man and shares epitopes with adhesion glycoproteins present in human neuronal cells.

There is therefore no universal vaccine capable of preventing infections caused by all the serogroups of the meningococci and capable of responding to the intrinsic antigenic variability of bacterial pathogens in general and Nm in particular.

Because of the cross-reactivity of the Nm group B polysaccharide with human antigens, the multiplicity of the serogroups and the antigenic variability of Nm, the strategies proposed to date cannot lead to a vaccine which is effective in all situations.

Research is therefore concentrated on study of the characteristic elements responsible for the specificity of the meningococcal pathogenesis.

The majority of genes which have been studied in either of the two bacteria Nm or Ng have their homologue in the second bacterium.

In the same way, the majority of virulence factors identified to date in Nm have a counterpart in Ng, that is to say pilin, the PilC proteins, the opacity proteins and the receptors of lactoferrin and transferrin.

The specific attributes of meningococci characterized in the prior art are the capsule, the Frp proteins analogous to RTX toxins, Opc proteins of the external member, glutathione peroxidase, the porin PorA and the rotamase gene.

Among these, only the capsule is invariably present in the virulent strains of Nm. However, several extracellular pathogens have a capsule without nevertheless crossing the haemato-encephalic barrier.

Attributes which have not yet been identified must therefore be responsible for the specificity of the meningococcal pathogenesis. These attributes are probably coded by DNA sequences present among the meningococci but absent from the gonococci.

The inventors have developed a new approach based on subtractive isolation of Nm-specific genes, which genes must be linked to the specific pathogenesis of Nm, and more particularly to crossing of the haemato-encephalic barrier.

The subtractive method developed in the prior art has resulted in the production of epidemiological [sic] markers for some Nm isolates. These markers are of limited use: they do not cover all the serogroups of the Nm species.

In contrast to these studies, the work of the inventors has led, by confronting Nm with the entire Ng chromosome sheared in a random manner, to the development of a means for cloning all the DNAs present in Nm and absent from Ng, thus providing tools of high specificity with respect to Nm, and thus enabling the genetic variability of the species to be responded to for the first time.

The terms "present" and "absent" used in the description and claims in relation to the DNAs of a strain or their expression products are interpreted on the basis of identical hybridization conditions (16 h at 65° C., with NaPO$_4$ 0.5 M, pH 7.2; EDTA-Na 0.001 M, 1%, 1% bovine serum albumin and 7% sodium dodecylsulphate) using the same probe and the same labelling intensity of the probe, the same amount of chromosomal DNA and the same comparison element (chromosomal DNA of the homologous strain). It is therefore considered that the DNA is present if the signal obtained with the probe is practically the same as that obtained with the reference strain.

Conversely, it is considered that the DNA is absent if this signal appears very weak.

A second consideration of the pathogenicities of Nm and Ng leads to taking into account their common capacity for colonization and penetration of the mucosa, and then invasion of the subepithelial space of the latter. It is highly probable that this process involves virulence factors common to the two pathogens. In this respect, it is known that a certain number of virulence factors have already been identified in Nm and in Ng, such as the pili proteins, PilC, the opacity proteins, the IgA proteases, the proteins for binding to transferrin and to lactoferrin, and the lipooligosaccharides.

The approach of the inventors is thus extended to investigation of the Nm regions which are specific to Nm and Ng but absent from the non-pathogenic species Nl, and in a general manner to investigation of the chromosomal regions of the DNAs and their expression products specific to a given species by the means developed in accordance with the invention.

The object of the invention is thus to provide DNAs of Nm specific to its pathogenic potency and means for obtaining them, in particular by formulating banks formed exclusively from these Nm-specific DNAs.

It also provides the products derived from these DNA sequences.

The invention also relates to the utilization of specific and exhaustive characteristics of these banks to formulate tools which can be used, in particular, in diagnostics, treatment and prevention.

The DNAs of the invention are characterized in that they are in all or part genes, with their reading frame, present in *Neisseria meningitidis*, but absent either from *Neisseria gonorrhoeae* and from *Neisseria lactamica*, with the exception of genes involved in the biosynthesis of the polysaccharide capsule, frpA, frpC, opc, por A, rotamase, the sequence IS1106 (Accession No. Z 11857 in the EMBL/GenBank/DDBJ Nucleotide Sequence Data Libraries; see Knight et al., 1992, Molecular Microbiology 6(11): 1565-1573), IgA proteases, pilin, pilC, proteins which bind transferrin and opacity proteins.

As stated above, the terms "present" and "absent" are interpreted on the basis of the hybridization conditions used in the Southern blotting described in the examples and referred to above.

It can be seen that these DNAs include variants where these express a function intrinsic to the Nm species, more particularly a phenotype found solely in Nm or in common exclusively with Ng.

According to a main aspect, these DNAs are specific to the pathogenicity of *Neisseria meningitidis*, in spite of the genetic variability of this species.

According to an embodiment of the invention, the said DNAs are specific to Nm, in contrast to Ng.

More particularly, the Nm-specific DNAs are absent from *Neisseria lactamica* and from *Neisseria cinerea.*

Surprisingly, the majority of genetic differences between the strains of meningococci and those of gonococci appear grouped in distinct regions, which are said to correspond to the pathogenicity islets described previously for *E. coli* and *Y. pestis.*

In a preferred embodiment of the invention, these DNA are thus also characterized in that they comprise one or more sequence(s) present on the chromosome of *Neisseria meningitidis* Z2491 between tufA and pilT, or region 1 of the chromosome, and/or the sequence(s) capable of hybridizing with the above sequence(s), with the proviso of being specific to *Neisseria meningitidis.*

"Specific" in the description and the claims means the nucleotide sequences which hybridize only with those of Nm under the hybridization conditions given in the examples and referred to above.

In this respect, it can be seen that, in a general manner, when "all or part" of a sequence is referred to in the description and claims, this expression must be interpreted with respect to the specificity defined above.

Furthermore, all or part of a peptide or a fragment of a peptide or an antibody means a product having the biological properties respectively of the natural peptide or the antibody formed against the peptide.

Genes of the *Neisseria meningitidis* capsule are grouped in region 1.

DNAs of this type have a sequence corresponding in all or part to SEQ ID No. 9, 13, 22 or 30, and/or to any sequence located at more or less 20 kb from these SEQ ID on the chromosome of an Nm strain, and/or have a sequence which is capable of hybridizing with at least a fragment of any one of these sequences.

In another preferred embodiment of the invention, these DNA are also characterized in that they are made up of one or more sequence(s) present on the chromosome of *Neisseria meningitidis* Z2491 between pilQ and λ740, or region 2 of the chromosome, and/or the sequences(s) capable of hybridizing with the above sequence(s), with the proviso of being specific to *Neisseria meningitidis.*

DNAs according to this embodiment have a sequence corresponding in all or part to SEQ ID No. 1, 2, 4, 6, 7, 10, 15, 31 or 34, and/or to any sequence located at more or less 20 kb from these SEQ ID on the chromosome of an Nm strain, and/or have a sequence which is capable of hybridizing with at least a fragment of any one of these sequences.

The invention especially provides all or part of the DNA sequence SEQ ID No. 36 of 15,620 bp, and the sequences corresponding to the open reading frames SEQ ID No. 37, SEQ ID No. 38, SEQ ID No. 39, SEQ ID No. 40, SEQ ID No. 41, SEQ ID No. 42, SEQ ID No. 43, SEQ ID No. 44 and SEQ ID No. 45.

In yet another preferred embodiment of the invention, these DNAs are also characterized in that they are made up of one or more sequence(s) present on the chromosome of *Neisseria meningitidis* Z2491 between argF and opaB, or region 3 of the chromosome, and/or the sequence(s) capable of hybridizing with the above sequence(s), with the proviso of being specific to *Neisseria meningitidis.*

DNAs according to this embodiment are characterized in that they have a sequence corresponding in all or part to SEQ ID No. 8, 21, 23, 25, 26, 28, 29, 32 or 35, and/or to any sequence located at more or less 20 kb from these SEQ ID on the chromosome of an Nm strain, and/or have a sequence which is capable of hybridizing with at least a fragment of any one of these sequences.

Regions 1, 2 and 3 identified above have a high proportion of sequences specific to *Neisseria meningitidis* and also fall within the context of the invention.

Other DNAs representative of the specificity with respect to *Neisseria meningitidis* have one or more sequences which is/are present on the chromosome of *Neisseria meningitidis* Z2491 but are not part of regions 1, 2 and 3 defined above.

Such DNAs comprise one or more sequence(s) corresponding in all or part to SEQ ID No. 3, 5, 11, 12, 14, 16, 18, 19, 20, 24, 27 or 33, and/or to any sequence located at more or less 20 kb from these SEQ ID on the chromosome of an Nm strain, and/or have a sequence capable of hybridizing with such sequences.

Taking into account the uses envisaged in particular, the invention more specifically relates to the above DNAs involved in the pathogenesis of the bacterial organism.

In particular, it provides the DNAs corresponding to at least one of the characterizations given above and coding for a protein exported beyond the cytoplasmic membrane, and/or of which all or part of their sequence corresponds to the conserved region of the said DNAs.

According to another embodiment of the invention, the DNAs are thus common with those of Ng, but are absent from those of Nl.

These are more specifically the DNAs which are present on region 4 (arg J to reg F) or on region 5 (lambda 375 marker to pen A) on the chromosome of Nm Z2491 and/or are capable of hybridizing with the said DNAs present, with the proviso of being specific to Nm and Ng, in contrast to Nl.

"Specific to Nm and Ng in contrast to Nl" means the DNAs which hybridize with the DNAs of Nm and Ng under the hybridization conditions of the examples (see example 4 in particular).

The DNAs of regions 4 and 5 and those capable of hybridizing with these DNAs, with the proviso of expressing the intrinsic functions of Nm, have the advantage of intervening in a significant manner in the virulence of Nm, being involved in the stage of initial colonization and penetration and in the septicaemic dissemination.

According to other embodiments, the invention provides transfer and expression vectors, such as plasmids, cosmids or bacteriophages, comprising at least one DNA as defined above.

It also provides host cells transformed by at least one DNA as defined above.

Other host cells of the invention comprise genes or gene fragments specific to Nm, and are characterized in that their chromosome is deleted by at least one DNA according to the invention, in particular a DNA responsible for the pathogenicity. They are more specifically bacterial cells, in particular of Nm.

The invention also relates to the RNAs of which the sequence corresponds in all or part to the transcription of at least one DNA sequence or sequence fragment as defined above.

The invention also relates to the antisense nucleic acids of the DNAs as defined above, or of fragments of these DNAs.

These antisense nucleic acids carry, where appropriate, at least one substituent, such as a methyl group and/or a glycosyl group.

Other products which fall within the context of the invention include polypeptides.

These polypeptides are characterized in that they have an amino acid chain corresponding to all or part of a sequence coded by the nucleic acids defined above, or deduced from sequences of these nucleic acids.

They are advantageously polypeptides corresponding to all or part of the polypeptides exported beyond the cytoplasmic membrane, more specifically polypeptides corresponding to all or part of those coded by a conserved region.

As a variant, the polypeptides of the invention can be modified with respect to those corresponding to the nucleic acid sequences such that they are particularly suitable for a given use, in particular use as a vaccine.

Modification is understood as meaning any alteration, deletion or chemical substitution where this does not affect the biochemical properties of the corresponding natural polypeptides, more specifically of functional proteins exported at the periplasm and the external membrane.

Other products according to the invention include antibodies directed against the above polypeptides.

The invention thus provides polyclonal antibodies, and also monoclonal antibodies, characterized in that they recognize at least one epitope of a polypeptide as described above.

It also relates to fragments of these antibodies, more particularly the fragments Fv, Fab and Fab'2.

The invention also relates to the anti-antibodies which are capable of recognizing the antibodies defined above, or their fragments, by a reaction of the antigen-antibody type.

According to the invention, the various products considered above are obtained by a synthesis and/or biological route in accordance with conventional techniques.

The nucleic acids can also be obtained from banks made up of Nm-specific DNAs such as are formulated by a subtractive technique, this technique comprising:

mixing of two DNA populations,
realization of at least one subtractive hybridization-amplification iteration, and
collection of the desired DNA or DNAs, followed, where appropriate, by its/their purification with elimination of redundant sequences.

According to the invention, the two DNA populations originate respectively from a strain of *Neisseria meningitidis*, the so-called reference strain for which the specific bank must be constructed, and a strain of *Neisseria*, the so-called subtraction strain, having a homology in primary DNA sequences of greater than about 70% with the *Neisseria meningitidis* strain, the DNA sequences of the subtraction and reference strains being obtained respectively by random shearing, and by cleavage by a restriction endonuclease capable of producing fragments less than about 1 kb in size.

The invention provides in particular a process for obtaining *Neisseria meningitidis*-specific DNA banks, comprising the stages of random shearing of the chromosomal DNA of a strain of *Neisseria gonorrhoeae*, the so-called subtraction strain, in particular by repeated passage through a syringe,
cleavage of the chromosomal DNA of a strain of *Neisseria meningitidis*, the so-called reference strain, preferably by a restriction enzyme producing fragments less than about 1 kb in size,
splicing of the DNA fragments of the reference strain, cleaved by the restriction enzyme, with suitable oligonucleotide primers,
realization of a subtractive hybridization-amplification iteration, by:
mixing of the two DNA populations under suitable conditions for hybridization of homologous sequences, and then
amplification of auto-reannealed fragments and collection of these fragments, digestion of these fragments by a restriction enzyme and re-splicing with oligonucleotide primers, followed by a purification of the spliced DNA and, where appropriate, a new iteration of the subtractive hybridization, comprising mixing of DNA fragments of *Neisseria gonorrhoeae* sheared as indicated above with DNA fragments of *Neisseria meningitidis* produced by the preceding iteration, followed, if desired, by cloning of the DNAs of the bank.

The primers used are oligodeoxynucleotide primers which are suitable for the restriction endonuclease used and allow insertion into a cloning site, such as the EcoRI site of the plasmid pBluescript. Such primers will advantageously be chosen among the oligodeoxynucleotides referred to in the sequence listing under SEQ ID no. 36 to 45.

The banks thus obtained are formed from DNAs which are specific to meningococci and absent from gonococci.

The specificity of the DNAs was verified, as described in the examples, at each iteration by Southern blots, with genes common to the subtraction strain and to the reference strain, or with the total DNA of each of the strains digested by a restriction endonuclease, such as ClaI.

At each iteration, the exhaustivity of the DNA bank was also verified by Southern blotting with probes known to be specific to the reference strain, that is to say for *Neisseria meningitidis* the frp, opc and rotamase genes in particular.

The experiments carried out showed that the banks obtained by the process of the invention are deficient in genes having a significant homology with species of *Neisseria* other than *Neisseria meningitidis*, for example the ppk or pilC1 genes, generally in only 2 or 3 iterations.

If necessary, two routes, which are not exclusive of each other, can be taken.

It is possible to proceed with an $(n+1)^{th}$ iteration using the DNA of iteration n as the DNA population of the reference strain.

As a variant, a second bank independent of the first is constructed, with a restriction enzyme of different specificity to that used in the first bank, for example MboI.

In all cases, it is preferable to keep each of the products produced by each of the iterations performed.

The invention also provides the use of the subtractive technique described above to obtain banks of the DNAs common to Nm and Ng, but specific with respect to Nl.

Three different banks are advantageously constructed, two of them by digestion of the chromosomal DNA of Nm by MboI and Tsp5091, and the third by digestion of the chromosomal DNA of Nm with MspI. Two subtraction series allow the DNAs having the required specificity to be collected, as described in the examples.

The invention also relates to the process for obtaining these banks and the banks themselves.

It can be seen that, generally, the process of the invention can be used to obtain banks of DNAs specific to a given cell species, or to a given variant of the same species, where another species or another variant which is close genomically and expresses different pathogenic potencies exists.

Using the process of the invention, DNA banks specific to given species of cryptococci, *Haemophilus*, pneumococci or also *Escherichia coli*, or more generally any bacterial agent belonging to the same species and having different pathovars will advantageously be constructed.

Furthermore, from these banks the invention provides the means to have available virulence factors specific to a species or a given variant.

Such banks are therefore tools which are of great interest for having available attributes which are responsible for the specificity of a pathogen, this use being more specifically illustrated according to the invention by the obtaining of banks comprising the attributes responsible for the specificity of the meningococcal pathogenesis.

Study of the products of the invention, the nucleic acids, polypeptides and antibodies, has enabled an absolute specificity with respect to *Neisseria meningitidis*, regardless of the strain and its variability, to be demonstrated.

These products are therefore particularly suitable for diagnosis or prevention of infections and meningitis caused by *Neisseria meningitidis*, whether in adults or children and regardless of the serogroups of the strain in question.

The method for diagnosis, according to the invention, of a meningococcal infection, and more particularly of meningococcal meningitis, by demonstration of the presence of *Neisseria meningitis* in an analytical sample is characterized by the stages of:

- bringing into contact a sample to be analysed, that is to say a biological sample or a cell culture, and a reagent formulated from at least one nucleic acid as defined above, if appropriate in the form of a nucleotide probe or a primer, or, as a variant, from at least one antibody or a fragment of an antibody as defined above, under conditions which allow, respectively, hybridization or a reaction of the antigen-antibody type, and
- detection of any reaction product formed.

If the reagent is formulated from a nucleic acid, this can be in the form of a nucleotide probe in which the nucleic acid or a fragment of the latter is labelled in order to enable it to be detected. Suitable markers include radioactive, fluorescent, enzymatic or luminescent markers.

As a variant, the nucleic acid is included in a host cell, which is used as the reagent.

In these various forms, the nucleic acid is used as such or in the form of a composition with inert vehicles.

If the reagent is compiled from an antibody, or a fragment of an antibody, this can be labelled for detection purposes. Most generally, a fluorescent, enzymatic, radioactive or luminescent marker is used.

The antibody or the antibody fragment used, which is labelled if appropriate, can be used as such or in the form of a composition with inert vehicles.

The sample used in the stage of bringing the components into contact is a biological sample produced by a mammal, such as cephalorachidian fluid, urine, blood or saliva.

The detection stage is carried out under conditions which allow the reaction product to be demonstrated when it is formed. Conventional means use fluorescence, luminescence, colour or radioactive reactions, or also autoriadography [sic] techniques. It is also possible to quantify the product.

The invention also relates to the labelled products, the nucleic acids and antibodies, as new products.

The method defined above can be used for diagnosis of an immune reaction specific to a meningococcal infection.

The reagent used is thus a polypeptide according to the invention, as coded by the said nucleic acid sequences, corresponding to the natural product or a polypeptide which is modified but has the biological and immunological activity of the corresponding natural polypeptide.

It is advantageously a polypeptide exported beyond the cytoplasmic membrane of *Neisseria meningitidis*, more particularly the part of such a polypeptide corresponding to the conserved region of the DNA.

The invention also relates to kits for carrying out the methods defined above. These kits are characterized in that they comprise:

at least one reagent as defined above, that is to say of the nucleic acid, antibody or polypeptide type, products, in particular markers or buffers, which enable the intended nucleotide hybridization reaction or immunological reaction to be carried out, as well as use instructions.

The specificity of the products of the invention and their location on the chromosome of *Neisseria meningitidis* Z2491, either grouped in a region and able to be interpreted as pathogenicity islets, or isolated on the chromosome, impart to them a very particular interest for realization of vaccine compositions with a universal purpose, that is to say whatever the strain and the variability which it expresses. These compositions can include in their spectrum other prophylaxes, and can be, for example, combined with childhood vaccines.

The invention thus provides vaccine compositions which include in their spectrum antimeningococcal prophylaxis, intended for prevention of any infection which may be caused by *Neisseria meningitidis*, these compositions being characterized in that they comprise, in combination with (a) physiologically acceptable vehicle(s), an effective amount of polypeptides or anti-antibodies or their fragments as defined above, these products optionally being conjugated, in order to reinforce their immogenicity [sic].

Immunogenic molecules which can be used comprise the poliovirus protein, the tetanus toxin, or also the protein produced by the hypervariable region of a pilin.

As a variant, the vaccine compositions according to the invention are characterized in that they comprise, in combination with (a) physiologically acceptable vehicle(s), an effective amount:

of nucleic acids as defined above, of transformed host cells as defined above, or of Nm cells, the chromosome of which has been deleted by at least one DNA sequence according to the invention involved in the pathogenicity of the bacterium. The nucleotide material used is advantageously placed under the control of a promoter of its expression in vivo and synthesis of the corresponding protein. To reinforce the immunogenicity, it is also possible to combine this nucleic material with a DNA or an RNA which codes for a carrier molecule, such as the poliovirus protein, tetanus toxin or a protein produced by the hypervariable region of a pilin.

The vaccine compositions of the inventions can be administered parenterally, subcutaneously, intramuscularly or also in the form of a spray.

Other characteristics and advantages of the invention are given in the examples which follow for illustration thereof, but without limiting its scope.

Figure 9:
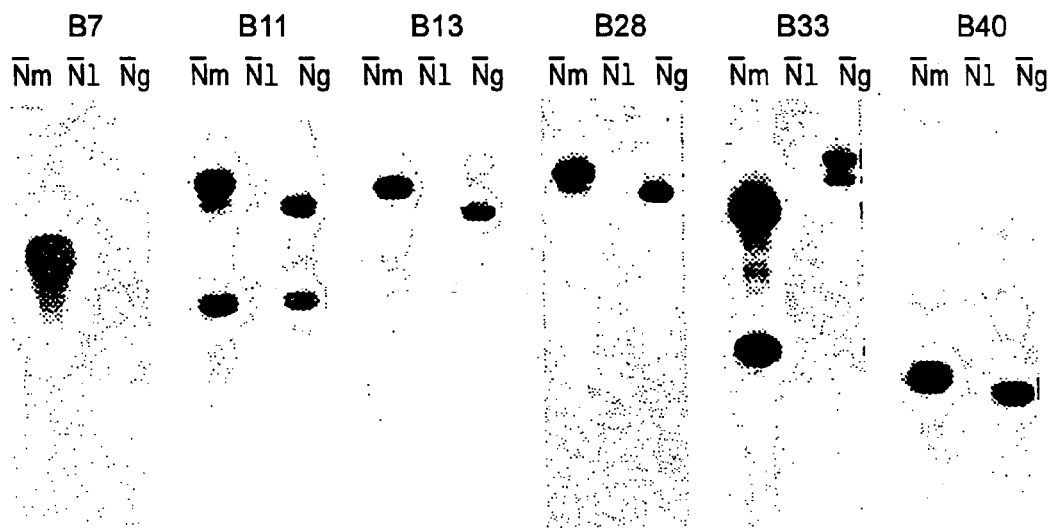
Figure 10:
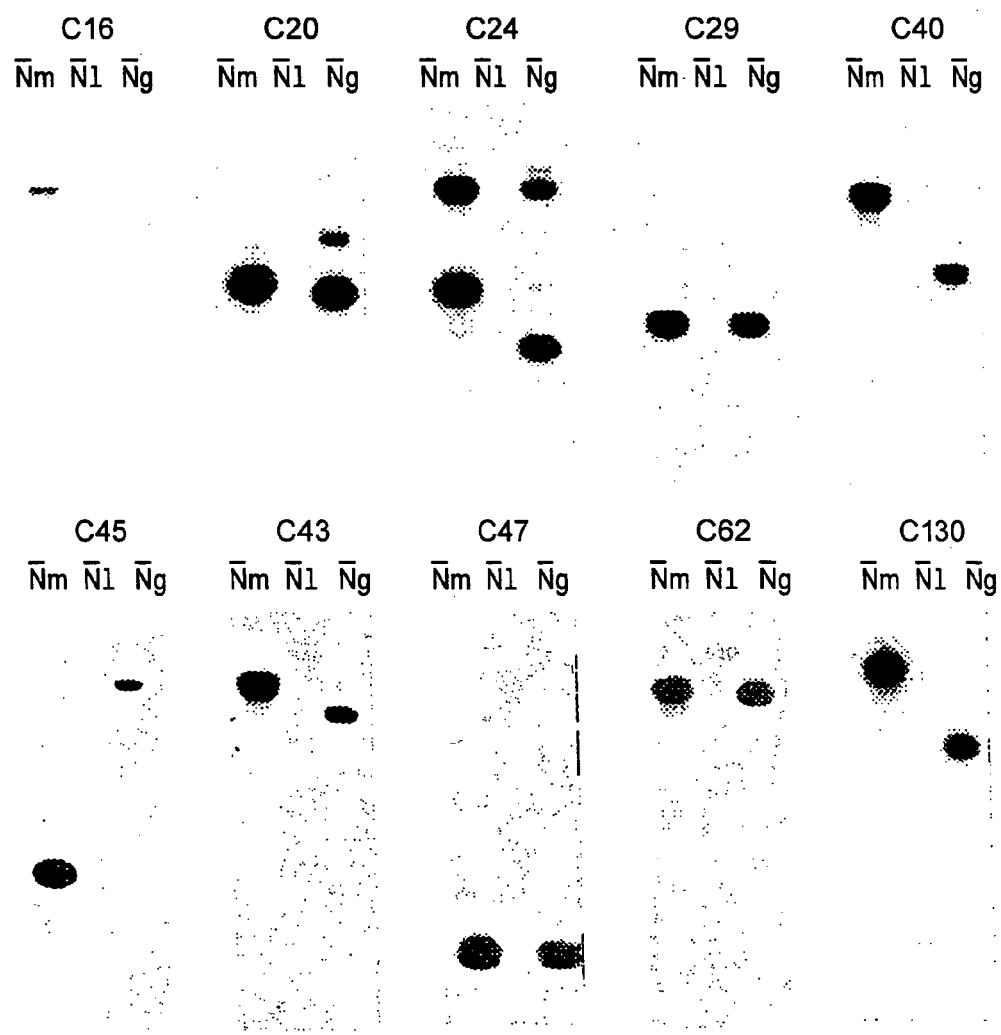
Figure 11:
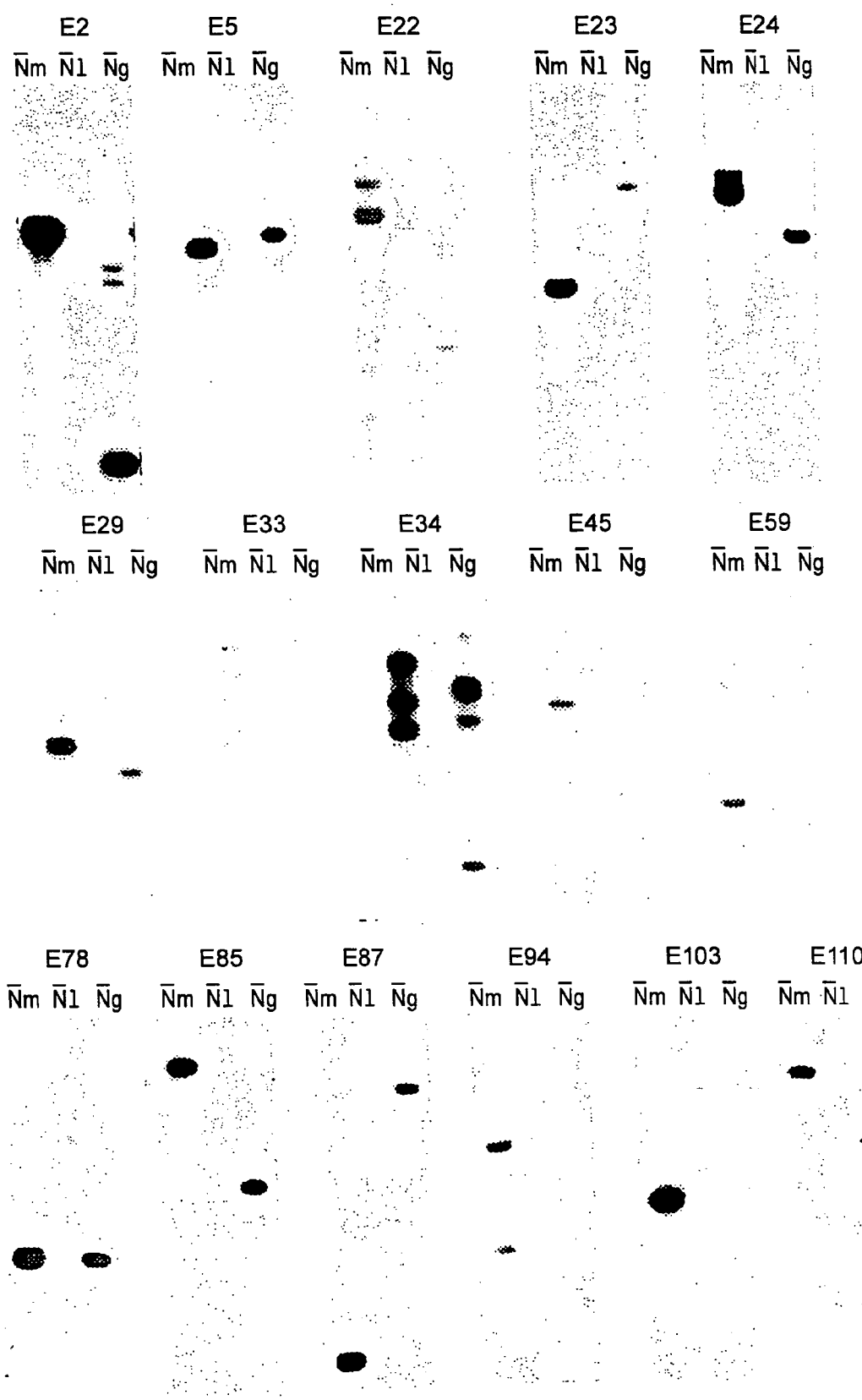

In these examples, reference will be made to FIGS. 1 to 11, which show, respectively, FIGS. 1A, 1B, 1C, 1D, 1E, 1F and 1G: analysis of the subtractive bank Tsp5091, FIG. 2: the distribution of the Nm-specific sequences, in contrast to Ng, on the chromosome of the strain Z2491 (left-hand part) and of Nm-specific sequences, in contrast to Nl (right-hand part), FIG. 3A to 3C: the reactivity of the clones of the 3 regions of the chromosome according to the invention towards a panel of strains of the genus *Neisseria*, FIG. 4: the position in region 2 of the chromosome of Nm of oligonucleotides used as probes, FIGS. 5, 6 and 7: the Southern blots of a panel of strains of the genus *Neisseria*, using parts of region 2 of Nm as probes, FIGS. 8A to 8C: the Southern blots with 3 subtractive banks over a panel of 12 strains of *Neisseria*, and FIGS. 9, 10 and 11: the reactivity of clones of the 3 subtractive banks with respect to Nm, Nl and Ng.

In the examples which follow, the following materials and methods were used:

Bacterial strains—To obtain the subtractive banks, strain Z2491 of Nm (Achtman et al., 1991, *J. Infect. Dis.* 164, 375-382), the strains MS11 (Swanson et al., 1974, *Infect. Immun.* 10, 633-644) and the strains 8064 and 9764 of Nl were used, it being understood that any other strain of the species in question could be used.

In order to verify the specificity of these banks, 6 strains of Nm, 4 strains of Ng, one strain of Nl (*Neisseria lactamica*) and one strain of Nc (*Neisseria cinerea*) were used.

The six strains of Nm are: Nm Z2491 of serogroup A, Nm 8013 of serogroup C (XN collection), Nm 1121, no serogrouping possible (XN collection), Nm 1912 serogroup A (XN collection), Nm 7972 of serogroup A (XN collection) and Nm 8216 of serogroup B (XN collection).

The four strains of Ng are: Ng MS11 (Pasteur Institute, Paris), Ng 403 (Pasteur Institute, Paris), Ng 6934 (Pasteur Institute, Paris), Ng WI (isolated from a disseminated gonococcal infection), Ng 4Cl, Ng 6493 and Ng FA 1090.

The strains of Nl are Nl 8064 and Nl 9764 (XN collection), and that of Nc is Nc 32165 (XN collection).

Molecular Genetics Techniques

Unless indicated otherwise, the techniques and reagents used correspond to those recommended by Sambrook et al (Sambrook et al 1989, Molecular Cloning: A Laboratory Manual. Cold Spring Harbor Laboratory Press). The oligodeoxynucleotides used in this study are:

| | | |
|---|---|---|
| RBAm12, | 3' AGTGGCTCCTAG 54 | (SEQ ID NO. 54) |
| RBam24, | 5' AGCACTCTCCAGCCTCTCACCGAG 3'; | (SEQ IN NO. 55) |
| Jbam12, | 3'GATCCGTTCATG 5'; | (SEQ ID NO. 60) |
| JBAM24, | 5' ACCGACGTCGACTATCCATGAACG 3'; | (SEQ ID NO. 61) |
| REco12, | AGTGGCTCTTAA; | (SEQ ID NO. 56) |
| Reco24, | 5' AGCACTCTCCAGCCTCTCACCGAG 3';. | (= RBam 24, SEQ ID NO: 55) |
| JEco12, | GTACTTGCTTAA; | (SEQ ID NO. 62) |
| JEco24, | 5' ACCGACGTCGACTATCCATGAACG 3'; | (= JBam24) (SEQ ID NO. 61) |
| NEco12, | AATTCTCCCTCG; | (SEQ ID NO. 64) |
| NEco24, | AGGCAACTGTGCTATCCGAGGGAG;. | (SEQ ID NO. 65) |

Transfer to Membranes (Southern Blots)

The transfers to membranes were effected by capillary transfers to positively charged nylon membranes (Boehringer Mannheim). The hybridizations were carried out at 65° C. in a solution comprising NaPi [sic] 0.5 M pH 7.2/EDTA 1 mM/SDS 7%/BSA 1%. The membranes were washed in a solution comprising NaPi [sic] 40 mM pH 7.2/EDTA 1 mM/SDS 1%. The final washing was carried out at 65° C. for 5 min.

The probe frp obtained with oligonucleotides based on the frpa sequence corresponds to 2.4 kb of the 5' end of the gene of the strain Z2491. The opc and rotamase probes corresponding to whole genes are produced from the strain Z2491 using oligonucleotides constructed on the basis of published sequences. The probes pilC1 and ppk (polyphosphate kinase) correspond to inserts of the plasmids pJL1 and pBluePPK6001 respectively.

EXAMPLE 1

Construction of Banks of DNAs Present in Nm and Absent from Ng a. "MboI" Bank

Construction—The DNA of Nm Z2491 was cleaved by the endonuclease MboI and subjected to two iterations of a method called CDA (comprehensive difference analysis) below. This method comprises subtractive hybridization in the presence of excess sheared DNA of Ng MS11 and amplification by PCR of those meningococcal sequences which, since they are absent from or do not have significant homology with the DNA of Ng MS11, could reanneal The chromosomal DNA of the strain Ng MS11 is sheared randomly by repeated passage through a hypodermic syringe until fragments of a size ranging from 3 to 10 kb are obtained. These DNA fragments are purified by extraction with phenol.

The chromosomal DNA of the strain Nm Z2491 is itself cleaved by the restriction endonuclease MboI. These DNA fragments (20 µg) are spliced with 10 nmol of annealed oligonucleotides RBam12 and RBam24. The excess primers are removed by electrophoresis over 2% agarose gel of low melting point. The part of the gel containing amplified fragments greater than 200 bp in size is excised and digested by β-agarase. These fragments are purified by extraction with phenol.

To carry out a subtractive hybridization (first iteration), 0.2 µg of the Nm DNA spliced with the RBam oligonucleotides is mixed with 40 µg Ng DNA in a total volume of 8 ml of a buffer EE 3× (a buffer EE 1× is composed of N-(2-hydroxyethyl)piperazine-N'-(3-propanesulphonic acid) 10 mM and EDTA 1 mM, and its pH is 8.0). This solution is covered with mineral oil and the DNA is denatured by heating at 100° C. for 2 min. 2 µl NaCl 5 M are added and the mixture is left to hybridize at 55° C. for 48 h. The reaction mixture is diluted to 1/10 in a preheated solution composed of NaCl and buffer EE, and in then immediately placed on ice.

10 µl of this dilution are added to 400 µl of PCR reaction mixture (Tris.HCl pH 9.0 10 mM; KCl 50 mM; $MgCl_2$ 1.5 mM; Triton X100 0.1%; 0.25 mM of each of the four triphosphate deoxynucleotides; Taq polymerase 50 units per ml). The mixture is incubated for 3 min at 70° C. to complete the ends of the reannealed meningococcal DNA fragments.

After denaturing at 94° C. for 5 min and addition of the oligonucleotide RBam24 in an amount of 0.1 nmol per 100 µl, the hybridizations are amplified by PCR (30 cycles of 1 min at 94° C., 1 min at 70° C. and 3 min at 72° C., followed by 1 min at 94° C. and 10 min at 72° C.; Perkin-Elmer GeneAmp 9600).

The amplified meningococcal fragments are separated from the primers and high molecular weight gonococcal DNAs on gel. They are digested by MboI and the oligonucleotides JBam12 and JBam 24 are spliced to them again. These spliced DNAs are again purified over gel and extracted with phenol.

A second iteration of the subtractive hybridization is carried out on 40 µg of the randomly sheared Ng DNA and 25 ng of the DNA spliced with the JBam oligonucleotides obtained from the first iteration of the subtractive hybridization. During this second iteration, amplification of the auto-annealed Nm DNA is effected with the aid of the oligonucleotide JBam24.

Specificity—In order to confirm their Nm specificity, the amplified sequences after the second iteration of the CDA method are labelled and used as a probe for the DNA digested by ClaI produced from a panel of six strains of Neisseria meningitidis, four of Neisseria gonorrhoeae, one of Neisseria lactamica and one of Neisseria cinerea.

The Southern blots obtained show that the amplified sequences resulting from the second iteration of the CDA method have a high reactivity with several bands corresponding to meningococci, and do not have a reactivity with the bands corresponding to the Ng, Nl and Nc strains.

The "MboI" bank thus appears to be Nm-specific.

Exhaustivity—In order to test the exhaustivity of the bank, all the products produced from the first and second iterations of the CDA method and also the initial chromosomal materials of Nm Z2481 [sic] and Ng MS11 are subjected to agarose gel electrophoresis, transferred to a membrane and brought into contact with probes comprising genes known to be meningococcus-specific, that is to say frp, opc and rotamase (Southern blotting).

As a result of these hybridizations, the Nm-specific gene frp is represented in the MboI bank by a fragment of 600 bp, but no activity is observed for the rotamase and opc genes. The MboI bank, although Nm-specific, therefore cannot be considered exhaustive.

Given their high specificity, the fragments produced by the second iteration of the CDA method for the MboI bank can nevertheless be cloned on the BamHI site of the plasmid pBluescript.

A sequence corresponding to any of the Nm-specific genes can be included in the subtractive bank only if it is carried by a restriction fragment of appropriate size. This condition is a function of two factors. Firstly, the probability that the largest fragments are entirely Nm-specific is low. Secondly, even if such fragments existed, they would be under-represented in the bank because of the limitations of the PCR technique, the amplification effectiveness of which decreases with increasing size of the fragments. Fragments greater that about 600 bp in size are not included in the bank. Because of the absence of Mbo fragments of suitable size from the chromosome of Nm Z2491, the rotamase and opc genes cannot be included in the bank. Any enzyme cannot by itself produce a small fragment corresponding to any Nm-specific gene. A second bank was therefore constructed using another restriction enzyme with a different specificity: Tsp509 [sic].

b. "Tsp509I" bank

Construction—The enzyme Tsp509I has the advantage of producing fragments of smaller size (less than about 1 kb) than the enzyme MboI.

Tsp509I recognizes the sequence AATT and leaves, projecting at 5', a sequence of 4 bases compatible with EcoRI. The oligonucleotides used are Reco, Jeco and NEco.

The method followed conforms with that followed for construction of the "MboI" bank described above. However, higher quantities of meningococcal DNA were used for the first iteration of the subtractive hybridization in order to compensate for the higher number of fragments of low molecular weight produced by Tsp509I. For the first iteration, 400 ng Nm DNA fragments and, in the second, 25 ng Nm fragments are subjected to subtractive hybridization with 40 μg randomly sheared Ng DNA.

For the construction of this "Tsp509I" bank, as a control, a third iteration of the subtractive hybridization is carried out using 40 μg sheared Ng DNA and 0.2 ng Nm fragments resulting from a digestion by Tsp509I and a resplicing, with NEco adaptors, of the fragments obtained as a result of the second iteration.

Specificity—As described for the previous bank, the product resulting from the second iteration of the CDA method is labelled and used as the probe for a panel of strains of Neisseria.

FIG. 1A illustrates the Southern blot hybridization of products of the second iteration of the CDA method with the DNA digested by ClaI of: Nm in track a, Ng MS11 in track b, Nm 8013 in track c, Ng 403 in track d, Nm 1121 in track e, Ng 6934 in track f, Nm 1912 in track g, Ng WI (strain DGI) in track h, Nm 7972 in track i, Nl 8064 in track j, Nc 32165 in track k, Nm 8216 in track 1.

In contrast to the high reactivity observed with all the Nm strains, a low or no reactivity is observed with the Ng, Nl and Nc strains.

The specificity of the bank was studied earlier by reacting membrane transfers (Southern blots) of the products produced by each of the three iterations of the CDA method with probes corresponding to pilC1 and ppk. These two genes are common to Nm and Ng.

FIG. 1B shows an agarose gel after electrophoresis of the chromosomes of Nm Z2491 and Ng Ms11, digested by Tsp509 [sic], and products resulting from each of the iterations of the CDA method.

In track a 1 μg of the chromosome of Nm was deposited, in track b 1 μg of that of Ng, in track c 0.15 μg of the products resulting from the first CDA iteration, in track d 0.1 μg of those of the second iteration, in track e 0.05 μg of the third iteration, MW representing the molecular size markers.

FIGS. 1C and 1D show gels obtained as described in FIG. 1B after transfer to the membrane (Southern blots) and hybridization with pilC1 (FIG. 1C) and ppk (FIG. 1D).

At the end of the second iteration of the CDA method, the sequences corresponding to the pilC1 and ppk genes are completely excluded from the bank.

Exhaustivity—The exhaustivity of the bank was examined by reacting the products resulting from the subtractive hybridization with the probes corresponding to three Nm-specific genes (frp, rotamase and opc).

These Nm-specific probes react with the amplification products resulting from the first and second iteration of the subtractive hybridization.

FIGS. 1E, 1F and 1G show gels obtained as described in FIG. 1B after transfer to the membrane (Southern blots) and hybridization with frpA (FIG. 1E), rotamase (FIG. 1F) and opc (FIG. 1G).

However, a third iteration of the subtractive hybridization leads to the loss of Nm-specific sequences, since the fragments which react with the rotamase and opc genes are absent from this third iteration.

In consideration of all these data, it emerges that the products resulting from the second iteration of the CDA method are Nm-specific and also constitute an exhaustive bank of Nm-specific sequences.

The products resulting from this second iteration are cloned at the EcoRI site of the plasmid pBluescript.

The bank produced by Tsp509I is more exhautive [sic] than the bank produced by MboI, as the theory considerations based on the enzymatic production of smaller restriction fragments would suggest.

In accordance with this aspect, it should be noted that the Tsp509I bank is less redundant than the MboI bank, that is to say it comprises less duplication of clones. 86% of the clones of the Tsp509I bank correspond to distinct sequences, while only 43% of the clones correspond to distinct sequences in the MboI bank (data not shown).

The bank produced by Tsp509I thus constitutes a source of Nm-specific clones.

EXAMPLE 2

Analysis of the Clones of the Subtractive Bank

Cloning and Sequencing of the Nm-specific DNAs

The DNAs of the subtractive banks are clones at the BamHI (MboI bank) or EcoRI (Tsp509I bank) site of the plasmid pBluescript, and then transformed in DH5α of E. coli. The inserts are amplified by PCR carried out on the transformed colonies using the primers M13-50 and M13-40, the latter primer being biotinylated on its 5' end.

Sequencing was carried out on each PCR product after separation of the biotinylated and non-biotinylated strands using the system of Dynabeads M-280 with streptavidin (Dynal, Oslo). The sequences are screened according to their homologies with previously published sequences using the computer programs Blastn and Blastx (NCBI, USA and Fasta).

The PCR products resulting from the transformed bacteria colonies after using the primers M13-40 and M13-50 as described above were labelled by incorporation with random priming of $\alpha\text{-}^{32}$P-dCTP and were used as a probe for the membrane transfers of the chromosomal DNA digested by ClaI of strains Nm Z2491 and Ng MS11, as described above, in order to verify their specificity.

Mapping of Clones on the Chromosome of the Strain Nm Z2491.

The results of studies carried out with 17 clones of the "MboI" bank (designated by the letter B) and 16 clones of the "Tsp5091" bank (designated by the letter E), each of these clones having a unique sequence and being without counterpart in Ng, are reported.

The positions of the DNA sequences corresponding to cloned Nm-specific products were determined with respect to the published map of the chromosome of Nm Z2491 (Dempsey et al. 1995, J. Bacteriol. 177, 6390-6400) and with the aid of transfers to membranes (Southern blots) of agarose gel subjected to pulsed field electrophoresis (PFGE).

The Nm-specific clones are used as probes for a hybridization on membranes (Southern blots) of the DNA of Nm Z2491 digested with enzymes of rare cutting sites, that is to say PacI, PmeI, SgfI, BglII, SpeI NheI and SgfI.

The gels (20×20 cm) were gels of 1% agarose in a buffer TBE 0.5× and were subjected to electrophoresis at 6 V/cm for 36 hours according to pulsation periods varying linearly between 5 and 35 seconds.

The hybridizations on the membrane (Southern blots) were carried out as described above.

The results obtained are shown on FIG. 2: the reactivity was located by comparison with the positions of the fragments of corresponding size on the published map. The positions of all the genetic markers mapped by Dempsey et al (mentioned above) are visualized with the aid of points on the linear chromosomal map. The Nm-specific genes disclosed previously are labelled with an asterisk. The two loci called "frp" correspond to the frpA and frpC genes. The "pilC" loci correspond to the pilC1 and pilC2 genes, which are pairs of homologous genes and are not distinguished on the map. The accuracy of the positions of the Nm-specific clones of the invention depends on the overlapping of reactive restriction fragments. On average, the position is +/−20 kb.

This mapping reveals a non-random distribution of the Nm-specific sequences. The majority of the Nm-specific sequences belong to three distinct groups. One of these groups (region 1) corresponds to the position of genes relating to the capsule which have been described previously.

A distinction is made between:
E109, E138, B230 and B323 as being region 1,
B322, B220, B108, B132, B233, B328, E139, E145 as B101 as being region 2, and
B306, E114, E115, E124, E146, E120, E107, E137 and 142 as being region 3.
63% of the sequences identified as specific to meningococci are located inside these three distinct regions.

This grouping contrasts with the distribution of previously disclosed Nm-specific genes (frpA, frpc, porA, opc and the region relating to the capsule).

This prior art would suggest in fact that the Nm-specific genes, with the exception of functional genes relating to the capsule, were dispersed along the chromosome.

Mapping of Nm-specific sequences on the chromosome leads to an unexpected result with regard to the prior art.

The majority of the genetic differences between the meningococcal and gonococcal strains tested are grouped in three distinct regions.

Meningococcal genes relating to the capsule are grouped in region 1.

The function of genes of the other regions is unknown, but homologies with published sequences (table 1) suggest similarities between certain genes of region 3 and bacteriophage transposase and regulatory proteins. No meningococcal virus has been characterized and it is tempting to think that these sequences are of phagic origin. Interestingly, the genome of *H. influenzae* also contains a sequence homologous to that of the Ner regulatory protein of phage Mu, but it is not known if it is a functional gene.

The clone B208 has a high homology (48%; identical, 91% homology for 33 amino acids) with a clone of conserved regions field III) in the class of proteins which bind to TonB-dependent ferric siderophors.

The proximity of this clone with the Nm-specific porA genes and the frp genes regulated by iron, and in particular the possibility that it is an Nm-specific receptor protein exposed on the external membrane in itself is a good candidate for further research.

The clone B339 corresponds to the Nm-specific insertion sequence IS1106.

The low homology between the clone B134 and the *Aeromonas* insertion sequence and also the presence of multiple copies of the clone B134 among the various strains of Nm suggest that it could be a new type of Nm-specific insertion sequence.

The possibility that the regions containing the Nm-specific clones could correspond to pathogenicity islets as described previously for *E. coli* and *Y. pestis* is of particular interest.

The clones isolated in this invention will allow better understanding of the relevance of Nm-specific regions in allowing cloning and sequencing of larger chromosomal fragments, and directly by their use for loci mutations.

Finally, detection of meningococcus-specific genes possibly involved in the pathogenicity of the organism allows targeting of suitable antigens which can be used in an antimeningococcal vaccine.

The effectiveness and the speed of the method according to the inventions enables it to be used in a large number of situations for which the genetic differences responsible for a phenotype peculiar to one of 2 close pathogens are investigated.

Study of the Reactivity of the Clones of Regions 1, 2 and 3 Towards a Panel of Strains of *Neisseria*.

The PCR products corresponding to inserts of each of the clones were collected and used as probes for hybridization on membranes (Southern blots) for a panel of strains of Nm, Ng, Nl and Nc.

Regions 1 and 2 produce a limited number of bands for each of the meningococci. This suggests that these regions are both Nm-specific and common to all the meningococci.

Figures 3A, 3B, 3C:
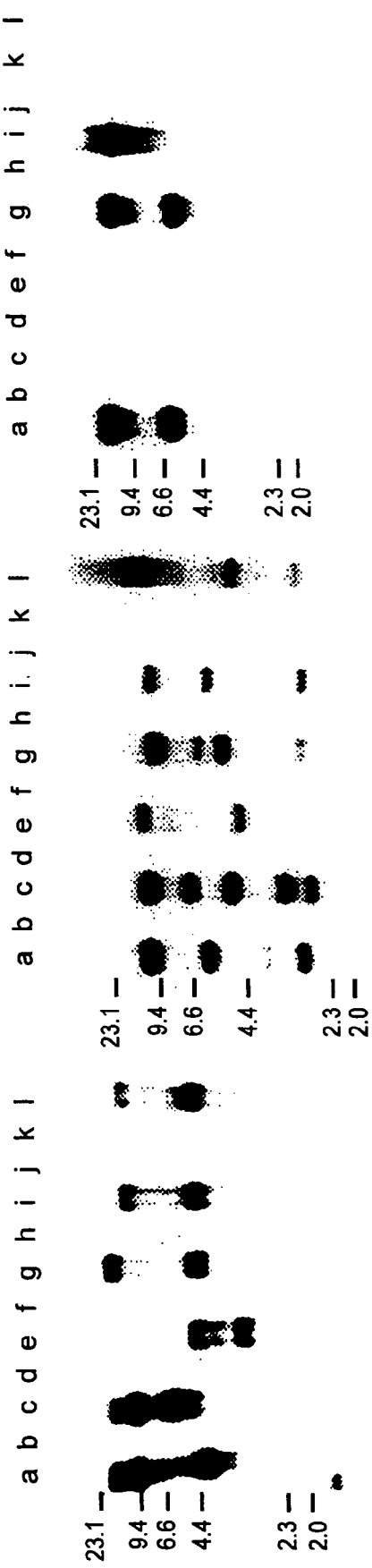

FIG. 3 illustrates the reactivity of the clones of regions 1, 2 and 3 towards a panel of neisserial strains. The clones of regions 1 (FIG. 3A), 2 (FIG. 3B) and 3 (FIG. 3C) taken together were used as probes towards a panel of meningococci, gonococci and towards a strain of Nl and Nc.

The tracks are as follows: DNA of: Nm Z2491 in track a, of Ng MS11 in track b, of Nm 8013 in track c, of Ng 403 in track d, of Nm 1121 in track e, of Ng 6934 in track f, of Nm 1912 in track g, of Ng WI (strain DGI) in track h, of Nm 7972 in track i, of Nl 8064 in track j, of Nc 32165 in track k, and of Nm 8216 in track l.

Remarkably, region 3 has reactivity only with the meningococci of serogroup A. This region 3 is therefore specific to a sub-group of Nm.

A comparison was made with the known sequences in the databanks in order to evaluate the possible functions of the cloned regions.

Table 1 which follows gives the positions of specific clones on the chromosomal map and the homologies with known sequences.

TABLE 1

Position of specific clones on the chromosomal map and homologies with known sequences

| Name of clone* | Size of insert | Reactive fragments | | | | | Position on Z2491 | Homologies of protein sequences |
|---|---|---|---|---|---|---|---|---|
| | | Pac | Pmc | Bgl | Spe | Nhe | Sgf | |
| B305 | 259 | 18-20 | 15-17 | 22-23 | 18 | 11-13 | 2 | λ736 |
| B333 | 235 | | 15-17 | 22-23 | 18 | 11-13 | 2 | λ736 |
| E109[1+] | 211 | | 6-7 | 11-15 | 10 | 11-13 | 2 | tufA protein LipB |
| | | | | | | | | ctrA  *N. meningitidis* ($3 \times 10^{-26}$) |

TABLE 1-continued

Position of specific clones on the chromosomal map and homologies with known sequences

| Name of clone* | Size of insert | Pac | Reactive fragments Pmc | Bgl | Spe | Nhe | Sgf | Position on Z2491 | Homologies of protein sequences |
|---|---|---|---|---|---|---|---|---|---|
| E138[1+] | 315 | 1 | 6-7 | 11-15 | 10 | 11-13 | 2 | tufA ctrA | protein LipB *N. meningitidis* ($4 \times 10^{-75}$) |
| B230[1] | 356 | 1-3 | 6-7 | 1 | 10 | 11-13 | 2 | ctrA | protein KpsC *E. coli* ($3 \times 10^{-53}$) |
| B323[1] | 363 | 1 | 6-7 | 1 | 10 | 11-13 | 2 | ctrA | protein CtrB *N. meningitidis* ($2 \times 10^{64}$) |
| B322[2] | 210 | | 2 | 16-18 | 6 | 1 | 5 | pilQ/λ740 | HlyB *S. marcescens* ($4 \times 10^{-15}$) |
| B220[2] | 341 | | 2 | 16-18 | 6 | ≧18 | 5 | pilQ/λ740 | |
| B108[2] | 275 | | 2 | 19-21 | 6 | >18 | 5 | pilQ/λ740 | |
| B132[2] | 411 | 2 | 2 | 19-21 | 6 | ≦18 | 5 | pilQ/λ740 | |
| B233[2] | 164 | 1-3 | 2 | 19-21 | 6 | ≦18 | 5 | pilQ/λ740 | |
| B328[2] | 256 | 1-3 | 2 | 22-23 | 6 | ≦18 | 5 | pilQ/λ740 | |
| E139[2] | 324 | 2 | 2 | 19-21 | 6 | ≦18 | 5 | pilQ/λ740 | |
| E145[2] | 343 | 2 | 2 | 19-21 | 6 | ≦18 | 5 | pilQ/λ740 | |
| B101[2] | 254 | ≧20 | 2 | 19-21 | 6 | ≦18 | 5 | pilQ/λ740 | |
| E103q | 334 | | 2 | 11-15 | 3-5 | 10 | 3 | λ644 | |
| B326[§] | 314 | | 2 | 11-15 | 3-4 | 10 | 3 | λ644 | |
| B326 (low reactivity) | | | 5 | 6 | 16 | 2 | 1 | argF | |
| B342 | 167 | | 2 | 19 | 3-4 | 6-7 | 3 | iga | |
| E136 | 249 | | 2 | 7 | 1 | 3 | 3 | lepA | |
| B208 | 177 | | 1 | 2 | 3-4 | 2 | 1 | porA | FeIII pyochelin receptor *P. aeruginosa* ($5 \cdot 10^{-4}$) |
| =B306[3#] | 219 | 11 | 5 | 11-12 | 5 | 2 | 4 | parC | |
| E114[3] | 227 | 11 | 5 | 11-12 | 5 | 2 | 4 | parC | |
| E115[3#] | 251 | | 5 | 11-15 | 5 | 2 | 4 | parC | |
| E124[3] | 208 | | 5 | 11-12 | 5 | 2 | 4 | parC | |
| E146[3] | 146 | | 5 | 11-15 | 5 | | 4 | parC | |
| E120[3] | 263 | | 5 | 3-4 | 5 | 16 | 4 | opaB | |
| E107[3] | 248 | 11 | 14-17 | 3-4 | 5 | 16 | 4 | opaB | |
| E137[3] | 274 | | 14-17 | 3-4 | 5 | 16 | 4 | opaB | Transposase Bacteriophage D3112 ($6 \times 10^{-12}$) |
| E142[3] | 230 | | 14-17 | 3-4 | 5 | 16 | 4 | opaB | Protein Ner-Like *H. influenzae* ($6 \times 10^{-23}$) Protein binding to the DNA Ner, phage mu ($3 \times 10^{-18}$) |
| E116 | 379 | 5-7 | 11-13 | 3-4 | 2 | 6-7 | 8 | λ375 | |
| B313 | 436 | 9 | 9 | 3-4 | 13-14 | 5 | 2 | Λ611 | |
| B341 | 201 | 8-10 | 9 | 3-4 | 13-14 | 5 | 2 | λ611 | |
| E102 | 238 | | 11-13 | 3-4 | 19 | 5 | 2 | λ601 | Hypothetical protein H11730 *H. influenzae* ($7 \times 10^{-24}$) |
| B134 | 428 | | | multiple | | | | | transposase ISAS2 *Aeromonas salmonicida* ($5 \times 10^{-5}$) |
| B339 | 259 | | | multiple | | | | | transposase IS 1106 *N. meningitidis* ($6 \times 10^{-45}$) |

The level of homologies found, as given by the Blastx program, are indicated in parentheses

*)The clones labelled with the index "[1]", "[2]" or "[3]" belong to regions "1", "2" or "3" respectively of the chromosome of *N. meningitidis* Z2491.

+)E109 and E138 are contiguous clones

§)B306 and E115 overlap

)B236 also has a low reactivity in the region of arg F q)Clone E103 contains a Tsp509 I site and can therefore contain two inserts; however, since it reacts only with a single fragment ClaI (Oks) of the chromosome of *N. meningitidis* Z2491 and occupies only one position on the map, this clone is included here.

Firstly, it can be seen that the clones of region 1 all correspond to genes involved in biosynthesis of the capsule. These genes have previously been studied among the Nm of serogroup B (Frosch et al. 1989, Proc. Natl. Acad. Sci. USA 86, 1669-1673 and Frosch and Muller 1993, Mol. Microbiol. 8 483-493).

With the exception of a low homology with the haemolysin activator of *Serratia marcescens*, the clones of region 2 have no significant homology with published sequences, either in the DNA or the proteins.

Two of the clones of region 3 have interesting homologies with proteins which bind to the DNA, in particular the bacteriophage regulatory proteins and transposase proteins.

Clone B208 has a high homology with one of the conserved regions in one class of receptors (TonB-dependent ferric siderophor).

Clones B134 and B339 hybridize with several regions of the chromosome (at least 5 and at least 8 respectively).

Data relating to. the sequences show that clone B339 corresponds to the Nm-specific insertion sequence S1106.

The translation of the clone B143 has a limited homology with the transposase of an *Aeromonas* insertion sequence (SAS2) (Gustafson et al. 1994, J. Mol. Biol. 237, 452-463). We were able to demonstrate by transfer on a membrane (Southern blots) that this clone is an Nm-specific entity present in multiple copies in the chromosomes of every meningococcus of the panel tested.

The other clones have no significant homology with the published neisserial sequences, and furthermore nor with any published sequence. These clones therefore constitute, with the majority of the other clones isolated, a bank of totally new Nm-specific loci.

EXAMPLE 3

Study of Region 2 of the Nm Chromosome

Determination and Characterization of the Sequence of Region 2

PCR amplification is carried out with the chromosomal DNA of strain Z2491 of serogroup A, sub-group IV-1 using oligonucleotide primers formulated from each of the sequences of clones of region 2 in several different combinations. The PCR products which overlap are sequenced from the 2 strands using the chain termination technique and automatic sequencing (ABI 373 or 377).

To prolong the sequence beyond the limits of the clones available, partial SauIIIA fragments of 15 kb of the strain Z2491 are cloned in Lambda DASH-II (Stratagène).

The phages containing the inserts overlapping region 2 are identified by hybridization with clones of this region as probes. The DNA inserted is sequenced from the ends of the inserts, and these sequences are used to formulate new primers which will serve to amplify the chromosomal DNA directly, and not the phagic DNA.

An amplification of the chromosomal DNA is obtained using these new primers and those of the sequence previously available.

These PCR products are also sequenced from the 2 strands, which leads to a complete sequence of 15,620 bp (SEQ ID No. 36). The reading frames of this sequence which start with ATG or GTG and are characterized by a high codon usage index are analysed.

This analysis reveals 7 ORFs of this type which fill the major part of the sequence of 15,620 bp. The positions of these ORFs are the following:

ORF-1: 1330 to 2970 (SEQ ID No. 37); ORF-2: 3083 to 9025 (SEQ ID No. 38); ORF-3: 9044 to 9472 (SEQ ID No. 39); ORF-4: 9620 to 12118 (SEQ ID No. 40); ORF-5: 12118 to 12603 (SEQ ID No. 42); ORF-6: 12794 to 13063 (SEQ ID No. 43); ORF-7: 13297 to 14235 (SEQ ID No. 44); and ORF-8: 14241 to 15173 (SEQ ID No. 45).

ORF-4 starts with the codon GTG and overlaps a slightly smaller ORF (SEQ ID No. 41) in the same reading frame (10127-12118, frame 2), which starts with the codon ATG.

ORF-4 codes for a protein which has structural homologies with a family of polypeptides comprising pyocins (*Pseudomonas aeruginosa*), collcins and intimins (*Escherichia coli*), which are bactericidal toxins (pyocins, collcins) or surface proteins involved in adhesion of bacteria to eukaryotic proteins. ORF-7 encodes a protein, the sequence of which contains a potentially transmembrane region and which has structural homologies with periplasmic proteins or proteins inserted in the external membrane of bacteria. The structural homologies of ORF-4 and ORF-7 have been identified with the aid of the PropSearch program.

Investigation of sequences homologous to other ORFs in GenBank with the aid of the BLAST program revealed a homology between the N-terminal regions of ORF-2 and filamentous haemagglutinin B of *Bordetella pertussis* (43% similarity, 36% identical over 352 amino acids) and between ORF-1 and the protein fhaC of *Bordetella pertussis* (35% similarity, 27% identical over 401 amino acids). ORF-1 and ORF-2 are neighbouring genes in the strain Z249I and filamentous haemagglutinin B of *Bordetella pertussis* and fhaC are neighbouring genes in *Bordetella pertussis*, which reinforces the probability that these homologies reflect functional homologies.

Confirmation of the specificity of region 2 with respect to Nm

Southern blots are carried out using the DNA probes obtained by PCR amplification of various parts of region 2 using oligonucleotide primers formulated from sequences of clones of region 2.

Figure 4:
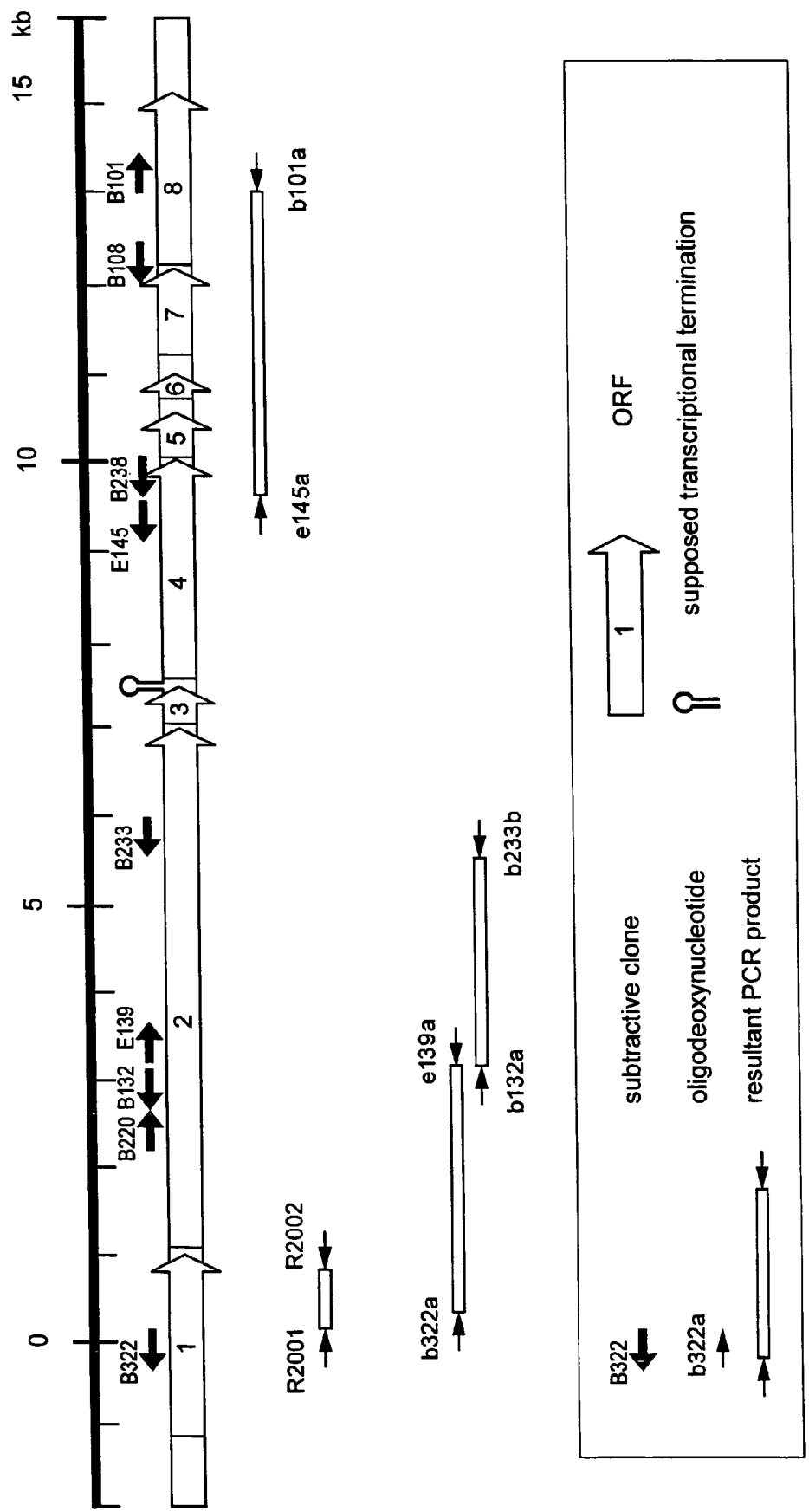

The approximate position of these oligonucleotides is shown on FIG. 4.

These are the oligonucleotides called R2001 (SEQ ID No. 46) and R2002 (SEQ ID No. 47) in one half of ORF-1, the oligonucleotides b332a (SEQ ID No. 48), e139a (SEQ ID No. 49), b132a (SEQ ID No. 50) and b233b (SEQ ID No. 51) in one half of ORF-1+the majority of ORF-2, and the oligonucleotides e145a (SEQ ID No. 52) and b101a (SEQ ID No. 53) in ⅓ of ORF-4+ORF-5 to 7.

The three Southerns are carried out under the following hybridization conditions:

16 h at 65° C.,
NaPO$_4$ 0.5 M, pH 7.2
EDTA-Na 0.001 M
1% sodium dodecylsulphate.

For the washing, heating is carried out for 10 min at 65° C., and NaPO$_4$ 0.5 M, pH 7.2; EDTA-Na 0.001 M, 1% sodium dodecylsulphate are used.

Figure 5:
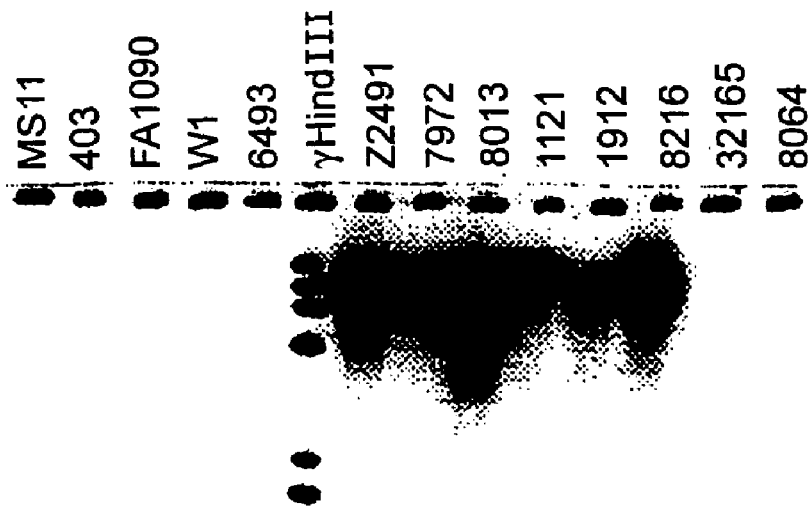
Figure 6:
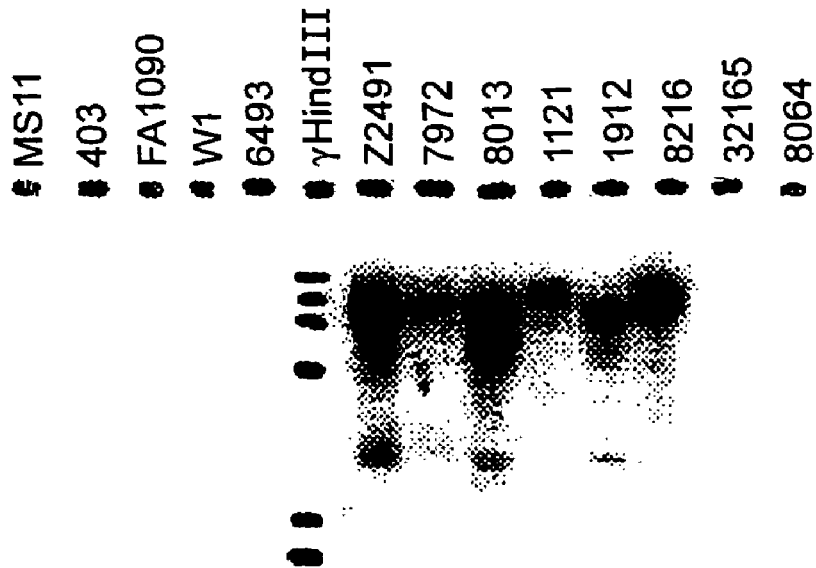
Figure 7:

FIGS. 5, 6 and 7 respectively show the Southern blots obtained with each of the abovementioned ORF parts.

The 14 tracks correspond respectively, in each of the Southerns, to

1: MS11 (Ng)
2: 403 (Ng)
3: FA1090 (Ng)
4: W1 (Ng)
5: 6493 (Ng)
6: marker (lambda hindIII)
7: Z2491 (Nm, gpA)

8: 7972 (Nm gpA)
9: 8013 (Nm, gpC)
10: 1121 (Nm, grouping not possible)
11: 1912 (Nm, gpB)
13: 32165 (Nc)
14: 8064 (Nl).

Given that a panel of strains of *Neisseria* is used in these experiments and that each well is charged with a similar amount of digested DNA, these 3 Southern blots clearly show that the sequences corresponding to region 2 are found in all the meningococci tested and that significant homologous sequences do not exist in the genome of the Ng of the strains tested.

EXMAPLE 4

Identification of Regions of the Nm Genome Absent from Nl and Common with Ng

The technique described in example 1 is followed, but the chromosomal DNA of one strain of Nm (Z2491) and 2 strains of Nl (XN collections), equal parts of the DNAs of which are mixed, is used.

2 subtractions are performed using the R and J series of primers. Three different banks are thus obtained.

Two banks, called Bam and Eco, are obtained respectively by digestion of the chromosomal DNA of Nm Z2491 by MboI and Tsp509I; a third bank, called Cla, which results from digestion of the chromosomal DNA of Nm by MspI, is obtained using the primer set RMsp10, RMsp24, JMsp10 and JMsp24. All the primers used are shown in the following table 2.

TABLE 2

Adapters for differential banks
Chromosomal DNA digested by Cloning in pBluescript by
MboI → BamHI Tsp509I → EcoRI MspI → ClaI First subtraction cycle

| | | |
|---|---|---|
| RBam12 3' | AGTGGCTCCTAG 5' | (SEQ ID No. 54) |
| RBam24 5' AGCACTCTCCAGCCTCTCACCGAG 3' | | (SEQ ID No. 55) |
| REco12 | AGTGGCTCTTAA | (SEQ ID No. 56) |
| RBam24 5' AGCACTCTCCAGCCTCTCACCGAG 3' (REco 24 = RBam 24) | | (SEQ ID No. 55) |
| RMsp10 | AGTGGCTGGC | (SEQ ID No. 57) |
| RMsp24 5' AGCACTCTCCAGCCTCTCACCGAC 3' | | (SEQ ID No. 58) |

Second subtraction cycle

| | | |
|---|---|---|
| Jbam12 3' | GTACTTGCCTAG 5' | (SEQ ID No. 59) |
| JBam24 5' ACCGACGTCGACTATCCATGAACG 3' | | (SEQ ID No. 60) |
| JEco12 | GTACTTGCTTAA | (SEQ ID No. 61) |
| JBam24 5' ACCGACGTCGACTATCCATGAACG 3' (JEco 24 = JBam 24) | | (SEQ ID No. 60) |

TABLE 2-continued

| | | |
|---|---|---|
| JMsp10 | GTACTTGGGC | (SEQ ID No. 62) |
| JMsp24 5' ACCGACGTCGACTATCCATGAACC 3' | | (SEQ ID No. 63) |

After 2 subtractions, the entire product of each amplification is labelled and used as a probe.

The subtractive banks are checked by Southern blotting over a panel of 12 strains of *Neisseria* (chromosomal DNA cut by ClaI). The hybridization conditions are identical to those given in example 1.

Figure 8A:
Figure 8B:
Figure 8C:
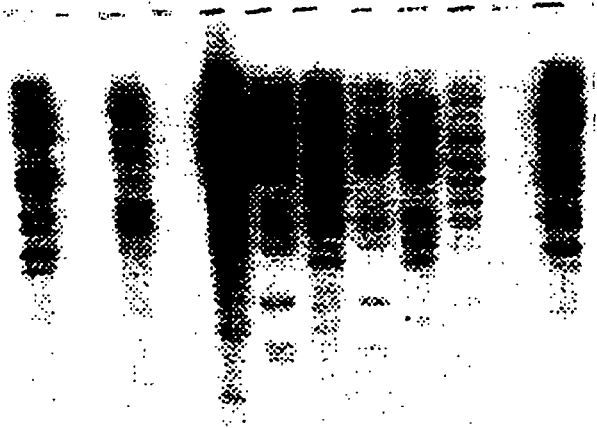

These Southern blots are shown on FIGS. 8A to 8C, which relate respectively to the MboI/BamHI bank, to the MspI/ClaI bank and to the Tsp509I/EcoRI bank.

The 12 tracks correspond respectively, to
1: Nm Z2491 (group A)
2: Nl 8064
3: Nm 8216 (group B)
4: Nl 9764
5: Nm 8013 (group C)
6: Ng MS11
7: Nm 1912 (group A)
8: Ng 4C1
9: Nm 1121 (grouping not possible)
10: Ng FA1090
11: Nc 32165
12: Nm 7972 (group A)

Examination of the Southern blots shows that the sequences contained in each bank are specific to Nm and are not found in Nl. Furthermore, the reactivity found with the strains of Ng suggests that some of these sequences are present in Ng.

Each of these banks was then cloned in pBluescript at the BamHI site for Bam, or the EcoRI sit for Eco, or the ClaI site for Cla. In order to confirm the specificity of the clones with respect to the Nm genome, restriction of the individual clones and radiolabelling thereof were carried out. The clones showing reactivity for both Nm and Ng were kept for subsequent studies. These clones are shown on FIGS. 9, 10 and 11, which give the profiles with respect ot Nm, Nl and Ng of 5 clones of the Bam bank (FIG. 9), 16 clones of the Eco bank (FIG. 10) and 13 clones of the Cla bank (FIG. 11).

These clones were sequenced using universal and reverse primers. They are

Bam Clones partial B11 of 140 bp (SEQ ID No. 66), partial B13 estimated at 425 bp (SEQ ID No. 67), B26 of 181 bp (SEQ ID No. 68), B33 of 307 bp (SEQ ID No. 69), B40 of 243 bp (SEQ ID No. 70), Cla Clones C16 of 280 bp (SEQ ID No. 72), partial C20 estimated at 365 bp (SEQ ID No. 73), partial C24 estimated at 645 bp (SEQ ID No. 74), partial C29 estimated at 245 bp (SEQ ID No. 75), C34 of 381 bp (SEQ ID No. 76), C40 of 269 bp (SEQ ID No. 77), C42 of 203 bp (SEQ ID No. 78), p C43 of 229 bp (SEQ ID No. 79), C45 of 206 bp (SEQ ID No. 80), C47 of 224 bp (SEQ ID No. 81), C62 of 212 bp (SEQ ID No. 82), and C130 (5' . . . ) estimated at 900 bp (SEQ ID No. 83), and Eco Clones E2 of 308 bp (SEQ ID No. 84), partial E5 estimated at 170 bp (SEQ ID No. 85), partial E22 estimated at 300 bp (SEQ ID No. 86), E23 of 273 bp (SEQ ID No. 87), E24 of 271 bp (SEQ ID No. 88), E29 of 268 bp (SEQ ID No. 89), partial E33 estimated at 275 bp (SEQ ID No. 90), partial E34 estimated at 365 bp (SEQ ID No. 91), E45 of 260 bp (SEQ ID No. 92), E59 estimated at greater than 380 bp (SEQ ID No. 93), E78 of 308 bp (SEQ ID No. 94), E85 of 286 bp (SEQ ID No. 95), E87 of 238 bp (SEQ ID No. 96), partial E94 greater than 320 bp (SEQ ID No. 97), partial E103 greater than 320 bp (SEQ ID No. 98) and E110 of 217 bp (SEQ ID No. 99).

Mapping of each clone was carried out on the chromosome of Nm Z2491 as described in example 1. The results obtained are given on the right-hand part of FIG. 2. It is found that these clones correspond to regions called 4 and 5. These regions are therefore made up of sequences present both in Nm and in Ng, but not found in Nl. It is therefore regarded that these are sequences which code for virulence factors responsible for the initial colonization and penetration of the mucosa. Region 4 is located between argF and regF on the chromosome of Nm 2491 [sic], and region 5 is located between the lambda 375 marker and penA. This region probably contains sequences which code for an Opa variant and a protein which binds transferrin.

A comparison with the known sequences in the databanks has half [sic] that in region 4 only the clone C130 has a homology, that is to say with MspI methylase. In region 5, no homology with known sequences was found with the clones C8, E2, B40, C45, E23 and E103. For the other clones, the homologies are the following:

B11 arginine decarboxylase SpeA; C29 arginine decarboxylase SpeA; C62 oxoglutarate/malate transporter; repetitive DNA element; E34 repetitive DNA element; E94 murine endopeptidase MepA ; C47 citrate synthase PrpC; E78 citrate synthase PrpC

EXAMPLE 5

Demonstration of the Presence of One or More Strains of *Neisseria meningitidis* in a Biological Sample A biological sample of the cephalorachidian fluid, urine, blood or saliva type is taken.

After filtration and extraction, the DNAs present in this sample are subjected to gel electrophoresis and transferred to a membrane by Southern blotting.

A nucleotide probe constructed by labelling SEQ ID No. 5 with $^{32}P$ is incubated with this transfer membrane.

After autoradiography, the presence of reactive band(s) allows diagnosis of the presence of *Neisseria meningitidis* in the sample.

EXAMPLE 6

Vaccine Composition Including in its Spectrum Antimeningococcal Prophylaxis and Intended for Prevention of Any Form of Infection by *Neisseria meningitidis*

The peptide coded by a sequence including SEQ ID No. 10 is conjugated with a toxin.

This conjugated peptide is then added to a composition comprising the anti-*Haemophilus* and antipneumococcal vaccine, or any other childhood vaccine.

After having been sterilized, the resulting composition can be injected parenterally, subcutaneously or intramuscularly.

This same composition can also be sprayed on to mucosa with the aid of a spray.

104

105

The invention claimed is:
1. A DNA vector, comprising an isolated DNA which is specific to *Neisseria meningitidis* (Nm) and *Neisseria gonorrhoeae* (Ng), or the complement of said DNA which is specific to *Neisseria meningitidis* (Nm) and *Neisseria gonorrhoeae* (Ng),
   wherein said DNA or the complement of said DNA hybridizes on a Southern blot to SEQ ID NO:95 and does not hybridize on a Southern blot to a DNA sequence of *Neisseria lactamica* (Nl) strain Nl8064, under the following hybridization conditions:
   16 h at 65°C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM NaPO$_4$ pH 7.2, 1 mM EDTA, and 1% SDS, the final wash being conducted at 65°C. for 5 minutes,
   provided that said DNA or the complement of said DNA is not pilC, or a gene involved in the biosynthesis of any one of a polysaccharide capsule, an IgA protease, pilin, a protein which binds transferrin, a protein which binds lactoferrin, and an opacity protein
   wherein said DNA is located in Nm within an islet involved in the colonization of the nasopharynx or invasion of the submucousal space or systemic dissemination of Nm.

2. A DNA vector, comprising an isolated DNA which is specific to *Neisseria meningitidis* (Nm) and *Neisseria gonorrhoeae* (Ng), or the complement of said DNA which is specific to *Neisseria meningitidis* (Nm) and *Neisseria gonorrhoeae* (Ng),
   wherein said DNA or the complement of said DNA hybridizes on a Southern blot to SEQ ID NO:95 and does not hybridize on a Southern blot to a DNA sequence of *Neisseria lactamica* (Nl) strain N18064, under the following hybridization conditions:
   16 h at 65° C., with a solution comprising 0.5 M NaPO4 pH 7.2, 0.001 M EDTA-Na, 1% bovine serum albumin and 7% sodium dodecylsulphate, followed by at least two washes in a solution comprising 40 mM NaPO$_4$ pH 7.2, 1 mM EDTA and 1% SDS, the final wash being conducted at 65° C. for 5 minutes,
   provided that said DNA or the complement of said DNA is not pilC, or a gene involved in the biosynthesis of any one of a polysaccharide capsule, IgA protease, pilin, a protein which binds transferrin, a protein which binds lactoferrin, and an opacity protein.

3. The DNA vector of claim 1 or 2, wherein the vector is a transfer or expression vector.

4. The DNA vector of claim 3 which is selected from the group consisting of a plasmid, a cosmid and a bacteriophage.

5. A DNA vector, comprising an isolated DNA which is specific to *Neisseria meningitidis* (Nm) and *Neisseria gonorrhoeae* (Ng), or the complement of said DNA which is specific to *Neisseria meningitidis* (Nm) and *Neisseria gonorrhoeae* (Ng),
   said DNA or the complement of said DNA being located on the chromosome of strain Z2491 between the locations of hybridization of clone B33 on the fragment containing region 4,
   wherein said DNA or the complement of said DNA hybridizes on a Southern blot to SEQ ID NO:95, and does not hybridize on a Southern blot to a DNA sequence of *Neisseria lactamica* (Nl) strain N18064, under the following hybridization conditions:
   16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM NaPO$_4$ pH 7.2, 1 mM EDTA and 1% SDS, the final wash being conducted at 65° C. for 5 minutes,
   provided that said DNA or the complement of said DNA is not pilC, or a gene involved in the biosynthesis of any one of a polysaccharide capsule, an IgA protease, pilin, a protein which binds transferrin, a protein which binds lactoferrin, and an opacity protein.

6. The DNA vector of claim 5, wherein the vector is a transfer or expression vector.

7. A DNA vector of claim 6 which is selected from the group consisting of a plasmid, a cosmid and a bacteriophage.

8. A DNA vector, comprising an isolated DNA which is specific to *Neisseria meningitidis* (Nm) and *Neisseria gonorrhoeae* (Ng), or the complement of said DNA which is specific to *Neisseria meningitidis* (Nm) and *Neisseria gonorrhoeae* (Ng),
   said DNA or the complement of said DNA being located on the chromosome of strain Z2491 between the pilC alleles on the fragment containing region 4,
   wherein said DNA or the complement of said DNA hybridizes on a Southern blot to a sequence comprising SEQ ID NO:95, and does not hybridize on a Southern blot to a DNA sequence of *Neisseria lactamica* (Nl) strain Nl8064, under the following hybridization conditions:
   16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM NaPO$_4$ pH 7.2, 1 mM EDTA and 1% SDS, the final wash being conducted at 65° C. for 5 minutes,
   provided that said DNA or the complement of said DNA is not pilC, or a gene involved in the biosynthesis of any one of a polysaccharide capsule, an IgA protease, pilin, a protein which binds transferrin, a protein which binds lactoferrin, and an opacity protein.

9. The DNA vector of claim 8, wherein the vector is a transfer or expression vector.

10. The DNA vector of claim 9 which is selected from the group consisting of a plasmid, a cosmid and a bacteriophage.

11. A DNA vector, comprising an isolated DNA which hybridizes on a Southern blot to the DNA of *Neisseria meningitidis* (Nm) strain Z2491 and *Neisseria gonorrhoeae* (Ng), or the complement of said DNA which hybridizes on a Southern blot to the DNA of *Neisseria meningitidis* (Nm) strain Z2491 and *Neisseria gonorrhoeae* (Ng),
   wherein said DNA or the complement of said DNA hybridizes on a Southern blot to SEQ ID NO:95 and does not hybridize on a Southern blot to a DNA sequence of *Neisseria lactamica (Nl) strain N*18064, under the following hybridization conditions:
   16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM NaPO$_4$ pH 7.2, 1 mM EDTA, and 1% SDS, the final wash being conducted at 65° C. for 5 minutes,
   provided that said DNA or the complement of said DNA is not pilC, or a gene involved in the biosynthesis of any one of a polysaccharide capsule, an IgA protease, pilin, a protein which binds transferrin, a protein which binds lactoferrin, and an opacity protein.

12. A DNA vector, comprising an isolated DNA which hybridizes on a Southern blot to the DNA of *Neisseria meningitidis* (Nm) strain Z2491 and *Neisseria gonorrhoeae* (Ng) strain MS11, or the complement of said DNA which hybridizes on a Southern blot to the DNA of *Neisseria meningitidis* (Nm) strain Z2491 and *Neisseria gonorrhoeae* (Ng) strain MS 11, wherein said DNA or the complement of said DNA hybridizes on a Southern blot to SEQ ID NO:95, and does not hybridize on a Southern blot to a DNA sequence of *Neisseria lactamica* (Nl) strain N18064, under the following hybridization conditions:

16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40mM NaPO$_4$ pH 7.2,1 mM EDTA, and 1% SDS, the final wash being conducted at 65° for 5 minutes, provided that said DNA or the complement of said DNA is not pilC, or a gene involved in the biosynthesis of any one of a polysaccharide capsule, an IgA protease, pilin, a protein which binds transferrin, a protein which binds lactoferrin, and an opacity protein.

13. The DNA vector of claim 11 or 12, wherein the vector is a transfer or expression vector.

14. The DNA vector of claim 13, which is selected from the group consisting of a plasmid, a cosmid and a bacteriophage.

15. A DNA vector, comprising an isolated DNA which hybridizes on a Southern blot to the DNA of *Neisseria meningitidis* (Nm) strain Z2491 and *Neisseria gonorrhoeae* (Ng), or the complement of said DNA which hybridizes to the DNA of *Neisseria meningitidis* (Nm) strain Z2491 and *Neisseria gonorrhoeae* (Ng), said DNA or the complement of said DNA being located on the chromosome of Nm strain Z2491 between the locations of hybridization of clone B33 on the fragment containing the region 4, wherein said DNA or the complement of said DNA hybridizes on a Southern blot to SEQ ID NO:95, and does not hybridize on a Southern blot to a DNA sequence of *Neisseria lactamica* (Nl) strain N18064, under the following hybridization conditions:

16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40 mM NaPO$_4$ pH 7.2, 1 MM EDTA and 1% SDS, the final wash being conducted at 65° C. for 5 minutes, provided that said DNA or the complement of said DNA is not pilC, or a gene involved in the biosynthesis of any one of a polysaccharide capsule, an IgA protease, pilin, a protein which binds transferrin, a protein which binds lactoferrin, and an opacity protein.

16. A DNA vector, comprising an isolated DNA which hybridizes on a Southern blot to the DNA of *Neisseria meningitidis* (Nm) strain Z2491 and *Neisseria gonorrhoeae* (Ng) strain MS11, or the complement of said DNA which hybridizes on a Southern blot to the DNA of *Neisseria meningitidis* (Nm) strain Z2491 and *Neisseria gonorrhoeae* (Ng) strain MS 11, said DNA or the complement of said DNA being located on the chromosome of strain Z2491 between the locations of hybridization of clone B33 on the fragment containing region 4, wherein said DNA or the complement of said DNA hybridizes on a Southern blot to SEQ ID NO:95, and does not hybridize on a Southern blot to a DNA sequence of *Neisseria lactamica* (Nl) strain N18064, under the following hybridization conditions:

16 h at 65° C., with a solution comprising 0.5 M NaPO$_4$ pH 7.2, 0.001 M EDTA-Na, 1% bovine serum albumin and 7% sodium dodecylsulphate, followed by at least two washes in a solution comprising 40mM NaPO$_4$ pH 7.2, 1 mM EDTA and 1% SDS, the final wash being conducted at 65° C. for 5 minutes, provided that said DNA or the complement of said isolated DNA is not pilC, or a gene involved in the biosynthesis of any one of the polysaccharide capsule, IgA proteases, pilin, a protein which binds transferrin, a protein which binds lactoferrin, and an opacity protein.

17. The DNA vector of claim 15 or 16, wherein the vector is a transfer or expression vector.

18. The DNA vector of claim 17 which is selected from the group consisting of a plasmid, a cosmid and a bacteriophage.

19. A DNA vector, comprising an isolated DNA which hybridizes on a Southern blot to the DNA of *Neisseria meningitidis* (Nm) strain Z2491 and *Neisseria gonorrhoeae* (Ng), or the complement of said DNA which hybridizes on the Southern blot to the DNA of *Neisseria meningitidis* (Nm) strain Z2491 and *Neisseria gonorrhoeae* (Ng), said DNA or the complement of said DNA being located on the chromosome of Nm strain Z2491 between the pilC alleles on the fragment containing the region 4, wherein said DNA or the complement of said DNA hybridizes on a Southern blot to SEQ ID NO:95, and does not hybridize on a Southern blot to a DNA sequence of *Neisseria lactamica* (Nl) strain N18064, under the following hybridization conditions:

16 h at 65° C., with a solution comprising 0.5 M NaPO4 pH 7.2, 0.001 M EDTA-Na, 1% bovine serum albumin and 7% sodium dodecylsulphate, followed by at least two washes in a solution comprising 40 mM NaPO$_4$ pH 7.2,1 mM EDTA and 1% SDS, the final wash being conducted at 65° C. for 5 minutes, provided that said DNA or the complement of said DNA is not pilC, or a gene involved in the biosynthesis of any one of a polysaccharide capsule,an IgA protease, pilin, a protein which binds transferrin, a protein which binds lactoferrin, and an opacity protein.

20. A DNA vector, comprising an isolated DNA which hybridizes on a Southern blot to the DNA of *Neisseria meningitidis* (Nm) strain Z2491 and *Neisseria gonorrhoeae* (Ng) strain MS11, or the complement of said DNA which hybridizes on a Southern blot to the DNA of *Neisseria meningitidis* (Nm) strain Z2491 and *Neisseria gonorrhoeae* (Ng) strain MS 11, said DNA or the complement of said DNA being located on the chromosome of Nm strain Z2491 between the pilC alleles on the fragment containing the region 4, wherein said DNA or the complement of said DNA hybridizes on a Southern blot to SEQ ID NO:95, and does not hybridize on a Southern blot to a DNA sequence of *Neisseria lactamica* (Nl) strain N18064, under the following hybridization conditions:

16 h at 65° C., with a solution comprising 0.5 M NaPO$_4$ pH 7.2, 0.001 M EDTA-Na, 1% bovine serum albumin and 7% sodium dodecylsuiphate, followed by at least two washes in a solution comprising 40 mM NaPO$_4$ pH 7.2, 1 mM EDTA and 1% SDS, the final wash being conducted at 65° C. for 5 minutes, provided that said DNA or the complement of said isolated DNA is not pilC, or a gene involved in the biosynthesis of any one of a polysaccharide capsule, an IgA protease, pilin, a protein which binds transferrin, a protein which binds lactoferrin, and an opacity protein.

21. The DNA vector of claim 19 or 20, wherein the vector is a transfer or expression vector.

22. The DNA vector of claim 21, which is selected from the group consisting of a plasmid, a cosmid and a bacteriophage.

* * * * *

SEQUENCE LISTING (1) GENERAL INFORMATION:

(iii) NUMBER OF SEQUENCES: 99

(2) INFORMATION FOR SEQ ID NO: 1:

(i) SEQUENCE CHARACTERISTICS:
        (A) LENGTH: 257 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 1:

```
GATCCGCTGC CGGCAGACGA ATATCAAGAC ATCTTCGATT TTATGAAACA GTATGACTTG      60

TCTTACCCGT ATGAATATCT GCAGGATTGG ATAGATTACT ATACGTTCAA AACCGATAAG     120

CTGGTATTTG GTAACGCGAA GCGAGAGTGA GCCGTAAAAC TCTGAGCTCC TGTTTTATAG     180

ATTACAACTT TAGGCCGTCT TAAAGCTGAA AGATTTTCGA AAGCTATAAA TTGAAGCCCT     240

TCCACAGTAC ATAGATC                                                   257
```

(2) INFORMATION FOR SEQ ID NO: 2:

(i) SEQUENCE CHARACTERISTICS:
        (A) LENGTH: 276 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 2:

```
GATCATGTTC AAATAGATAG GCATGGGAAG CTGCAGCTCT AACGTCCATG AAAATATGTT      60
GCATAGCTGC AAGCGGAACG CCTTTTCTTT CATCTACATA ATCTATAGAG TCAAGGCAAC     120
CGCTATTGAA ATTAGCAGTA TTGCCTATGA TTACATTAGT AATATGCTCA TACCATTTTT     180
GGGTGGTCAT CATATTGTGC CCCATTGTTA TCTCCTTATA TTGGTTTTAG AAGGAACTTT     240
GACAGGAAGA ATAACGGCCT TACCTGTTTG ACGATC                               276
```

(2) INFORMATION FOR SEQ ID NO: 3:

(i) SEQUENCE CHARACTERISTICS:
        (A) LENGTH: 428 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 3:

```
GATCTGGTGG TGTTTGCACA GGTAGGCGCA TACTTGTTCG GGACTGAGTT TGCGGCGGAT      60
AAGGGTGTCG ATGTGCTGAA TCAGCTGCGA ATCGAGCTTA TAGGGTTGTC GCTTACGCTG     120
TTTGATAGTC CGGCTTTGCC GCTGGGCTTT TTCGGCGCTG TATTGCTGCC CTTGGGTGCG     180
GTGCCGTCTG ATTTCGCGGC TGATGGTGCT TTTGTGGCGG TTAAGCTGTT TGGCGATTTC     240
GGTGACGGTG CAGTGGCGGG ACAGGTATTG GATGTGGTAT CGTTCGCCTT GGGTCAGTTG     300
CGTGTAGCTC ATGGCAATCT TTCTTGCAGG AAAGGCCGTA TGCTACCGCA TACTGGCCTT     360
TTTCTGTTAG GGAAAGTTGC ACTTCAAATG CGAATCCGCC GACCTCTTTC AGTTACAGCA     420
GCTTGATC                                                              428
```

(2) INFORMATION FOR SEQ ID NO: 4:

(i) SEQUENCE CHARACTERISTICS:
        (A) LENGTH: 390 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 4:

```
GATCCTGCAT TGACATCGGC CTTGGCTGTC AGGGTATTGT GACCGGTAAA GTCGGCATTA      60
CCGTTGGCCA ATAAGGATAC ATGACCGTCT GCAGAAACAG CATGAAGGCC GTCTGAAACG     120
```

-continued

```
ATATTGCCCT GCAATGCGGT GGTTTCGAGA GCCTTGGCTG CGTTCAGCTT GGTATTGCGA    180

AGCTGAATAT TGCCTTTGGC TGCCTGAATG TGCAGATTAC CCGAGTTGGT ACGCAGATTG    240

GTATTGGTAA CATTCAGCAA GCCTGCCTCC ACACCCATGT CTTTTGAGGC AGTGAGGGTT    300

TTACTGGTGC CGGTAATATG GGCAGCGTTA TCCGATTTCA ATGGATGCT GGCCGGCAGA     360

CAAATCTTTA TCAACATTCA AATTCAGATC                                    390
```

(2) INFORMATION FOR SEQ ID NO: 5:

(i) SEQUENCE CHARACTERISTICS:
        (A) LENGTH: 177 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 5:

```
GATCAGATTG GTGAAGACGG TATTACCGTC AATGTTGCAG GCCGTTCGGG ATATACGGCG     60

AAAATCGACG TGTCTCCGAG TACCGATTTG GCGGTTTATG GCCATATTGA AGTTGTACGG    120

GGTGCAACGG GGTTGACCCA ATCCAATTCA GAGCCGGGTG GAACCGTCAA TTTGATC      177
```

(2) INFORMATION FOR SEQ ID NO: 6:

(i) SEQUENCE CHARACTERISTICS:
        (A) LENGTH: 341 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 6:

```
GATCAATGAT GCTACTATTC AAGCGGGCAG TTCCGTGTAC AGCTCCACCA AAGGCGATAC     60

TGAATTGGGT GAAAATACCC GTATTATTGC TGAAAACGTA ACCGTATTAT CTAACGGTAG    120

TATTGGCAGT GCTGCTGTAA TTGAGGCTAA AGACACTGCA CACATTGAAT CGGGCAAACC    180

GCTTTCTTTA GAAACCTCGA CCGTTGCCTC CAACATCCGT TGAACAACG GTAACATTAA     240

AGGCGGAAAG CAGCTTGCTT TACTGGCAGA CGATAACATT ACTGCCAAAA CTACCAATCT    300

GAATACTCCC GGCAATCTGT ATGTTCATAC AGGTAAAGAT C                      341
```

(2) INFORMATION FOR SEQ ID NO: 7:

(i) SEQUENCE CHARACTERISTICS:
        (A) LENGTH: 164 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 7:

```
GATCCAACTG TTTGATTTTA CTGGCTGCTT CTCCATGCGC GGTATTGACC AAAGCCGCAA     60

GGATATTCGC TTCCAGATTG TCTTTCAGGC TGCCGCCGTT GACAGCGGTA TTAATCAGTG    120

CGGCACTGCC CGCATTGGCT AGGTTGACGG TCAGGTTGTT GATC                     164

(2) INFORMATION FOR SEQ ID NO: 8:

(i) SEQUENCE CHARACTERISTICS:
        (A) LENGTH: 219 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
         (A) ORGANISM: Neisseria meningitidis
         (B) STRAIN: Z2491

(xi) SEQUENCE DESCRIPTION: SEQ ID NO: 8:

GATCAATCAC ACATCTTGTC ATTTTTTCGA TTCCTTCATT TCGGTTTCTA ATGTTTCAAT     60

TCTTGCGGCC ATTTCCTGAA TGGCTTTAGT CAAAACGGGG ATGAACGCTT CGTATTCGAC    120

GGTGTAGGTA TCGTTTGTTT TATTTACCAT CGGCAATCGA CCATATTCAT CTTCCAGCGC    180

AGCAATGTCC TGGGCAATAA ACCAATGCCG CAACCGATC                           219

(2) INFORMATION FOR SEQ ID NO: 9:

(i) SEQUENCE CHARACTERISTICS:
        (A) LENGTH: 356 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
         (A) ORGANISM: Neisseria meningitidis
         (B) STRAIN: Z2491

(xi) SEQUENCE DESCRIPTION: SEQ ID NO: 9:

GATCTTGGGT AAGCCCCCAA CCTGCATAGA AAGGCAGGCC GTAGCAGCTG ACTTTTTTGC     60

CGCGCAACAA GGCTTCAAAA CCGGTCAGCG AAGTCATGGT ATGTATTTCG TCTGCGTATT    120

GGAGACAGGT CAGGATGTCG GCTTGTTCGG CGGTTTGGTC GGCATATCGT GCAGCATCAT    180

CAGGGGAAAT ATGGCCGATG CGGTTACCGC TGACTACATC GGGATGCGGT TTGTAGATGA    240

TATAGGCATT GGGGTTTCGT TCGCGTACGG TACGGAGCAA ATCCAGATTG CGGTAGATTT    300

GGGGCGAACC GTAGCGGATA GACGCATCAT CTTCAACCTG GCCGGGAACG AGGATC        356

(2) INFORMATION FOR SEQ ID NO: 10:

(i) SEQUENCE CHARACTERISTICS:
        (A) LENGTH: 210 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
         (A) ORGANISM: Neisseria meningitidis
         (B) STRAIN: Z2491

(xi) SEQUENCE DESCRIPTION: SEQ ID NO: 10:

GATCCGCTTT CAGTTTCCGT ACCGGTGGCA TCAGTCAAGT CCGTTTTGTG CACCAAACCG     60
```

```
CGTCCATATG AAACATAAAA CAAATCGCTT AAGCCCAAAG GGTTATCGAA CGATAAAGCG    120

ACATTTCCTT GATATTTGCC GGTCGTTTTG CCGCCCGCAT CATCTATACC GATACTGAAC    180

CGTATGGGTT TATTCTGCTG CCATTTGATC                                    210
```

(2) INFORMATION FOR SEQ ID NO: 11:

(i) SEQUENCE CHARACTERISTICS:
        (A) LENGTH: 259 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 11:

```
GATCCCGAAA CGCAATTGGT CGAAAGCTAT ATGCTGAACG ATGTGTTGCG GTTTTGGGAC     60

AGCGCAGGTT TGGGCGATGG GAAAGAAGCC GACCGCGCCC ATCGGCAAAA ACTGATTGAT    120

GTCCTGTCTA AAACCTATAC TCATTCGGAT GGGCAGTGGG GCTGGATAGA TTTGGTGTTC    180

GTTATCCTTG ACGGCAGCTC CCGCGATTTG GGTACGGCCT ATGATTTGTT GAGGGATGTT    240

ATCCTTAAAA TGATTGATC                                                 259
```

(2) INFORMATION FOR SEQ ID NO: 12:

(i) SEQUENCE CHARACTERISTICS:
        (A) LENGTH: 436 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 12:

```
GATCAAATGG ATGATTTATA TAGAATTTTC TTTTACGACT GCGTGCCGTT TGAAAAGAAA     60

ATGCACAATC CCGTATCTCA TCGTGCCATA GATTTTTCAA AGACTCCGGA AGCCATATTT    120

CGTTGCAATC TGCATACCGA ATTGAAGAAG AAGCGTAAAT TAGCGTTACG TTTAGGCAAG    180

CTGTCGGACA ATACAGCATG GATATTAAAA CCCCAAGTCA TGAAAATCT TCTGAAAAAC    240

CCGTCAACTC AAATTACGGA AAACGATGTC GTGCTCGATG TTAAACAAAA AGGTGTAGAT    300

ATGCGTATAG GCTTGGATAT TTCATCTATT ACCTTAAAAA AACAAGCCGA TAAAATCATC    360

TTGTTTTCTG GTGATTCCGA TTTTGTCCCA GCAGCCAAAT TAGCCAGACG GGAAGGTATC    420

GATTTTATTC TTGATC                                                    436
```

(2) INFORMATION FOR SEQ ID NO: 13:

(i) SEQUENCE CHARACTERISTICS:
        (A) LENGTH: 363 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:

(A) ORGANISM: Neisseria meningitidis
        (B) STRAIN: Z2491

(xi) SEQUENCE DESCRIPTION: SEQ ID NO: 13:

GATCGTTTTA CGTCGCAATC GAGCTTTGTG GTGCGCTCGC CTAAAAGCCA ATCTTCTCTC      60

AATGGCCTGG GTGCCATTTT GCAGGGCACA GGTTTTGCCC GTGCGCAAGA CGATATTTAT     120

ACCGTGCAGG AATATATGCA GTCGCGTTCG GCTTTGGATG CGTTGCGTAA GAAAATGCCC     180

ATTCGCGATT TTTATGAAAA AGAAGGCGAT ATTTTCAGCC GTTTTAATGG TTTTGGCCTG     240

CGTGGCGAGG ATGAGGCGTT TTATCAATAC TACCGTGATA AGGTATCCAT CCATTTTGAC     300

TCTGTCTCAG GCATTTCCAA TTTGAGCGTT ACATCGTTTA ATGCCGGTGA ATCTCAAAAG     360

ATC                                                                 363

(2) INFORMATION FOR SEQ ID NO: 14:

(i) SEQUENCE CHARACTERISTICS:
        (A) LENGTH: 314 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 14:

GATCTTGCGT CATTTATATC TTCACCGATA TTGCAATTAC CGCCGTTCCA GTTGAAATAA      60

CAACGACTAA AATTGTAGTT CCTAAAAGAA TCATTCCTAT TCTTGCGTAC CATTTCCCAA     120

TAATTGCGCC CGACAATTTC CATTTAATGC TCCATCAGTT CTTTTACTTC CGGAAATCTG     180

CTGTAATCTG ACATAAGACG CATAATTGAA CTATCAACGC CGTAACAGCC ATAGGTTTTA     240

ATACCGTTTT CGGCGTGTTC CCAAATGCAA TTACTGTATT CGTAGCCTTT TACAAATTTA     300

TCGGTTTCGG GATC                                                     314

(2) INFORMATION FOR SEQ ID NO: 15:

(i) SEQUENCE CHARACTERISTICS:
        (A) LENGTH: 256 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 15:

GATCATACGA ATCTACCCTA AAATACCCCG TCGCCGATTT AGGATTGGCT ACATAAAGCT      60

CATTATAAGG GTATTTTGAT GACATGATAC GGTTAAATTC ATTGCCGTTG TTTATCCTGA     120

TTCTATAAAT TGGTTCAACA GCAAAGCCTC TGGATTCCCT TAATTGATTA TAATATTGCC     180

TGTATGTTTG TACATCATGT CTTGTCCACG GCTCTCCAGG AGTCCTCAGA ATAGCAATCC     240

CGTTAAATTT CGGATC                                                   256

(2) INFORMATION FOR SEQ ID NO: 16:

(i) SEQUENCE CHARACTERISTICS:

(A) LENGTH: 235 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 16:

GATCCACGCC TGTGCCTACC TTGGCTTTTT GTTCGCCAAA CAAGGCATTT AAGGTTGAGG      60

ACTTGCCGAC ACCTGTCGCA CCGACAAGCA AGACATCCAA ATGACGGAAA CCGGCTGCTG     120

TGACTTTTTG CCCGATTTCA GAAATACGGT AACGATGCAT ATGCGCTCCT ACCAGCCAAA     180

AAAAGAAGCA ACCGTGCTAA TCGCCCCTCC AATCGCTTTT GCAGCACCGC CGATC          235

(2) INFORMATION FOR SEQ ID NO: 17:

(i) SEQUENCE CHARACTERISTICS:
        (A) LENGTH: 259 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 17:

GATCCAACGG GCATCGCTGT CCTTACTCGG TGTGGTTTGA CCGCTGATTT GTCCTTCTTC      60

GTCAACTTCT ATGGCCTGAC GCTGTTTGCT GCCGGCGGTC TGGATAATGG TGGCATCAAC     120

GACGGCGGCG GATGCTTTCT CTATTTTTAG GCCTTTTTCG GTCAGTTGGC AGTTAATCAG     180

TTTGAGTAAT TCGGACAGGG TGTCGTCTTG CGCCAGCCAG TTGCGGTAGC GGCATAAGGT     240

ACTGTAATCG GGGATGATC                                                  259

(2) INFORMATION FOR SEQ ID NO: 18:

(i) SEQUENCE CHARACTERISTICS:
        (A) LENGTH: 201 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 18:

GATCTGTGCC GTTGATTTTA TCTTTCAGAT GCAGCATCGA ATATCGGAAA GCCAAATCAG      60

CAATTCTTTT TGCATCGTGT GGATTTTGAG ACGGGCCTAA TGACCGTACC CGCTTAATAA     120

AAAATGCACC GTCAATCAAA ATGGCGGTTT TCATATTGCT TCCCCTATAT TTGTCAAAGA     180

TATAAAAAAG CCCTTGGGAT C                                               201

(2) INFORMATION FOR SEQ ID NO: 19:

(i) SEQUENCE CHARACTERISTICS:
        (A) LENGTH: 334 base pairs
        (B) TYPE: nucleotide

```
        (C) STRANDEDNESS: single
        (D) TOPOLOGY: linear (ii) MOLECULE TYPE: DNA (genomic)

(vi) ORIGINAL SOURCE:
         (A) ORGANISM: Neisseria meningitidis
         (B) STRAIN: Z2491

(xi) SEQUENCE DESCRIPTION: SEQ ID NO: 19:

AATTCAAAGG AGGCATTTGT TGCAAGAAAA GTACAAAGTG ATTTGCAAAA AGCATTGAAT      60

GCTAGCAACT ATAACAAGCA GCAATATGCA AGACGTGCGG CAACAGCGTT AGAGAATGCT     120

TCAAAATCAA AAGTTATGGC AGCGAATTCT TTTTGATCTA TCTTGTGCGA ACGGGTCAAA     180

TATTCTTCGT ACATTGAGTT AATCGTACCA ATCGCCCTAA CCACATTTTC ATCAGAAAAT     240

ATGGAAATAA TAGCATCCCT ATACGCACCT AGTGTAATAT TGTTTCTATT ATTAGTTATA     300

GCATTATTCG AATACATAAT AGCACCTCCA AATT                                 334

(2) INFORMATION FOR SEQ ID NO: 20:

(i) SEQUENCE CHARACTERISTICS:
        (A) LENGTH: 238 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
         (A) ORGANISM: Neisseria meningitidis
         (B) STRAIN: Z2491

(xi) SEQUENCE DESCRIPTION: SEQ ID NO: 20:

AATTCCTGCG CACCTTTGCC GATGGGGAGA TAATCGCCTT TTTGCAGCAT TCTGCCCTGA      60

TGGCCGCCGA AACCGGCTTT CAGGTCGGTA CTTCTCGAAC CCATCACTTC CGGCACATCA     120

AATCCGCCCG CCACGCACAC ATAGCCGTAC ATGCCCTGCA CGGCACGCAC CAGTTTCAAG     180

GTCTGCCCTT TGCGGGCGGT ATAACGCCAA TACGAATAGA CCGGTTCGCC GTCCAATT       238

(2) INFORMATION FOR SEQ ID NO: 21:

(i) SEQUENCE CHARACTERISTICS:
        (A) LENGTH: 249 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
         (A) ORGANISM: Neisseria meningitidis
         (B) STRAIN: Z2491

(xi) SEQUENCE DESCRIPTION: SEQ ID NO: 21:

AATTGGGCGA GATGCTGCCG GAAACGGATT TAAAACAGAT TGCGGCGGCA GTGTTGAAGA      60

CGAACGATGA GGCGGCATTG CAGAAGGTGG TGAAAACGGC CAAAGGCAAT GCGCGGAAAC     120

TGTCGAAGCT GCTGCTGATT GTGGACTATT TGTTGCAGGT TAACCCTGAT GTTGATTTGG     180

ATGATGATGT AATCGAACAC GCGGAAACCT ATTTAATCCA CTAAACCTTT GACAGATAAG     240

GCAATAATT                                                            249

(2) INFORMATION FOR SEQ ID NO: 22:

(i) SEQUENCE CHARACTERISTICS:
```

(A) LENGTH: 212 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 22:

```
AATTTATGTA CGGTTTTGCC GTTTGCAGTC AGCCAGTCGG CAAGGCGCAG AAAAAAATCG        60

CCGACAGGGC CTTGAAGCAG CAGGATATTT TCTGCGCTTT CAAGCAGGTT TTGCAGGTTA       120

TTTTTGAGGA CGGTCTGTTT CATGTTGCAA TGTGGTTTTG TTTTTTATGT AATAGTTTTA       180

GGTTGAACTT TCAAGCATAC GCCAAGAGAA TT                                     212
```

(2) INFORMATION FOR SEQ ID NO: 23:

(i) SEQUENCE CHARACTERISTICS:
        (A) LENGTH: 227 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 23:

```
AATTCAGTGC CTGCGTCATA TCACGGCTAC CTTGTGGTTC AGGGTTACTG TATCGCCCGC        60

GGCATCGACG GCTTCAATAT GCAGCTTCAG CCAGCCGTGC TGCGGGGCGG ATGCGGTTAC       120

TTGGATGGAT TGGGCGCGTT TGGACTGAAT CACGGGCTGC AAGGCTTGCT CGGCGTACTG       180

TTTGGCCAGT ACTTCGATGC GCTTTAAATG CTTTTGGCGG CGCAATT                    227
```

(2) INFORMATION FOR SEQ ID NO: 24:

(i) SEQUENCE CHARACTERISTICS:
        (A) LENGTH: 167 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 24:

```
GATCCAGGAC TCAAAAACCG ATTTCCTAAT AGAGTGTCTA ATATCCCAAT CTTTTTTACC        60

CCCTCTGCTG TAGAATTGAT AGAGAAAGTT TGTCTATCTT TTTCATATAC CCATGCCTTC       120

TTTTTATCAT TGTAGCTAAC ATAACCGCCA AACAATGCTT CTAGATC                    167
```

(2) INFORMATION FOR SEQ ID NO: 25:

(i) SEQUENCE CHARACTERISTICS:
        (A) LENGTH: 251 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 25:

AATTCTTGCG GCCATTTCCT GAATGGCTTT AGTCAAAACG GGGATGAACG TTTCGTATTC    60

GACGGTGTAG GTATCGTTTG TTTTATTTAC CATCGGCAAT CGACCATATT CATCTTCCAG   120

CGCAGCAATG TCCTGGGCAA TAAACCAATG CCGCAACCGA TCTTCTTTAT GACTGCCGTC   180

CTTGATTGGA TTCGCCCACC ATTCGCGGAC TTTGTCCGCT CGTTCATCTG CCGGCAAGTC   240

TTTGAATAAT T                                                       251

(2) INFORMATION FOR SEQ ID NO: 26:

(i) SEQUENCE CHARACTERISTICS:
        (A) LENGTH: 207 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 26:

AATTCCCGAC TATCGCGGAT GCGTAGTTTT TGCCGGTGGG CAAGAGCAGG TGTGGGATAA    60

GTTAGGTGAT TTGCCCGATG GCGTCAGCCT GACCCCGCCT GAATCGGTAA ATATTGACGG   120

CTTAAAATCC GTAAAACTCG TCGCATTAAA TGCTGCCGCT CAGGCTTTTA TTAACAAGCA   180

CGCCGGTATC GACAGCGTAC CTGAATT                                      207

(2) INFORMATION FOR SEQ ID NO: 27:

(i) SEQUENCE CHARACTERISTICS:
        (A) LENGTH: 379 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 27:

AATTGTTTGG GAATAATCCA AACAAACAGC ATCAGGATAG CGGCGGCGGT CAGGCTGCCT    60

GAAAGGATTT TGCCGGGGTT TTTTGTAGGC AAAGCGGACG AGAAACCAAA GCAACAGCAG   120

CATGGTGTCC CAATAGCCGA TTGAGAATAG GATGGCCAAA CCTTCTAGGA AATGGCGTAA   180

ATCGTTTGTG GTAACCATGG GTAGTTCCTG TGGTTAAATG TGCAGGCTGC TTTTTGCCGA   240

ACCTTGCCGC ATCTCAAAAG CAGCCTGCGC TTCAGCGTTG CGTTACGCAG TAAAATAATG   300

AATATTTGTA ACGGCTTGGG TATTTTTTGT CAATATTCCC GCCCTTCCCT TAACAGCTGC   360

CGCGCTTTCC GTTAAAATT                                               379

(2) INFORMATION FOR SEQ ID NO: 28:

(i) SEQUENCE CHARACTERISTICS:
        (A) LENGTH: 274 base pairs
        (B) TYPE: nucleotide (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 28:

```
AATTCGCCGA AATCAGGCTG CTGCTCGATA ATCGGCGCGG CCGATTGGCG TTGTGCCTCG    60

ATTAAATCCA TCTTGTCTTG CAGACGTTTG GCCTGGCCTT TGCGGCGGCG TTCGGCCAGT   120

TGTTCCATCC GCGTTTCCGC AAATGCCGCC CGTTTGTTGC CGTTGAATAC CGCTTTGCAA   180

ATCACCTTGC CCTGCATATC CTTCACAATC ACATGGTCGG CATCGTGGAT GTCGTAAGCC   240

ACCCGTACCT TCTGACCGCT GTAATCCAGC AATT                               274
```

(2) INFORMATION FOR SEQ ID NO: 29:

(i) SEQUENCE CHARACTERISTICS:
        (A) LENGTH: 263 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 29:

```
AATTCCGTTC TTATTGGGCT TTTTCCATCC ATCGGGTATG CCTGAAGGGA ACGCAAACCC    60

TGCCACTTGC CCATCGCTCC ATTCCCGCAT TAGCGCGTCT GACGGCAAGT GTTCTCGCGC   120

CCAATCAAGC CACGCCTGCC GCATTGCGGC CTTGTCCTGC TGAAAACTTC GCAGTGCTTT   180

TGCAACCGGC CCATCATTAA CTTCAATCAA ATAAATCATT ATATTTGCGT TCATTTTTCC   240

TACACCTTCG CCACATCCAA ATT                                           263
```

(2) INFORMATION FOR SEQ ID NO: 30:

(i) SEQUENCE CHARACTERISTICS:
        (A) LENGTH: 316 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 30:

```
AATTGTTCAA GAAAAAGTC GGCACGGCGC GGCAACGGGG AAAATGCGTT GACGCCGTCT    60

TTTTCTAAGG TGATGTAGTA GGGGCGGAAA TAGCCTTCTT CAAACGCCCA GAAACTGGCT   120

TGGTTTTCGT TTGCAATGCG TTTTGCAATG ACGTGATAAG GGCGTGTGTC GCCAAAGCAG   180

ACAACGGCCT GGATGTGATG TTGAGTGATG TATTCTTGCA AAAACTCAGG AAAGGCGTCG   240

TAGTTGTCGT TAAAAACAAC GGTATGCGCT TGAGTGGGCG GATAAAAATA GTCGTCGCCT   300

GCATTAAAGT TGAATT                                                   316
```

(2) INFORMATION FOR SEQ ID NO: 31:

(i) SEQUENCE CHARACTERISTICS:
        (A) LENGTH: 324 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 31:

```
AATTCAATCA ACGGAAAACA CATCAGCATC AAAAACAACG GTGGTAATGC CGACTTAAAA      60

AACCTTAACG TCCATGCCAA AAGCGGGGCA TTGAACATTC ATTCCGACCG GGCATTGAGC     120

ATAGAAAATA CCAAGCTGGA GTCTACCCAT AATACGCATC TTAATGCACA ACACGAGCGG     180

GTAACGCTCA ACCAAGTAGA TGCCTACGCA CACCGTCATC TAAGCATTAC CGGCAGCCAG     240

ATTTGGCAAA ACGACAAACT GCCTTCTGCC AACAAGCTGG TGGCTAACGG TGTATTGGCA     300

CTCAATGCGC GCTATTCCCA AATT                                            324
```

(2) INFORMATION FOR SEQ ID NO: 32:

(i) SEQUENCE CHARACTERISTICS:
        (A) LENGTH: 230 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 32:

```
AATTATGCAA AAAAACGCAA CGCCGAAAAA CTGGCACCGC GCGGATATTG TTGCTGCTTT      60

GAAAAGAAA GGCTGGTCAC TTCGAGCACT TCAATAGAA GCGGGGTTGT CGCCGAATAC      120

GCTTAGAAGC GCACTGGCCG CCCCTTATCT TAAGGGAGAA AGGATTATTG CCGCTGCAAT     180

CGGAGTGGAA CCGGAAGAGA TTTGGTCCGA ACGGTATGCA GATCGGAATT               230
```

(2) INFORMATION FOR SEQ ID NO: 33:

(i) SEQUENCE CHARACTERISTICS:
        (A) LENGTH: 249 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 33:

```
AATTTAATCG GTGGAATGCC TGTTCAACCG CACCAATCCC GCTGAATACG GTTGCTAATC      60

TAATATGTGA ATCAGGTTTA AGAAAAGTTT TAGATTTCCA ACCTTGTTGA CTGGGAAAGA    120

GCAAAGTTTT TTGTAATCGA GTATCGTGTG TCTGTGCCAT TGTCGAAATA GTCATACTTA    180

TATCGTTCTG TTTATCTTAT CAATATGAAA ACTACATCGT TGATTGCCCT GACAATGCCT    240

TGGTCAATT                                                             249
```

(2) INFORMATION FOR SEQ ID NO: 34:

(i) SEQUENCE CHARACTERISTICS:
        (A) LENGTH: 343 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 34:

```
AATTCTTGTC CCGGAGTCCA ACGTATATTT ACCCTCCTGC GAGCTAAAAG ACTATTATTC      60

TCCACTGCCA CAGTAGCCGC ATTCACCGCC GTATTCACAT CCCCTTTAAC CAATGCCACT     120

GCGCTGCCTG CGATAATCTG CGAGTAGGCT ATGACTTTTT GGCGTTCTTG GGGTGACAGT     180

TTGCCTACAT CGCGTCCGTC CAACAGGGTT TCTCCCACCA TCTCGCCGAC TGCCGCGCCG     240

ATTGCGCCGT CCCGACATTT GCCTTTATTT GCTACCGCCG ATGCACAGCC TGCTACGGCA     300

TGGGCTATCT TGTGGGCAAT GTAGTCTTCG CTGAGATTAA ATT                      343
```

(2) INFORMATION FOR SEQ ID NO: 35:

(i) SEQUENCE CHARACTERISTICS:
        (A) LENGTH: 184 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 35:

```
AATTCTTCAA ACATCGTTTC GATAATCGGG TCGGTGTACA CACTGATGCG GTCGCCCGCA      60

CGGCTTTGAC CGGCTCGGAA AATATAGGCG GTGGCTTTGC CGTCGGCGAT GTCGACGCAC     120

CAACGCCAGA TGGCGTCTTC GGTATTCAAA CAATCACCCG CACAGCTTTC ACCTGCGCGG     180

AATT                                                                  184
```

(2) INFORMATION FOR SEQ ID NO: 36:

(i) SEQUENCE CHARACTERISTICS:
        (A) LENGTH: 15620 base pairs
        (B) TYPE: nucleotide
        (C) STRANDEDNESS: single
        (D) TOPOLOGY: linear (ii) MOLECULE TYPE: DNA (genomic)

(vi) ORIGINAL SOURCE:
        (A) ORGANISM: Neisseria meningitidis
        (B) STRAIN: Z2491

(xi) SEQUENCE DESCRIPTION: SEQ ID NO: 36:

```
TATGCTCAAT CTCATTTTCA AAATGCAAAA CTTTTCTGAT TTTTCCTACT TTTTGCTCAA      60

TATTAGGAAG GTTTTAGGCA ATTGAAAATT TTTTGGCGCA TTTTTATGCG TCAAATTTCG     120

TTAACAGACT ATTTTTGCAA AGGTCTCCGT CTGTAAAAGC AAGGATAGGG CATCTGCCCT     180

TTTGATTGTT TGATTAACGA TACAAGGAGT TTCAAAATGA GAGTTTTATA GTGGATTAAC     240
```

```
AAAAACCAGT ACAGCGTTGC CTCGCCTTGC CGTACTATTT GTACTGTCTG CGGCTTCGTC    300

GCCTTGTCCT GATTTAAATT TAATCCACTA TATGTGTTCA TGAAATGACT TGGGTCGGAG    360

GCTCAGGTAA TGCGCAACAA AGTTCATATT ATTGCGAAAT TTGCGAATCT GCAGGGCTTA    420

ACGATACGGG AAATCCTGAT AAATCTTTAG GATTGCCAAA CAATACGTTC AGTAATCCGC    480

CTGGTTGGGG AGCTACAATC GGAGCTTTAG CAGGTAGCCG CATAGGTATG CCTGAATTTG    540

GTACGTTTGC GAGCCATGCC ATTGAAAATT TCGACTGGTC ATGGTATCGA CGTTATAGGG    600

AAATTGCCGA AACGATTGAA CGAGAATATT CAGGCGGTTT GCCTTAATAG TTGAGGAGGT    660

CATGATGTTT GCCAAACATT ATCAATTCAT CGCACTCGGC ATCATGCTGC TTCTTTATAT    720

GTTGATTCTC TATACGACCG ATTTTTCCAA TCTGACGTAT TGGATGCTGT TTTTTATCTG    780

TTTTATTACA GGAAAAATAT TAGCTCGTTT GTTAGAGAAA AGCTTTAAAT AAAATAGCAG    840

CTAGTCGCAA AAGGTCGTCT GAAACCTTTT CAGGCGGCCT TTCTAAAATA CATCCAACTT    900

CCTAATCCCT ATTTTTCAAA AAGGAAATCT ATGCCCCATC TGCAAAACCT GTCTTTGGGC    960

TTAAAGAAAA AGCTGCCTGT TATCCTGCAA ACAGAAATAT CAGAATGCGG CTTGGCATGT   1020

CTGGCGGCTG TGGCGGGATT TCATGGTTTC CATACGAATT TACGCGCACT GCGTTCAAAA   1080

TACTGTCCGA GACCTTTGCA AAATTCCCCA AAATCCCCTA AATGTCTTGG TGGGAATTTT   1140

GGGGAATTTT GCAAAGGTCT CATTCTATAA CTGTAAATAC TTTTAAATTT ATGACAAAAT   1200

AGTAAATATT GCTAAAATAA TATTGATGTC ATGAAATTTT TTCCTGCTCC ATGTCTGTTG   1260

GTTATCCTGG CTGTCATACC CCTTAAAACC TTAGCTGCCG ATGAAAACGA TGCAGAACTT   1320

ATCCGTTCCA TGCAGCGTCA GCAGCACATA GATGCTGAAT TGTTAACTGA TGCAAATGTC   1380

CGTTTCGAGC AACCATTGGA GAAGAACAAT TATGTCCTGA GTGAAGATGA AACACCGTGT   1440

ACTCGGGTAA ATTACATTAG TTTAGATGAT AAGACGGCGC GCAAATTTTC TTTTCTTCCT   1500

TCTGTGCTCA TGAAAGAAAC AGCTTTTAAA ACTGGGATGT GTTTAGGTTC CAATAATTTG   1560

AGCAGGCTAC AAAAAGCCGC GCAACAGATA CTGATTGTGC GTGGCTACCT CACTTCCCAA   1620

GCTATTATCC AACCACAGAA TATGGATTCG GGAATTCTGA AATTACGGGT ATCAGCAGGC   1680

GAAATAGGGG ATATCCGCTA TGAAGAAAAA CGGGATGGGA AGTCTGCCGA GGGCAGTATT   1740

AGTGCATTCA ATAACAAATT TCCCTTATAT AGGAACAAAA TTCTCAATCT TCGCGATGTA   1800

GAGCAGGGCT TGGAAAACCT GCGTCGTTTG CCGAGTGTTA AAACAGATAT TCAGATTATA   1860

CCGTCCGAAG AAGAAGGCAA AAGCGATTTA CAGATCAAAT GGCAGCAGAA TAAACCCATA   1920

CGGTTCAGTA TCGGTATAGA TGATGCGGGC GGCAAAACGA CCGGCAAATA TCAAGGAAAT   1980

GTCGCTTTAT CGTTCGATAA CCCTTTGGGC TTAAGCGATT TGTTTTATGT TTCATATGGA   2040

CGCGGTTTGG TGCACAAAAC GGACTTGACT GATGCCACCG GTACGGAAAC TGAAAGCGGA   2100

TCCAGAAGTT ACAGCGTGCA TTATTCGGTG CCCGTAAAAA AATGGCTGTT TTCTTTTAAT   2160

CACAATGGAC ATCGTTACCA CGAAGCAACC GAAGGCTATT CCGTCAATTA CGATTACAAC   2220

GGCAAACAAT ATCAGAGCAG CCTGGCCGCC GAGCGCATGC TTTGGCGTAA CAGGTTTCAT   2280

AAAACTTCAG TCGGAATGAA ATTATGGACA CGCCAAACCT ATAAATACAT CGACGATGCC   2340

GAAATCGAAG TGCAACGCCG CCGCTCTGCA GGCTGGGAAG CCGAATTGCG CCACCGTGCT   2400

TACCTCAACC GTTGGCAGCT TGACGGCAAG TTGTCTTACA AACGCGGGAC CGGCATGCGC   2460

CAAAGTATGC CCGCACCTGA AGAAAACGGC GGCGGTACTA TTCCAGGCAC ATCCCGTATG   2520

AAAATCATAA CCGCCGGATT GGATGCAGCG GCCCCGTTTA TGTTGGGCAA ACAGCAGTTT   2580

TTCTACGCAA CCGCCATTCA AGCTCAATGG AACAAAACGC CTTTGGTTGC CCAAGACAAG   2640
```

```
TTGTCTATCG GCAGCCGCTA CACCGTTCGC GGATTTGATG GGGAGCAGAG TCTTTTCGGA    2700

GAGCGAGGTT TCTACTGGCA GAATACTTTA ACTTGGTATT TTCATCCGAA CCATCAGTTC    2760

TATCTCGGTG CGGACTATGG CCGCGTATCT GGCGAAAGTG CACAATATGT ATCGGGCAAG    2820

CAGCTGATGG GTGCAGTGGT CGGCTTCAGA GGAGGGCATA AGTAGGCGG TATGTTTGCT     2880

TATGATCTGT TTGCCGGCAA GCCGCTTCAT AAACCCAAAG GCTTTCAGAC GACCAACACC    2940

GTTTACGGCT TCAACTTGAA TTACAGTTTC TAACCTCTGA ATTTTTTAC TGATATTTAG     3000

ACGGTCTTTC CTTATCCTCA GACTGTCAAA CTTTACCTAC GTACTGGCG CGCAGTACGT     3060

TCATCTTCAA AATGGAATAG ACATGAATAA AGGTTTACAT CGCATTATCT TTAGTAAAAA    3120

GCACAGCACC ATGGTTGCAG TAGCCGAAAC TGCCAACAGC CAGGGCAAAG GTAAACAGGC    3180

AGGCAGTTCG GTTTCTGTTT CACTGAAAAC TTCAGGCGAC CTTTGCGGCA AACTCAAAAC    3240

CACCCTTAAA ACCTTGGTCT GCTCTTTGGT TTCCCTGAGT ATGGTATTGC CTGCCCATGC    3300

CCAAATTACC ACCGACAAAT CAGCACCTAA AAACCAGCAG GTCGTTATCC TTAAAACCAA    3360

CACTGGTGCC CCCTTGGTGA ATATCCAAAC TCCGAATGGA CGCGGATTGA GCCACAACCG    3420

CTATACGCAG TTTGATGTTG ACAACAAAGG GGCAGTGTTA AACAACGACC GTAACAATAA    3480

TCCGTTTCTG GTCAAAGGCA GTGCGCAATT GATTTTGAAC GAGGTACGCG GTACGGCTAG    3540

CAAACTCAAC GGCATCGTTA CCGTAGGCGG TCAAAAGGCC GACGTGATTA TTGCCAACCC    3600

CAACGGCATT ACCGTTAATG GCGGCGGCTT TAAAAATGTC GGTCGGGGCA TCTTAACTAT    3660

CGGTGCGCCC CAAATCGGCA AAGACGGTGC ACTGACAGGA TTTGATGTGC GTCAAGGCAC    3720

ATTGACCGTA GGAGCAGCAG GTTGGAATGA TAAAGGCGGA GCCGACTACA CCGGGGTACT    3780

TGCTCGTGCA GTTGCTTTGC AGGGGAAATT ACAGGGTAAA AACCTGGCGG TTTCTACCGG    3840

TCCTCAGAAA GTAGATTACG CCAGCGGCGA AATCAGTGCA GGTACGGCAG CGGGTACGAA    3900

ACCGACTATT GCCCTTGATA CTGCCGCACT GGGCGGTATG TACGCCGACA GCATCACACT    3960

GATTGCCAAT GAAAAGGCG TAGGCGTCAA AAATGCCGGC ACACTCGAAG CGGCCAAGCA     4020

ATTGATTGTG ACTTCGTCAG GCCGCATTGA AACAGCGGC CGCATCGCCA CCACTGCCGA     4080

CGGCACCGAA GCTTCACCGA CTTATCTCTC CATCGAAACC ACCGAAAAAG GAGCGGCAGG    4140

CACATTTATC TCCAATGGTG GTCGGATCGA GAGCAAAGGC TTATTGGTTA TTGAGACGGG    4200

AGAAGATATC AGCTTGCGTA ACGGAGCCGT GGTGCAGAAT AACGGCAGTC GCCCAGCTAC    4260

CACGGTATTA AATGCTGGTC ATAAATTTGGT GATTGAGAGT AAAACTAATG TGAACAATGC   4320

CAAAGGCTCG GCTAATCTGT CGGCCGGCGG TCGTACTACG ATCAATGATG CTACTATTCA    4380

AGCGGGCAGT TCCGTGTACA GCTCCACCAA AGGCGATACT GAATTGGGTG AAAATACCCG    4440

TATTATTGCT GAAAACGTAA CCGTATTATC TAACGGTAGT ATTGGCAGTG CTGCTGTAAT    4500

TGAGGCTAAA GACACTGCAC ACATTGAATC GGGCAAACCG CTTTCTTTAG AAACCTCGAC    4560

CGTTGCCTCC AACATCCGTT TGAACAACGG TAACATTAAA GGCGGAAAGC AGCTTGCTTT    4620

ACTGGCAGAC GATAACATTA CTGCCAAAAC TACCAATCTG AATACTCCCG GCAATCTGTA    4680

TGTTCATACA GGTAAAGATC TGAATTTGAA TGTTGATAAA GATTTGTCTG CCGCCAGCAT    4740

CCATTTGAAA TCGGATAACG CTGCCCATAT TACCGGCACC AGTAAAACCC TCACTGCCTC    4800

AAAAGACATG GGTGTGGAGG CAGGCTTGCT GAATGTTACC AATACCAATC TGCGTACCAA    4860

CTCGGGTAAT CTGCACATTC AGGCAGCCAA AGGCAATATT CAGCTTCGCA ATACCAAGCT    4920

GAACGCAGCC AAGGCTCTCG AAACCACCGC ATTGCAGGGC AATATCGTTT CAGACGGCCT    4980
```

```
TCATGCTGTT TCTGCAGACG GTCATGTATC CTTATTGGCC AACGGTAATG CCGACTTTAC    5040

CGGTCACAAT ACCCTGACAG CCAAGGCCGA TGTCAATGCA GGATCGGTTG GTAAAGGCCG    5100

TCTGAAAGCA GACAATACCA ATATCACTTC ATCTTCAGGA GATATTACGT TGGTTGCCGG    5160

CAACGGTATT CAGCTTGGTG ACGGAAAACA ACGCAATTCA ATCAACGGAA AACACATCAG    5220

CATCAAAAAC AACGGTGGTA ATGCCGACTT AAAAACCTT AACGTCCATG CCAAAAGCGG     5280

GGCATTGAAC ATTCATTCCG ACCGGGCATT GAGCATAGAA ATACCAAGC TGGAGTCTAC     5340

CCATAATACG CATCTTAATG CACAACACGA GCGGGTAACG CTCAACCAAG TAGATGCCTA    5400

CGCACACCGT CATCTAAGCA TTACCGGCAG CCAGATTTGG CAAAACGACA AACTGCCTTC    5460

TGCCAACAAG CTGGTGGCTA ACGGTGTATT GGCACTCAAT GCGCGCTATT CCCAAATTGC    5520

CGACAACACC ACGCTGAGAG CGGGTGCAAT CAACCTTACT GCCGGTACCG CCCTAGTCAA    5580

GCGCGGCAAC ATCAATTGGA GTACCGTTTC GACCAAGACT TTGGAAGATA ATGCCGAATT    5640

AAAACCATTG GCCGGACGGC TGAATATTGA AGCAGGTAGC GGCACATTAA CCATCGAACC    5700

TGCCAACCGC ATCAGTGCGC ATACCGACCT GAGCATCAAA ACAGGCGGAA AATTGCTGTT    5760

GTCTGCAAAA GGAGGAAATG CAGGTGCGCC TAGTGCTCAA GTTTCCTCAT GGAAGCAAA    5820

AGGCAATATC CGTCTGGTTA CAGGAGAAAC AGATTTAAGA GGTTCTAAAA TTACAGCCGG    5880

TAAAAACTTG GTTGTCGCCA CCACCAAAGG CAAGTTGAAT ATCGAAGCCG TAAACAACTC    5940

ATTCAGCAAT TATTTTCCTA CACAAAAAGC GGCTGAACTC AACCAAAAAT CCAAAGAATT    6000

GGAACAGCAG ATTGCGCAGT TGAAAAAAAG CTCGCCTAAA AGCAAGCTGA TTCCAACCCT    6060

GCAAGAAGAA CGCGACCGTC TCGCTTTCTA TATTCAAGCC ATCAACAAGG AAGTTAAAGG    6120

TAAAAAACCC AAAGGCAAAG AATACCTGCA AGCCAAGCTT TCTGCACAAA ATATTGACTT    6180

GATTTCCGCA CAAGGCATCG AAATCAGCGG TTCCGATATT ACCGCTTCCA AAAAACTGAA    6240

CCTTCACGCC GCAGGCGTAT TGCCAAAGGC AGCAGATTCA GAGGCGGCTG CTATTCTGAT    6300

TGACGGCATA ACCGACCAAT ATGAAATTGG CAAGCCCACC TACAAGAGTC ACTACGACAA    6360

AGCTGCTCTG AACAAGCCTT CACGTTTGAC CGGACGTACG GGGGTAAGTA TTCATGCAGC    6420

TGCGGCACTC GATGATGCAC GTATTATTAT CGGTGCATCC GAAATCAAAG CTCCCTCAGG    6480

CAGCATAGAC ATCAAAGCCC ATAGTGATAT TGTACTGGAG GCTGGACAAA ACGATGCCTA    6540

TACCTTCTTA AAAACCAAAG GTAAAAGCGG CAAAATCATC AGAAAAACCA AGTTTACCAG    6600

CACCCGCGAC CACCTGATTA TGCCAGCCCC CGTCGAGCTG ACCGCCAACG GTATCACGCT    6660

TCAGGCAGGC GGCAACATCG AAGCTAATAC CACCCGCTTC AATGCCCCTG CAGGTAAAGT    6720

TACCCTGGTT GCGGGTGAAG AGCTGCAACT GCTGGCAGAA GAAGGCATCC ACAAGCACGA    6780

GTTGGATGTC CAAAAAAGCC GCCGCTTTAT CGGCATCAAG GTAGGTAAGA GCAATTACAG    6840

TAAAAACGAA CTGAACGAAA CCAAATTGCC TGTCCGCGTC GTCGCCCAAA CTGCAGCCAC    6900

CCGTTCAGGC TGGGATACCG TGCTCGAAGG TACCGAATTC AAAACCACGC TGGCCGGTGC    6960

CGACATTCAG GCAGGTGTAG CGAAAAAGC CCGTGTCGAT GCGAAAATTA TCCTCAAAGG     7020

CATTGTGAAC CGTATCCAGT CGGAAGAAAA ATTAGAAACC AACTCAACCG TATGGCAGAA    7080

ACAGGCCGGA CGCGGCAGCA CTATCGAAAC GCTAAAACTG CCCAGCTTCG AAAGCCCTAC    7140

TCCGCCCAAA TTGTCCGCAC CCGGCGGCTA TATCGTCGAC ATTCCGAAAG CAATCTGAA    7200

AACCGAAATC GAAAGCTGTT CCAAACAGCC CGAGTATGCC TATCTGAAAC AGCTCCAAGT    7260

AGCGAAAAAC ATCAACTGGA ATCAGGTGCA GCTTGCTTAC GACAGATGGG ACTACAAACA    7320

GGAGGGCTTA ACCGAAGCAG GTGCGGCGAT TATCGCACTG GCCGTTACCG TGGTCACCTC    7380
```

```
AGGCGCAGGA ACCGGAGCCG TATTGGGATT AAACGGTGCG GCCGCCGCCG CAACCGATGC    7440

AGCATTCGCC TCTTTGGCCA GCCAGGCTTC CGTATCGTTC ATCAACAACA AAGGCGATGT    7500

CGGCAAAACC CTGAAAGAGC TGGGCAGAAG CAGCACGGTG AAAATCTGG TGGTTGCCGC     7560

CGCTACCGCA GGCGTAGCCG ACAAAATCGG CGCTTCGGCA CTGAACAATG TCAGCGATAA    7620

GCAGTGGATC AACAACCTGA CCGTCAACCT AGCCAATGCG GGCAGTGCCG CACTGATTAA    7680

TACCGCTGTC AACGGCGGCA GCCTGAAAGA CAATCTGGAA GCGAATATCC TTGCGGCTTT    7740

GGTCAATACC GCGCATGGAG AAGCAGCCAG TAAAATCAAA CAGTTGGATC AGCACTACAT    7800

AGTCCACAAG ATTGCCCATG CCATAGCGGG CTGTGCGGCA GCGGCGGCGA ATAAGGGCAA    7860

GTGTCAGGAT GGTGCGATAG GTGCGGCTGT GGGCGAGATA GTCGGGGAGG CTTTGACAAA    7920

CGGCAAAAAT CCTGACACTT TGACAGCTAA AGAACGCGAA CAGATTTTGG CATACAGCAA    7980

ACTGGTTGCC GGTACGGTAA GCGGTGTGGT CGGCGGCGAT GTAAATGCGG CGGCGAATGC    8040

GGCTGAGGTA GCGGTGAAAA ATAATCAGCT TAGCGACAAA GAGGGTAGAG AATTTGATAA    8100

CGAAATGACT GCATGCGCCA AACAGAATAA TCCTCAACTG TGCAGAAAAA ATACTGTAAA    8160

AAAGTATCAA AATGTTGCTG ATAAAAGACT TGCTGCTTCG ATTGCAATAT GTACGGATAT    8220

ATCCCGTAGT ACTGAATGTA GAACAATCAG AAAACAACAT TTGATCGATA GTAGAAGCCT    8280

TCATTCATCT TGGGAAGCAG GTCTAATTGG TAAAGATGAT GAATGGTATA AATTATTCAG    8340

CAAATCTTAC ACCCAAGCAG ATTTGGCTTT ACAGTCTTAT CATTTGAATA CTGCTGCTAA    8400

ATCTTGGCTT CAATCGGGCA ATACAAAGCC TTTATCCGAA TGGATGTCCG ACCAAGGTTA    8460

TACACTTATT TCAGGAGTTA ATCCTAGATT CATTCCAATA CCAAGAGGGT TTGTAAAACA    8520

AAATACACCT ATTACTAATG TCAAATACCC GGAAGGCATC AGTTTCGATA CAAACCTAAA    8580

AAGACATCTG GCAAATGCTG ATGGTTTTAG TCAAGAACAG GGCATTAAAG GAGCCCATAA    8640

CCGCACCAAT TTTATGGCAG AACTAAATTC ACGAGGAGGA CGCGTAAAAT CTGAAACCCA    8700

AACTGATATT GAAGGCATTA CCCGAATTAA ATATGAGATT CCTACACTAG ACAGGACAGG    8760

TAAACCTGAT GGTGGATTTA AGGAAATTTC AAGTATAAAA ACTGTTTATA ATCCTAAAAA    8820

ATTTTCTGAT GATAAAATAC TTCAAATGGC TCAAATGCT GCTTCACAAG GATATTCAAA     8880

AGCCTCTAAA ATTGCTCAAA ATGAAAGAAC TAAATCAATA TCGGAAAGAA AAAATGTCAT    8940

TCAATTCTCA GAAACCTTTG ACGGAATCAA ATTTAGATCA TATTTTGATG TAAATACAGG    9000

AAGAATTACA AACATTCACC CAGAATAATT TAAAGGAAAA ATTATGAAAA ATAATATTTT    9060

TCTAAACTTA AATAAAAAAT CTATAAATAA CAACCATTTT GTTATTTCGA TTTTTTTTGA    9120

AACAATTTAC CAATTTGAAA CTAAAGATAC GCTTTTAGAG TGTTTTAAAA ATATTACAAC    9180

TACCGGACAT TTTGGAGTAA TAGGTGCTCA ATATGAAAAA ATAGATGCTA CCAGATGGAT    9240

TGGAGATTAT GAAGAGGTAA ATGGATTTGA GTATATTGAT AAAGCTCCTT CTATTTATTT    9300

TTCAGTTGGA GATGATTTCA ATCCTGAAGA ATTAATTATA CCTATTAATT TAGCATATCA    9360

TTACTTTAAT ATTGCAATAT CTGATTTCTT AATAGCTCAC CCTGAATATC AAAAAAAGTG    9420

TAAAGAAATA CAAAAAACAT ATTCTCAAAC AAACTGTAGC CTGCATGAAA CCTAAAATCC    9480

ATGCGTAAGG TGTGTGCTTC AGCACGCACG CGTTCCATGA TTTACGGCTC AATGCCGTCT    9540

GAAAAGCTCA CAATTTTTCA GACGGCATTT GTTATGCAAG TAAATATTCA GATTCCCTAT    9600

ATACTGCCCA GACGCGTGCG TGCTGAAGAC ACCCCCTACG CTTGCTGCAG AACTTTCGGG    9660

TAAAACCGGT GTGAGCATTA GCGCACCGTA TGCCAATGAG AACAGTCGCA TCCTGCTCAG    9720
```

-continued

| | |
|---|---|
| CACCACGGAT ATCAGTTCGG AAAACGGCAA AATCAAAATT CAATCTTACG GTGACCAATA | 9780 |
| TTACTATGCG AGACAGAGCG AACTCTATAC CTTTGAACGC CGCAGCTACA AAACTGGCAA | 9840 |
| ATGGTACAAC CGCAAACACA TTACCGAAGT CAAAGAACAC AAAAACGCCA AGCCCGACGC | 9900 |
| AGTAAACCTC AGCGCATCCC AAGGCATCGA CATCAAATCT GGTGGCAGCA TCGACGCCTA | 9960 |
| CGCCACCGCA TTCGATGCCC CCAAAGGCAG CATTAACATC GAAGCCGGGC GGAAATTGAC | 10020 |
| ACTCTATGCC GTAGAAGAGC TCAACTACGA CAAACTAGAC AGCCAAAAAA GGCGCAGATT | 10080 |
| TCTCGGCATC AGCTACAGCA AAGCACACGA CACCACCACC CAAGTCATGA AAACCGCGCT | 10140 |
| GCCCTCAAGG GTAGTTGCAG AATCAGCCAA CCTCCAATCG GGCTGGGATA CCAAACTGCA | 10200 |
| AGGCACACAG TTTGAAACCA CACTGGGTGG CGCAACCATA CGCGCAGGCG TAGGTGAGCA | 10260 |
| GGCACGGGCA GATGCCAAGA TTATCCTCGA AGGGATCAAA AGCAGCATCC ACACAGAAAC | 10320 |
| CGTGAGCAGC AGCAAATCTA CTCTATGGCA AAAACAGGCA GGACGGGGCA GTAACATCGA | 10380 |
| AACCTTGCAA TTGCCGAGTT TCACCGGTCC CGTTGCGCCC GTACTGTCCG CACCCGGCGG | 10440 |
| TTACATTGTC GACATTCCGA AAGGCAATCT GAAAACCCAA ATCGAAACCC TCACCAAGCA | 10500 |
| GCCCGAGTAT GCTTATTTGA AACAACTTCA AGTTGCGAAA AACATCAACT GGAATCAGGT | 10560 |
| GCAGCTTGCT TACGATAAAT GGGACTACAA ACAGGAGGGC ATGACACCCG CAGCAGCAGC | 10620 |
| TGTCGTCGTT ATCGTCGTAA CCGTATTGAC CTACGGTGCA CTGTCCGCCC GGCAGCCGC | 10680 |
| CGGAACGGCG GGCGCGGCAG GCGCAGGAGC GGGAGGAGCC GCAGCAGGAA CGGCAGCCGG | 10740 |
| AACTGGAGTA GCAGCAGGAA CGGCAGCCAC AACCGGAGTA GCAGCAGGCA CATCAGCTGC | 10800 |
| AGCTATCACC ACAGCCGCAG GCAAAGCCGC ACTGGCCAGT CTCGCCAGCC AAGCCGCAGT | 10860 |
| TTCCCTCATC AACAACAAAG GAGACATAAA CCATACCCTG AAAGAACTGG GCAAAAGCAG | 10920 |
| CACCGTCAGA CAGGCCGCCA CCGCCGCCGT AACCGCAGGC GTACTGCAGG GCATAAGCGG | 10980 |
| GCTGAACACC CAAGCAGCCG AAGCCGTCAG CAAACATTTT CACAGTCCCG CAGCAGGCAA | 11040 |
| ACTGACCGCT AACCTGATCA ACAGCACCGC TGCCGCAAGT GTCCATACCG CCATCAACGG | 11100 |
| CGGCAGCCTG AAAGACAACT TGGGCGATGC CGCACTGGGT GCGATAGTCA GTACCGTACA | 11160 |
| CGGAGAAGTA GCGAGCAAAA TCAAATTTAA TCTCAGCGAA GACTACATTG CCCACAAGAT | 11220 |
| AGCCCATGCC GTAGCAGGCT GTGCATCGGC GGTAGCAAAT AAAGGCAAAT GTCGGGACGG | 11280 |
| CGCAATCGGC GCGGCAGTCG GCGAGATGGT GGGAGAAACC CTGTTGGACG GACGCGATGT | 11340 |
| AGGCAAACTG TCACCCCAAG AACGCCAAAA AGTCATAGCC TACTCGCAGA TTATCGCAGG | 11400 |
| CAGCGCAGTG GCATTGGTTA AAGGGGATGT GAATACGGCG GTGAATGCGG CTACTGTGGC | 11460 |
| AGTGGAGAAT AATAGTCTTT TAGCTCGCAG GAGGGTAAAT ATACGTTGGA CTCCGCGACA | 11520 |
| AGAATTGGAA CATGAATATG CCATTCTTGA AATCCAGGCC ATTACCAATC AAATCCGAAG | 11580 |
| GCTGGATCCG AAATTTAACG GGATTGCTAT TCTGAGGACT CCTGGAGAGC CGTGGACAAG | 11640 |
| ACATGATGTA CAAACATACA GGCAATATTA TAATCAATTA AGGGAATCCA GAGGCTTTGC | 11700 |
| TGTTGAACCA ATTTATAGAA TCAGGATAAA CAACGGCAAT GAATTTAACC GTATCATGTC | 11760 |
| ATCAAAATAC CCTTATAATG AGCTTTATGT AGCCAATCCT AAATCGGCGA CGGGGTATTT | 11820 |
| TAGGGTAGAT TCGTATGATC CTGCGACAAG GGAAATTATT TCAAGAAAAT TTACCCAATT | 11880 |
| TTCTCAAATC CAAGAAAGTA CGGGGATTGG TTATATCAAG GAGGCTGTTA GAAAATATAG | 11940 |
| CCCTGGTACT GTCATTTCCA ATGTTCCAAG TACACCTACT ACGATAAGAG GAAGAAAGCT | 12000 |
| TGAAGGAAAA CTTATTTTAG AAGTTCCTGC TCAGGTCAAT CCAATTCCAC AATCTGTATT | 12060 |
| AAGGGCGGCA CAAGAAGAAA ATGTTATCAT TAGAGATACA ACAGGAAGGA TTTACAAATG | 12120 |

```
AAGAAAGATA TTTTTTATTG TGAGCAGTGG TCTTATGGTT ATAAGAGACT TCATAAGCCT   12180

TTTTCTGAGA AACAAGCTGA GGAAAAACAT CTTAAAGGGG AGTTATATAC TGCCGTAATA   12240

GGTTCGGCGA CACAACCTGA ATATGTAATT ACCTTGCGAG AGGAAGTAGG TTTTTTTTCG   12300

GTAAATTTTT TCGATAAATT TGGAAGGGAT TATTTAACCC ATCAATTTCA AAAATATTCC   12360

AATTCGAATT ATTATTTTCT TTCTATGGCT GTATGGAGAG ATTATATAAC TTTGAATCT    12420

CATGACTTAG CAGAAGGATA TACTTATTTC TTCAATGAAA ATACGGATGA TTGCTATGTT   12480

TTGAAACAAG ATTTTATTAA TAATGAGCGA TATGAAAAAA CAGAATTATA TTCCCAAAAA   12540

GATAAGGTAA TTCTATTTCC AAAGTTTGGT GAATATGATT TGGTGTTAAA TCCGGACATT   12600

ATTTAATTAA GTTTTAAGGC CGTCTGAAAA AAATTTCAAA CGGCTTTTAT TATTGGGTTT   12660

GGAATCTGAG GATAAAGCTG ATAAAAACCA GGAAATTATC AGATTGCTAT ATACGTATTG   12720

TTGTACAGAC TAAAGGCAGC AATCAAATCA CTATTGCTTA CCCACAAAAA TAAATTGATT   12780

ATATGGAATA ATCATGAATA AGAGAATGAA AATGTGTCCT GCTTGTCAAC AAGGCTATCT   12840

CTACCATTCG AAACCTAAAT ATCTTCATGA TGAAATTATT CTGTGTGATG AATGCGATGC   12900

AGTATGGCTC AAAGGTATGA ATATATTTTA TGGAGAATAT GAAAAGATT TTTATTCTTA    12960

TGTTCCTTTC ATGGAATCCC AAGGTATAAC GAGTGAATGT ATTTGGGAAG GAGATTTGTT   13020

TGATCATCCA TATTATGAAG ATGAAAACTC AAATGATATG GATTGATGGA AATTTTAAGC   13080

CTGCGTAGGT ACGATTAGCC ATCAAACGGC GTAATCATAC GCAAGATTAT CAACAGAGAG   13140

GGCTGGCAGC GATATACCAC CCACAAGATT GCCCATGCCA TAGCGGGCTG TGCGGCAGCG   13200

GCGGCGAATA AGGGCAAGTG TCAGGATGGT GCGATAGGCG CTGCAGTCGG TGAGATTGTT   13260

GGTGAGGCTT TGGTTAAGAA TACTGATTTC AGTCGTATGA GTGCGACCGA AATCGAAAAA   13320

GCTAAAGCGA AGATTACTGC CTATTCAAAA CTGGTTGCCG GCACTGCGTC TGCCGTTGTA   13380

GGCGGGGATG TGAATACAGC GGCGAATGCG GCACAGATAG CGGTGGAGAA TAATACTTTG   13440

TATCCTAGAT GCGTTGGTGC AAAGTGTGAT GAATTTCAAA AGGAACAACA AAAATGGATA   13500

CGTGAAAATC CTGAAGAATA TCGAGAAGTT TTGCTTTTTC AGACAGGATT TATTCCAATT   13560

ATCGGTGATA TACAGAGTTT TGTACAAGCA CAGACCGCTG CCGATCACCT GTTTGCTTTG   13620

CTGGGTGTGG TTCCGGGTAT CGGTGAATCG ATACAGGCCT ATAAAGTAGC GAAAGCGGCA   13680

AAAAATTTAC AAGGCATGAA AAAAGCCTTG GACAAGGCAG CAACCGTTGC CACTGCACAG   13740

GGCTATGTCA GCAAAACCAA AATCAAAATC GGTCAAACTG AATTAAGGGT TACTGCAGCA   13800

ACTGACAAAC AATTGCTGAA AGCTATTGGC GAAGGAAGGG ACACGACAGG TAAAATGACC   13860

GAGCAGTTAT TTGACTCTTT AGCTAAACAA AATGGCTTCA GAGTGCTTTC GGGCGGCAAA   13920

TACGGCGGAA ATAACGGTTT TGATCATGTA TGGCAGGCTG CCGATGGTAG TGTCGTTTTG   13980

ATTGTAGAAA GTAAGCAGAT TAGGAACGGT ACGGTACAGC TGAATCCGAA TGGTGCGGGT   14040

GGATATACGC AAATGAGTGA GGATTGGATT AGACAAGTTT TAGATCAATT ACCCGATGGT   14100

AGTCCCGCTA AAGCTGCTGT CTTCAAAGCA AATAAGAACG GCACATTAAA AACAGCAATA   14160

GCAGGCGTTG ATCGTCAAAC AGGTAAGGCC GTTATTCTTC CTGTCAAAGT TCCTTCTAAA   14220

ACCAATATAA GGAGATAACA ATGGGGCACA ATATGATGAC CACCCAAAAA TGGTATGAGC   14280

ATATTACTAA TGTAATCATA GGCAATACTG CTAATTTCAA TAGCGGTTGC CTTGACTCTA   14340

TAGATTATGT AGATGAAAGA AAAGGCGTTC CGCTTGCAGC TATGCAACAT ATTTTCATGG   14400

ACGTTAGAGC TGCAGCTTCC CATGCCTATC TATTTGAACA TGATCTTAAG AAATTCAAGC   14460
```

```
AATATGCTTA TGTTGCAGGA AAGCTGGGGG TTTTGCTGAG TGTAAATTCT ACAGACCCTG    14520

AACCCTTCTT CTTTCCCTGT GACATGCTCA ACATTCAAAA TCCGATGTTT CTGATGCTGA    14580

TGAGCGACAG CCCACAGCTG CGTGAGTTTC TGGTGCGCAA TATCGACAAC ATCGCCAACG    14640

ATACAGAAGC CTTTATAAAC CGCTACGACC TCAACCGGCA TATGATTTAC AATACTCTGC    14700

TGATGGTGGA GGGTAAGCAG CTTGATCGGT TGAAACAACG TAGCGAGAAA GTCTTGGCGC    14760

ATCCCACCCC TAGCAAATGG CTGCAAAAGC GGTTGTACGA TTACCGCTTC TTCCTCGCTT    14820

TCGCCGAACA GGATGCCGAG GCAATGAAAG CCGCCTTAGA GCCGCTTTTC GATAAAAAAA    14880

CCGCGCGTAT GGCTGCCAAA GAAACATTGT CCTATTTCGA TTTCTACCTG CAGCCGCAAA    14940

TCGTTACCTA CGCCAAAATC GCATCCATGC ACGGTTTCGA TTTGGGCATA GATCAAGAAA    15000

TCTCACCGAG GGATTTGATT GTTTACGATC CGCTGCCGGC AGACGAATAT CAAGACATCT    15060

TCGATTTTAT GAAACAGTAT GACTTGTCTT ACCCGTATGA ATATCTGCAG GATTGGATAG    15120

ATTACTATAC GTTCAAAACC GATAAGCTGG TATTTGGTAA CGCGAAGCGA GAGTGAGCCG    15180

TAAAACTCTG AGCTCCTGTT TTATAGATTA CAACTTTAGG CCGTCTTAAA GCTGAAAGAT    15240

TTTCGAAAGC TATAAATTGA AGCCCTTCCA CAGTACATAG ATCTGTGTTG TGGCGGGGCT    15300

TTACCACGCT GATTGCCGGA GAAGAACTCA ACCTGCTGGC AAAACAAGGC ATGAGATCTT    15360

TGCAATAACA TGAGTTGAGA CCTTTGCAAA AAAGCCCTTC CCCGACATCC GAAACCCAAA    15420

CACAGGATTT CGGCTGTTTT CGTACCAAAT ACCTCCTAAT TTTACCCAAA TACCCCCTTA    15480

ATCCTCCTCG GACACCCGAT AATCAGGCAT CCGGGCTGCC TTTTAGGCGG CAGCGGGCGC    15540

ATTTAGCCTG TTGGCCGCTT TCAACAGGTT CAAACACATC GCCTTCAGGT GGCTTTGCGC    15600

ACTCACTTTG TCATTTCCAA                                                15620

(2) INFORMATION FOR SEQ ID NO: 37:

(i) SEQUENCE CHARACTERISTICS:
        (A) LENGTH: 580 acides amins
        (B) TYPE: amino acid
        (C) STRANDEDNESS: single
        (D) TOPOLOGY: linear (ii) MOLECULE TYPE: peptide (ix) FEATURE:
        (A) NAME/KEY: Protein
        (B) LOCATION:1..580

(xi) SEQUENCE DESCRIPTION: SEQ ID NO: 37:

Met Lys Phe Phe Pro Ala Pro Cys Leu Leu Val Ile Leu Ala Val Ile
1               5                   10                  15

Pro Leu Lys Thr Leu Ala Ala Asp Glu Asn Asp Ala Glu Leu Ile Arg
            20                  25                  30

Ser Met Gln Arg Gln Gln His Ile Asp Ala Glu Leu Leu Thr Asp Ala
        35                  40                  45

Asn Val Arg Phe Glu Gln Pro Leu Glu Lys Asn Asn Tyr Val Leu Ser
    50                  55                  60

Glu Asp Glu Thr Pro Cys Thr Arg Val Asn Tyr Ile Ser Leu Asp Asp
65                  70                  75                  80

Lys Thr Ala Arg Lys Phe Ser Phe Leu Pro Ser Val Leu Met Lys Glu
                85                  90                  95

Thr Ala Phe Lys Thr Gly Met Cys Leu Gly Ser Asn Asn Leu Ser Arg
            100                 105                 110

Leu Gln Lys Ala Ala Gln Gln Ile Leu Ile Val Arg Gly Tyr Leu Thr
```

-continued

```
            115                 120                 125
Ser Gln Ala Ile Ile Gln Pro Gln Asn Met Asp Ser Gly Ile Leu Lys
    130                 135                 140
Leu Arg Val Ser Ala Gly Glu Ile Gly Asp Ile Arg Tyr Glu Glu Lys
145                 150                 155                 160
Arg Asp Gly Lys Ser Ala Glu Gly Ser Ile Ser Ala Phe Asn Asn Lys
                165                 170                 175
Phe Pro Leu Tyr Arg Asn Lys Ile Leu Asn Leu Arg Asp Val Glu Gln
            180                 185                 190
Gly Leu Glu Asn Leu Arg Arg Leu Pro Ser Val Lys Thr Asp Ile Gln
        195                 200                 205
Ile Ile Pro Ser Glu Glu Gly Lys Ser Asp Leu Gln Ile Lys Trp
    210                 215                 220
Gln Gln Asn Lys Pro Ile Arg Phe Ser Ile Gly Ile Asp Asp Ala Gly
225                 230                 235                 240
Gly Lys Thr Thr Gly Lys Tyr Gln Gly Asn Val Ala Leu Ser Phe Asp
                245                 250                 255
Asn Pro Leu Gly Leu Ser Asp Leu Phe Tyr Val Ser Tyr Gly Arg Gly
            260                 265                 270
Leu Val His Lys Thr Asp Leu Thr Asp Ala Thr Gly Thr Glu Thr Glu
        275                 280                 285
Ser Gly Ser Arg Ser Tyr Ser Val His Tyr Ser Val Pro Val Lys Lys
    290                 295                 300
Trp Leu Phe Ser Phe Asn His Asn Gly His Arg Tyr His Glu Ala Thr
305                 310                 315                 320
Glu Gly Tyr Ser Val Asn Tyr Asp Tyr Asn Gly Lys Gln Tyr Gln Ser
                325                 330                 335
Ser Leu Ala Ala Glu Arg Met Leu Trp Arg Asn Arg Phe His Lys Thr
            340                 345                 350
Ser Val Gly Met Lys Leu Trp Thr Arg Gln Thr Tyr Lys Tyr Ile Asp
        355                 360                 365
Asp Ala Glu Ile Glu Val Gln Arg Arg Arg Ser Ala Gly Trp Glu Ala
    370                 375                 380
Glu Leu Arg His Arg Ala Tyr Leu Asn Arg Trp Gln Leu Asp Gly Lys
385                 390                 395                 400
Leu Ser Tyr Lys Arg Gly Thr Gly Met Arg Gln Ser Met Pro Ala Pro
                405                 410                 415
Glu Glu Asn Gly Gly Thr Ile Pro Gly Thr Ser Arg Met Lys Ile
            420                 425                 430
Ile Thr Ala Gly Leu Asp Ala Ala Pro Phe Met Leu Gly Lys Gln
        435                 440                 445
Gln Phe Phe Tyr Ala Thr Ala Ile Gln Ala Gln Trp Asn Lys Thr Pro
    450                 455                 460
Leu Val Ala Gln Asp Lys Leu Ser Ile Gly Ser Arg Tyr Thr Val Arg
465                 470                 475                 480
Gly Phe Asp Gly Glu Gln Ser Leu Phe Gly Glu Arg Gly Phe Tyr Trp
                485                 490                 495
Gln Asn Thr Leu Thr Trp Tyr Phe His Pro Asn His Gln Phe Tyr Leu
            500                 505                 510
Gly Ala Asp Tyr Gly Arg Val Ser Gly Glu Ser Ala Gln Tyr Val Ser
        515                 520                 525
Gly Lys Gln Leu Met Gly Ala Val Val Gly Phe Arg Gly Gly His Lys
    530                 535                 540
```

```
Val Gly Gly Met Phe Ala Tyr Asp Leu Phe Ala Gly Lys Pro Leu His
545                 550                 555                 560

Lys Pro Lys Gly Phe Gln Thr Thr Asn Thr Val Tyr Gly Phe Asn Leu
                565                 570                 575

Asn Tyr Ser Phe
            580

(2) INFORMATION FOR SEQ ID NO: 38:

(i) SEQUENCE CHARACTERISTICS:
        (A) LENGTH: 1981 acides amins
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..1981

(xi) SEQUENCE DESCRIPTION: SEQ ID NO: 38:

Met Asn Lys Gly Leu His Arg Ile Ile Phe Ser Lys Lys His Ser Thr
1               5                  10                  15

Met Val Ala Val Ala Glu Thr Ala Asn Ser Gln Gly Lys Gly Lys Gln
                20                  25                  30

Ala Gly Ser Ser Val Ser Val Ser Leu Lys Thr Ser Gly Asp Leu Cys
                35                  40                  45

Gly Lys Leu Lys Thr Thr Leu Lys Thr Leu Val Cys Ser Leu Val Ser
50                  55                  60

Leu Ser Met Val Leu Pro Ala His Ala Gln Ile Thr Thr Asp Lys Ser
65                  70                  75                  80

Ala Pro Lys Asn Gln Gln Val Val Ile Leu Lys Thr Asn Thr Gly Ala
                85                  90                  95

Pro Leu Val Asn Ile Gln Thr Pro Asn Gly Arg Gly Leu Ser His Asn
                100                 105                 110

Arg Tyr Thr Gln Phe Asp Val Asp Asn Lys Gly Ala Val Leu Asn Asn
                115                 120                 125

Asp Arg Asn Asn Pro Phe Leu Val Lys Gly Ser Ala Gln Leu Ile
130                 135                 140

Leu Asn Glu Val Arg Gly Thr Ala Ser Lys Leu Asn Gly Ile Val Thr
145                 150                 155                 160

Val Gly Gly Gln Lys Ala Asp Val Ile Ile Ala Asn Pro Asn Gly Ile
                165                 170                 175

Thr Val Asn Gly Gly Phe Lys Asn Val Gly Arg Gly Ile Leu Thr
                180                 185                 190

Ile Gly Ala Pro Gln Ile Gly Lys Asp Gly Ala Leu Thr Gly Phe Asp
            195                 200                 205

Val Arg Gln Gly Thr Leu Thr Val Gly Ala Ala Gly Trp Asn Asp Lys
210                 215                 220

Gly Gly Ala Asp Tyr Thr Gly Val Leu Ala Arg Ala Val Ala Leu Gln
225                 230                 235                 240

Gly Lys Leu Gln Gly Lys Asn Leu Ala Val Ser Thr Gly Pro Gln Lys
                245                 250                 255

Val Asp Tyr Ala Ser Gly Glu Ile Ser Ala Gly Thr Ala Ala Gly Thr
                260                 265                 270

Lys Pro Thr Ile Ala Leu Asp Thr Ala Ala Leu Gly Gly Met Tyr Ala
```

-continued

```
                275                 280                 285
Asp Ser Ile Thr Leu Ile Ala Asn Glu Lys Gly Val Gly Val Lys Asn
290                 295                 300
Ala Gly Thr Leu Glu Ala Ala Lys Gln Leu Ile Val Thr Ser Ser Gly
305                 310                 315                 320
Arg Ile Glu Asn Ser Gly Arg Ile Ala Thr Ala Asp Gly Thr Glu
            325                 330                 335
Ala Ser Pro Thr Tyr Leu Ser Ile Glu Thr Thr Lys Gly Ala Ala
                340                 345                 350
Gly Thr Phe Ile Ser Asn Gly Gly Arg Ile Glu Ser Lys Gly Leu Leu
            355                 360                 365
Val Ile Glu Thr Gly Glu Asp Ile Ser Leu Arg Asn Gly Ala Val Val
    370                 375                 380
Gln Asn Asn Gly Ser Arg Pro Ala Thr Thr Val Leu Asn Ala Gly His
385                 390                 395                 400
Asn Leu Val Ile Glu Ser Lys Thr Asn Val Asn Ala Lys Gly Ser
                405                 410                 415
Ala Asn Leu Ser Ala Gly Gly Arg Thr Thr Ile Asn Asp Ala Thr Ile
            420                 425                 430
Gln Ala Gly Ser Ser Val Tyr Ser Ser Thr Lys Gly Asp Thr Glu Leu
            435                 440                 445
Gly Glu Asn Thr Arg Ile Ile Ala Glu Asn Val Thr Val Leu Ser Asn
            450                 455                 460
Gly Ser Ile Gly Ser Ala Ala Val Ile Glu Ala Lys Asp Thr Ala His
465                 470                 475                 480
Ile Glu Ser Gly Lys Pro Leu Ser Leu Glu Thr Ser Thr Val Ala Ser
            485                 490                 495
Asn Ile Arg Leu Asn Asn Gly Asn Ile Lys Gly Gly Lys Gln Leu Ala
            500                 505                 510
Leu Leu Ala Asp Asp Asn Ile Thr Ala Lys Thr Thr Asn Leu Asn Thr
            515                 520                 525
Pro Gly Asn Leu Tyr Val His Thr Gly Lys Asp Leu Asn Leu Asn Val
            530                 535                 540
Asp Lys Asp Leu Ser Ala Ala Ser Ile His Leu Lys Ser Asp Asn Ala
545                 550                 555                 560
Ala His Ile Thr Gly Thr Ser Lys Thr Leu Thr Ala Ser Lys Asp Met
                565                 570                 575
Gly Val Glu Ala Gly Leu Leu Asn Val Thr Asn Thr Asn Leu Arg Thr
            580                 585                 590
Asn Ser Gly Asn Leu His Ile Gln Ala Ala Lys Gly Asn Ile Gln Leu
            595                 600                 605
Arg Asn Thr Lys Leu Asn Ala Ala Lys Ala Leu Glu Thr Thr Ala Leu
            610                 615                 620
Gln Gly Asn Ile Val Ser Asp Gly Leu His Ala Val Ser Ala Asp Gly
625                 630                 635                 640
His Val Ser Leu Leu Ala Asn Gly Asn Ala Asp Phe Thr Gly His Asn
                645                 650                 655
Thr Leu Thr Ala Lys Ala Asp Val Asn Ala Gly Ser Val Gly Lys Gly
            660                 665                 670
Arg Leu Lys Ala Asp Asn Thr Asn Ile Thr Ser Ser Ser Gly Asp Ile
            675                 680                 685
Thr Leu Val Ala Gly Asn Gly Ile Gln Leu Gly Asp Gly Lys Gln Arg
    690                 695                 700
```

```
Asn Ser Ile Asn Gly Lys His Ile Ser Ile Lys Asn Gly Gly Asn
705                 710                 715                 720

Ala Asp Leu Lys Asn Leu Asn Val His Ala Lys Ser Gly Ala Leu Asn
            725                 730                 735

Ile His Ser Asp Arg Ala Leu Ser Ile Glu Asn Thr Lys Leu Glu Ser
            740                 745                 750

Thr His Asn Thr His Leu Asn Ala Gln His Glu Arg Val Thr Leu Asn
            755                 760                 765

Gln Val Asp Ala Tyr Ala His Arg His Leu Ser Ile Thr Gly Ser Gln
770                 775                 780

Ile Trp Gln Asn Asp Lys Leu Pro Ser Ala Asn Lys Leu Val Ala Asn
785                 790                 795                 800

Gly Val Leu Ala Leu Asn Ala Arg Tyr Ser Gln Ile Ala Asp Asn Thr
            805                 810                 815

Thr Leu Arg Ala Gly Ala Ile Asn Leu Thr Ala Gly Thr Ala Leu Val
            820                 825                 830

Lys Arg Gly Asn Ile Asn Trp Ser Thr Val Ser Thr Lys Thr Leu Glu
835                 840                 845

Asp Asn Ala Glu Leu Lys Pro Leu Ala Gly Arg Leu Asn Ile Glu Ala
850                 855                 860

Gly Ser Gly Thr Leu Thr Ile Glu Pro Ala Asn Arg Ile Ser Ala His
865                 870                 875                 880

Thr Asp Leu Ser Ile Lys Thr Gly Gly Lys Leu Leu Leu Ser Ala Lys
            885                 890                 895

Gly Gly Asn Ala Gly Ala Pro Ser Ala Gln Val Ser Ser Leu Glu Ala
            900                 905                 910

Lys Gly Asn Ile Arg Leu Val Thr Gly Glu Thr Asp Leu Arg Gly Ser
            915                 920                 925

Lys Ile Thr Ala Gly Lys Asn Leu Val Val Ala Thr Thr Lys Gly Lys
            930                 935                 940

Leu Asn Ile Glu Ala Val Asn Asn Ser Phe Ser Asn Tyr Phe Pro Thr
945                 950                 955                 960

Gln Lys Ala Ala Glu Leu Asn Gln Lys Ser Lys Glu Leu Glu Gln Gln
            965                 970                 975

Ile Ala Gln Leu Lys Lys Ser Ser Pro Lys Ser Lys Leu Ile Pro Thr
            980                 985                 990

Leu Gln Glu Glu Arg Asp Arg Leu Ala Phe Tyr Ile Gln Ala Ile Asn
            995                 1000                1005

Lys Glu Val Lys Gly Lys Lys Pro Lys Gly Lys Glu Tyr Leu Gln Ala
            1010                1015                1020

Lys Leu Ser Ala Gln Asn Ile Asp Leu Ile Ser Ala Gln Gly Ile Glu
1025                1030                1035                1040

Ile Ser Gly Ser Asp Ile Thr Ala Ser Lys Lys Leu Asn Leu His Ala
            1045                1050                1055

Ala Gly Val Leu Pro Lys Ala Ala Asp Ser Glu Ala Ala Ile Leu
            1060                1065                1070

Ile Asp Gly Ile Thr Asp Gln Tyr Glu Ile Gly Lys Pro Thr Tyr Lys
            1075                1080                1085

Ser His Tyr Asp Lys Ala Ala Leu Asn Lys Pro Ser Arg Leu Thr Gly
            1090                1095                1100

Arg Thr Gly Val Ser Ile His Ala Ala Ala Leu Asp Asp Ala Arg
1105                1110                1115                1120
```

-continued

```
Ile Ile Ile Gly Ala Ser Glu Ile Lys Ala Pro Ser Gly Ser Ile Asp
            1125                1130                1135
Ile Lys Ala His Ser Asp Ile Val Leu Glu Ala Gly Gln Asn Asp Ala
            1140                1145                1150
Tyr Thr Phe Leu Lys Thr Lys Gly Lys Ser Gly Lys Ile Ile Arg Lys
            1155                1160                1165
Thr Lys Phe Thr Ser Thr Arg Asp His Leu Ile Met Pro Ala Pro Val
            1170                1175                1180
Glu Leu Thr Ala Asn Gly Ile Thr Leu Gln Ala Gly Gly Asn Ile Glu
1185                1190                1195                1200
Ala Asn Thr Thr Arg Phe Asn Ala Pro Ala Gly Lys Val Thr Leu Val
            1205                1210                1215
Ala Gly Glu Glu Leu Gln Leu Leu Ala Glu Gly Ile His Lys His
            1220                1225                1230
Glu Leu Asp Val Gln Lys Ser Arg Arg Phe Ile Gly Ile Lys Val Gly
            1235                1240                1245
Lys Ser Asn Tyr Ser Lys Asn Glu Leu Asn Glu Thr Lys Leu Pro Val
            1250                1255                1260
Arg Val Val Ala Gln Thr Ala Ala Thr Arg Ser Gly Trp Asp Thr Val
1265                1270                1275                1280
Leu Glu Gly Thr Glu Phe Lys Thr Thr Leu Ala Gly Ala Asp Ile Gln
            1285                1290                1295
Ala Gly Val Gly Glu Lys Ala Arg Val Asp Ala Lys Ile Ile Leu Lys
            1300                1305                1310
Gly Ile Val Asn Arg Ile Gln Ser Glu Glu Lys Leu Glu Thr Asn Ser
            1315                1320                1325
Thr Val Trp Gln Lys Gln Ala Gly Arg Gly Ser Thr Ile Glu Thr Leu
            1330                1335                1340
Lys Leu Pro Ser Phe Glu Ser Pro Thr Pro Lys Leu Ser Ala Pro
1345                1350                1355                1360
Gly Gly Tyr Ile Val Asp Ile Pro Lys Gly Asn Leu Lys Thr Glu Ile
            1365                1370                1375
Glu Lys Leu Ser Lys Gln Pro Glu Tyr Ala Tyr Leu Lys Gln Leu Gln
            1380                1385                1390
Val Ala Lys Asn Ile Asn Trp Asn Gln Val Gln Leu Ala Tyr Asp Arg
            1395                1400                1405
Trp Asp Tyr Lys Gln Glu Gly Leu Thr Glu Ala Gly Ala Ile Ile
            1410                1415                1420
Ala Leu Ala Val Thr Val Val Thr Ser Gly Ala Gly Thr Gly Ala Val
1425                1430                1435                1440
Leu Gly Leu Asn Gly Ala Ala Ala Ala Thr Asp Ala Ala Phe Ala
            1445                1450                1455
Ser Leu Ala Ser Gln Ala Ser Val Ser Phe Ile Asn Asn Lys Gly Asp
            1460                1465                1470
Val Gly Lys Thr Leu Lys Glu Leu Gly Arg Ser Ser Thr Val Lys Asn
            1475                1480                1485
Leu Val Val Ala Ala Ala Thr Ala Gly Val Ala Asp Lys Ile Gly Ala
            1490                1495                1500
Ser Ala Leu Asn Asn Val Ser Asp Lys Gln Trp Ile Asn Asn Leu Thr
1505                1510                1515                1520
Val Asn Leu Ala Asn Ala Gly Ser Ala Ala Leu Ile Asn Thr Ala Val
            1525                1530                1535
Asn Gly Gly Ser Leu Lys Asp Asn Leu Glu Ala Asn Ile Leu Ala Ala
```

-continued

```
                1540                1545                1550
Leu Val Asn Thr Ala His Gly Glu Ala Ala Ser Lys Ile Lys Gln Leu
            1555                1560                1565
Asp Gln His Tyr Ile Val His Lys Ile Ala His Ala Ile Ala Gly Cys
        1570                1575                1580
Ala Ala Ala Ala Ala Asn Lys Gly Lys Cys Gln Asp Gly Ala Ile Gly
1585                1590                1595                1600
Ala Ala Val Gly Glu Ile Val Gly Glu Ala Leu Thr Asn Gly Lys Asn
            1605                1610                1615
Pro Asp Thr Leu Thr Ala Lys Glu Arg Glu Gln Ile Leu Ala Tyr Ser
        1620                1625                1630
Lys Leu Val Ala Gly Thr Val Ser Gly Val Val Gly Gly Asp Val Asn
            1635                1640                1645
Ala Ala Ala Asn Ala Ala Glu Val Ala Val Lys Asn Asn Gln Leu Ser
        1650                1655                1660
Asp Lys Glu Gly Arg Glu Phe Asp Asn Glu Met Thr Ala Cys Ala Lys
1665                1670                1675                1680
Gln Asn Asn Pro Gln Leu Cys Arg Lys Asn Thr Val Lys Lys Tyr Gln
            1685                1690                1695
Asn Val Ala Asp Lys Arg Leu Ala Ala Ser Ile Ala Ile Cys Thr Asp
        1700                1705                1710
Ile Ser Arg Ser Thr Glu Cys Arg Thr Ile Arg Lys Gln His Leu Ile
            1715                1720                1725
Asp Ser Arg Ser Leu His Ser Ser Trp Glu Ala Gly Leu Ile Gly Lys
        1730                1735                1740
Asp Asp Glu Trp Tyr Lys Leu Phe Ser Lys Ser Tyr Thr Gln Ala Asp
1745                1750                1755                1760
Leu Ala Leu Gln Ser Tyr His Leu Asn Thr Ala Ala Lys Ser Trp Leu
            1765                1770                1775
Gln Ser Gly Asn Thr Lys Pro Leu Ser Glu Trp Met Ser Asp Gln Gly
            1780                1785                1790
Tyr Thr Leu Ile Ser Gly Val Asn Pro Arg Phe Ile Pro Ile Pro Arg
        1795                1800                1805
Gly Phe Val Lys Gln Asn Thr Pro Ile Thr Asn Val Lys Tyr Pro Glu
        1810                1815                1820
Gly Ile Ser Phe Asp Thr Asn Leu Lys Arg His Leu Ala Asn Ala Asp
1825                1830                1835                1840
Gly Phe Ser Gln Glu Gln Gly Ile Lys Gly Ala His Asn Arg Thr Asn
            1845                1850                1855
Phe Met Ala Glu Leu Asn Ser Arg Gly Gly Arg Val Lys Ser Glu Thr
            1860                1865                1870
Gln Thr Asp Ile Glu Gly Ile Thr Arg Ile Lys Tyr Glu Ile Pro Thr
        1875                1880                1885
Leu Asp Arg Thr Gly Lys Pro Asp Gly Gly Phe Lys Glu Ile Ser Ser
        1890                1895                1900
Ile Lys Thr Val Tyr Asn Pro Lys Lys Phe Ser Asp Asp Lys Ile Leu
1905                1910                1915                1920
Gln Met Ala Gln Asn Ala Ala Ser Gln Gly Tyr Ser Lys Ala Ser Lys
            1925                1930                1935
Ile Ala Gln Asn Glu Arg Thr Lys Ser Ile Ser Glu Arg Lys Asn Val
            1940                1945                1950
Ile Gln Phe Ser Glu Thr Phe Asp Gly Ile Lys Phe Arg Ser Tyr Phe
        1955                1960                1965
```

Asp Val Asn Thr Gly Arg Ile Thr Asn Ile His Pro Glu
    1970              1975              1980

(2) INFORMATION FOR SEQ ID NO: 39:

(i) SEQUENCE CHARACTERISTICS:
        (A) LENGTH: 143 acides amins
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..143

(xi) SEQUENCE DESCRIPTION: SEQ ID NO: 39:

Met Lys Asn Asn Ile Phe Leu Asn Leu Asn Lys Lys Ser Ile Asn Asn
1               5                   10                  15

Asn His Phe Val Ile Ser Ile Phe Phe Glu Thr Ile Tyr Gln Phe Glu
            20                  25                  30

Thr Lys Asp Thr Leu Leu Glu Cys Phe Lys Asn Ile Thr Thr Thr Gly
        35                  40                  45

His Phe Gly Val Ile Gly Ala Gln Tyr Glu Lys Ile Asp Ala Thr Arg
    50                  55                  60

Trp Ile Gly Asp Tyr Glu Val Asn Gly Phe Glu Tyr Ile Asp Lys
65              70                  75                  80

Ala Pro Ser Ile Tyr Phe Ser Val Gly Asp Asp Phe Asn Pro Glu Glu
                85                  90                  95

Leu Ile Ile Pro Ile Asn Leu Ala Tyr His Tyr Phe Asn Ile Ala Ile
                100                 105                 110

Ser Asp Phe Leu Ile Ala His Pro Glu Tyr Gln Lys Lys Cys Lys Glu
            115                 120                 125

Ile Gln Lys Thr Tyr Ser Gln Thr Asn Cys Ser Leu His Glu Thr
        130                 135                 140

(2) INFORMATION FOR SEQ ID NO: 40:

(i) SEQUENCE CHARACTERISTICS:
        (A) LENGTH: 833 acides amins
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..833

(xi) SEQUENCE DESCRIPTION: SEQ ID NO: 40:

Val Leu Lys Thr Pro Pro Thr Leu Ala Ala Glu Leu Ser Gly Lys Thr
1               5                   10                  15

Gly Val Ser Ile Ser Ala Pro Tyr Ala Asn Glu Asn Ser Arg Ile Leu
            20                  25                  30

Leu Ser Thr Thr Asp Ile Ser Ser Glu Asn Gly Lys Ile Lys Ile Gln
        35                  40                  45

Ser Tyr Gly Asp Gln Tyr Tyr Tyr Ala Arg Gln Ser Glu Leu Tyr Thr
    50                  55                  60

Phe Glu Arg Arg Ser Tyr Lys Thr Gly Lys Trp Tyr Asn Arg Lys His
65              70                  75                  80

```
Ile Thr Glu Val Lys Glu His Lys Asn Ala Lys Pro Asp Ala Val Asn
                85                  90                  95

Leu Ser Ala Ser Gln Gly Ile Asp Ile Lys Ser Gly Gly Ser Ile Asp
            100                 105                 110

Ala Tyr Ala Thr Ala Phe Asp Ala Pro Lys Gly Ser Ile Asn Ile Glu
        115                 120                 125

Ala Gly Arg Lys Leu Thr Leu Tyr Ala Val Glu Glu Leu Asn Tyr Asp
    130                 135                 140

Lys Leu Asp Ser Gln Lys Arg Arg Phe Leu Gly Ile Ser Tyr Ser
145                 150                 155                 160

Lys Ala His Asp Thr Thr Thr Gln Val Met Lys Thr Ala Leu Pro Ser
                165                 170                 175

Arg Val Val Ala Glu Ser Ala Asn Leu Gln Ser Gly Trp Asp Thr Lys
            180                 185                 190

Leu Gln Gly Thr Gln Phe Glu Thr Thr Leu Gly Gly Ala Thr Ile Arg
        195                 200                 205

Ala Gly Val Gly Glu Gln Ala Arg Ala Asp Ala Lys Ile Ile Leu Glu
    210                 215                 220

Gly Ile Lys Ser Ser Ile His Thr Glu Thr Val Ser Ser Ser Lys Ser
225                 230                 235                 240

Thr Leu Trp Gln Lys Gln Ala Gly Arg Gly Ser Asn Ile Glu Thr Leu
                245                 250                 255

Gln Leu Pro Ser Phe Thr Gly Pro Val Ala Pro Val Leu Ser Ala Pro
            260                 265                 270

Gly Gly Tyr Ile Val Asp Ile Pro Lys Gly Asn Leu Lys Thr Gln Ile
        275                 280                 285

Glu Thr Leu Thr Lys Gln Pro Glu Tyr Ala Tyr Leu Lys Gln Leu Gln
    290                 295                 300

Val Ala Lys Asn Ile Asn Trp Asn Gln Val Gln Leu Ala Tyr Asp Lys
305                 310                 315                 320

Trp Asp Tyr Lys Gln Glu Gly Met Thr Pro Ala Ala Ala Val Val
                325                 330                 335

Val Ile Val Val Thr Val Leu Thr Tyr Gly Ala Leu Ser Ala Pro Ala
            340                 345                 350

Ala Ala Gly Thr Ala Gly Ala Gly Ala Gly Ala Gly Gly Ala Ala
        355                 360                 365

Ala Gly Thr Ala Ala Gly Thr Gly Val Ala Ala Gly Thr Ala Ala Thr
    370                 375                 380

Thr Gly Val Ala Ala Gly Thr Ser Ala Ala Ile Thr Thr Ala Ala
385                 390                 395                 400

Gly Lys Ala Ala Leu Ala Ser Leu Ala Ser Gln Ala Ala Val Ser Leu
                405                 410                 415

Ile Asn Asn Lys Gly Asp Ile Asn His Thr Leu Lys Glu Leu Gly Lys
            420                 425                 430

Ser Ser Thr Val Arg Gln Ala Ala Thr Ala Ala Val Thr Ala Gly Val
        435                 440                 445

Leu Gln Gly Ile Ser Gly Leu Asn Thr Gln Ala Ala Glu Ala Val Ser
    450                 455                 460

Lys His Phe His Ser Pro Ala Ala Gly Lys Leu Thr Ala Asn Leu Ile
465                 470                 475                 480

Asn Ser Thr Ala Ala Ala Ser Val His Thr Ala Ile Asn Gly Gly Ser
                485                 490                 495
```

-continued

```
Leu Lys Asp Asn Leu Gly Asp Ala Ala Leu Gly Ala Ile Val Ser Thr
                500                 505                 510

Val His Gly Glu Val Ala Ser Lys Ile Lys Phe Asn Leu Ser Glu Asp
            515                 520                 525

Tyr Ile Ala His Lys Ile Ala His Ala Val Ala Gly Cys Ala Ser Ala
        530                 535                 540

Val Ala Asn Lys Gly Lys Cys Arg Asp Gly Ala Ile Gly Ala Ala Val
545                 550                 555                 560

Gly Glu Met Val Gly Glu Thr Leu Leu Asp Gly Arg Asp Val Gly Lys
                565                 570                 575

Leu Ser Pro Gln Glu Arg Gln Lys Val Ile Ala Tyr Ser Gln Ile Ile
            580                 585                 590

Ala Gly Ser Ala Val Ala Leu Val Lys Gly Asp Val Asn Thr Ala Val
        595                 600                 605

Asn Ala Ala Thr Val Ala Val Glu Asn Asn Ser Leu Leu Ala Arg Arg
610                 615                 620

Arg Val Asn Ile Arg Trp Thr Pro Arg Gln Glu Leu Glu His Glu Tyr
625                 630                 635                 640

Ala Ile Leu Glu Ile Gln Ala Ile Thr Asn Gln Ile Arg Arg Leu Asp
                645                 650                 655

Pro Lys Phe Asn Gly Ile Ala Ile Leu Arg Thr Pro Gly Glu Pro Trp
            660                 665                 670

Thr Arg His Asp Val Gln Thr Tyr Arg Gln Tyr Tyr Asn Gln Leu Arg
        675                 680                 685

Glu Ser Arg Gly Phe Ala Val Glu Pro Ile Tyr Arg Ile Arg Ile Asn
690                 695                 700

Asn Gly Asn Glu Phe Asn Arg Ile Met Ser Ser Lys Tyr Pro Tyr Asn
705                 710                 715                 720

Glu Leu Tyr Val Ala Asn Pro Lys Ser Ala Thr Gly Tyr Phe Arg Val
                725                 730                 735

Asp Ser Tyr Asp Pro Ala Thr Arg Glu Ile Ile Ser Arg Lys Phe Thr
            740                 745                 750

Gln Phe Ser Gln Ile Gln Glu Ser Thr Gly Ile Gly Tyr Ile Lys Glu
        755                 760                 765

Ala Val Arg Lys Tyr Ser Pro Gly Thr Val Ile Ser Asn Val Pro Ser
770                 775                 780

Thr Pro Thr Thr Ile Arg Gly Arg Lys Leu Glu Gly Lys Leu Ile Leu
785                 790                 795                 800

Glu Val Pro Ala Gln Val Asn Pro Ile Pro Gln Ser Val Leu Arg Ala
                805                 810                 815

Ala Gln Glu Glu Asn Val Ile Ile Arg Asp Thr Thr Gly Arg Ile Tyr
            820                 825                 830

Lys
```

(2) INFORMATION FOR SEQ ID NO: 41:

(i) SEQUENCE CHARACTERISTICS:
        (A) LENGTH: 833 acides amins
        (B) TYPE: amino acid
        (D) TOPOLOGY: linear (ii) MOLECULE TYPE: protein (xi) SEQUENCE DESCRIPTION: SEQ ID NO: 41:

```
Val Leu Lys Thr Pro Pro Thr Leu Ala Ala Glu Leu Ser Gly Lys Thr
  1               5                  10                  15
```

-continued

```
Gly Val Ser Ile Ser Ala Pro Tyr Ala Asn Glu Asn Ser Arg Ile Leu
         20                  25                  30

Leu Ser Thr Thr Asp Ile Ser Ser Glu Asn Gly Lys Ile Lys Ile Gln
     35                  40                  45

Ser Tyr Gly Asp Gln Tyr Tyr Ala Arg Gln Ser Glu Leu Tyr Thr
     50                  55                  60

Phe Glu Arg Arg Ser Tyr Lys Thr Gly Lys Trp Tyr Asn Arg Lys His
 65              70                  75                  80

Ile Thr Glu Val Lys Glu His Lys Asn Ala Lys Pro Asp Ala Val Asn
             85                  90                  95

Leu Ser Ala Ser Gln Gly Ile Asp Ile Lys Ser Gly Gly Ser Ile Asp
100             105                 110

Ala Tyr Ala Thr Ala Phe Asp Ala Pro Lys Gly Ser Ile Asn Ile Glu
 115            120                 125

Ala Gly Arg Lys Leu Thr Leu Tyr Ala Val Glu Glu Leu Asn Tyr Asp
 130            135                 140

Lys Leu Asp Ser Gln Lys Arg Arg Phe Leu Gly Ile Ser Tyr Ser
145             150             155             160

Lys Ala His Asp Thr Thr Thr Gln Val Met Lys Thr Ala Leu Pro Ser
                 165                 170                 175

Arg Val Val Ala Glu Ser Ala Asn Leu Gln Ser Gly Trp Asp Thr Lys
                 180                 185                 190

Leu Gln Gly Thr Gln Phe Glu Thr Thr Leu Gly Gly Ala Thr Ile Arg
         195                 200                 205

Ala Gly Val Gly Glu Gln Ala Arg Ala Asp Ala Lys Ile Ile Leu Glu
     210                 215                 220

Gly Ile Lys Ser Ser Ile His Thr Glu Thr Val Ser Ser Lys Ser
225                 230                 235                 240

Thr Leu Trp Gln Lys Gln Ala Gly Arg Gly Ser Asn Ile Glu Thr Leu
                 245                 250                 255

Gln Leu Pro Ser Phe Thr Gly Pro Val Ala Pro Val Leu Ser Ala Pro
                 260                 265                 270

Gly Gly Tyr Ile Val Asp Ile Pro Lys Gly Asn Leu Lys Thr Gln Ile
             275                 280                 285

Glu Thr Leu Thr Lys Gln Pro Glu Tyr Ala Tyr Leu Lys Gln Leu Gln
         290                 295                 300

Val Ala Lys Asn Ile Asn Trp Asn Gln Val Gln Leu Ala Tyr Asp Lys
305                 310                 315                 320

Trp Asp Tyr Lys Gln Glu Gly Met Thr Pro Ala Ala Ala Val Val
                 325                 330                 335

Val Ile Val Val Thr Val Leu Thr Tyr Gly Ala Leu Ser Ala Pro Ala
                 340                 345                 350

Ala Ala Gly Thr Ala Gly Ala Gly Ala Gly Ala Gly Gly Ala Ala
                 355                 360                 365

Ala Gly Thr Ala Ala Gly Thr Gly Val Ala Ala Gly Thr Ala Ala Thr
     370                 375                 380

Thr Gly Val Ala Ala Gly Thr Ser Ala Ala Ile Thr Thr Ala Ala
385                 390                 395                 400

Gly Lys Ala Ala Leu Ala Ser Leu Ala Ser Gln Ala Ala Val Ser Leu
                 405                 410                 415

Ile Asn Asn Lys Gly Asp Ile Asn His Thr Leu Lys Glu Leu Gly Lys
                 420                 425                 430
```

```
Ser Ser Thr Val Arg Gln Ala Ala Thr Ala Ala Val Thr Ala Gly Val
        435                 440                 445
Leu Gln Gly Ile Ser Gly Leu Asn Thr Gln Ala Ala Glu Ala Val Ser
        450                 455                 460
Lys His Phe His Ser Pro Ala Ala Gly Lys Leu Thr Ala Asn Leu Ile
465                 470                 475                 480
Asn Ser Thr Ala Ala Ser Val His Thr Ala Ile Asn Gly Gly Ser
        485                 490                 495
Leu Lys Asp Asn Leu Gly Asp Ala Ala Leu Gly Ala Ile Val Ser Thr
        500                 505                 510
Val His Gly Glu Val Ala Ser Lys Ile Lys Phe Asn Leu Ser Glu Asp
        515                 520                 525
Tyr Ile Ala His Lys Ile Ala His Ala Val Ala Gly Cys Ala Ser Ala
        530                 535                 540
Val Ala Asn Lys Gly Lys Cys Arg Asp Gly Ala Ile Gly Ala Ala Val
545                 550                 555                 560
Gly Glu Met Val Gly Glu Thr Leu Leu Asp Gly Arg Asp Val Gly Lys
                565                 570                 575
Leu Ser Pro Gln Glu Arg Gln Lys Val Ile Ala Tyr Ser Gln Ile Ile
                580                 585                 590
Ala Gly Ser Ala Val Ala Leu Val Lys Gly Asp Val Asn Thr Ala Val
                595                 600                 605
Asn Ala Ala Thr Val Ala Val Glu Asn Asn Ser Leu Leu Ala Arg Arg
        610                 615                 620
Arg Val Asn Ile Arg Trp Thr Pro Arg Gln Glu Leu Glu His Glu Tyr
625                 630                 635                 640
Ala Ile Leu Glu Ile Gln Ala Ile Thr Asn Gln Ile Arg Arg Leu Asp
                645                 650                 655
Pro Lys Phe Asn Gly Ile Ala Ile Leu Arg Thr Pro Gly Glu Pro Trp
                660                 665                 670
Thr Arg His Asp Val Gln Thr Tyr Arg Gln Tyr Tyr Asn Gln Leu Arg
                675                 680                 685
Glu Ser Arg Gly Phe Ala Val Glu Pro Ile Tyr Arg Ile Arg Ile Asn
        690                 695                 700
Asn Gly Asn Glu Phe Asn Arg Ile Met Ser Ser Lys Tyr Pro Tyr Asn
705                 710                 715                 720
Glu Leu Tyr Val Ala Asn Pro Lys Ser Ala Thr Gly Tyr Phe Arg Val
                725                 730                 735
Asp Ser Tyr Asp Pro Ala Thr Arg Glu Ile Ile Ser Arg Lys Phe Thr
                740                 745                 750
Gln Phe Ser Gln Ile Gln Glu Ser Thr Gly Ile Gly Tyr Ile Lys Glu
                755                 760                 765
Ala Val Arg Lys Tyr Ser Pro Gly Thr Val Ile Ser Asn Val Pro Ser
        770                 775                 780
Thr Pro Thr Thr Ile Arg Gly Arg Lys Leu Glu Gly Lys Leu Ile Leu
785                 790                 795                 800
Glu Val Pro Ala Gln Val Asn Pro Ile Pro Gln Ser Val Leu Arg Ala
                805                 810                 815
Ala Gln Glu Glu Asn Val Ile Ile Arg Asp Thr Thr Gly Arg Ile Tyr
                820                 825                 830
Lys (2) INFORMATION FOR SEQ ID NO: 42:
```

(i) SEQUENCE CHARACTERISTICS:
        (A) LENGTH: 162 acides amins
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..162

(xi) SEQUENCE DESCRIPTION: SEQ ID NO: 42:

Met Lys Lys Asp Ile Phe Tyr Cys Glu Gln Trp Ser Tyr Gly Tyr Lys
1               5                   10                  15

Arg Leu His Lys Pro Phe Ser Glu Lys Gln Ala Glu Glu Lys His Leu
                20                  25                  30

Lys Gly Glu Leu Tyr Thr Ala Val Ile Gly Ser Ala Thr Gln Pro Glu
            35                  40                  45

Tyr Val Ile Thr Leu Arg Glu Val Gly Phe Phe Ser Val Asn Phe
        50                  55                  60

Phe Asp Lys Phe Gly Arg Asp Tyr Leu Thr His Gln Phe Gln Lys Tyr
65                  70                  75                  80

Ser Asn Ser Asn Tyr Tyr Phe Leu Ser Met Ala Val Trp Arg Asp Tyr
                85                  90                  95

Ile Thr Leu Glu Ser His Asp Leu Ala Glu Gly Tyr Thr Tyr Phe Phe
            100                 105                 110

Asn Glu Asn Thr Asp Asp Cys Tyr Val Leu Lys Gln Asp Phe Ile Asn
            115                 120                 125

Asn Glu Arg Tyr Glu Lys Thr Glu Leu Tyr Ser Gln Lys Asp Lys Val
        130                 135                 140

Ile Leu Phe Pro Lys Phe Gly Glu Tyr Asp Leu Val Leu Asn Pro Asp
145                 150                 155                 160

Ile Ile (2) INFORMATION FOR SEQ ID NO: 43:

(i) SEQUENCE CHARACTERISTICS:
        (A) LENGTH: 90 acides amins
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..90

(xi) SEQUENCE DESCRIPTION: SEQ ID NO: 43:

Met Asn Lys Arg Met Lys Met Cys Pro Ala Cys Gln Gln Gly Tyr Leu
1               5                   10                  15

Tyr His Ser Lys Pro Lys Tyr Leu His Asp Glu Ile Ile Leu Cys Asp
                20                  25                  30

Glu Cys Asp Ala Val Trp Leu Lys Gly Met Asn Ile Phe Tyr Gly Glu
            35                  40                  45

Tyr Glu Lys Asp Phe Tyr Ser Tyr Val Pro Phe Met Glu Ser Gln Gly
        50                  55                  60

Ile Thr Ser Glu Cys Ile Trp Glu Gly Asp Leu Phe Asp His Pro Tyr
65                  70                  75                  80

-continued

```
Tyr Glu Asp Glu Asn Ser Asn Asp Met Asp
            85                  90
```

(2) INFORMATION FOR SEQ ID NO: 44:

(i) SEQUENCE CHARACTERISTICS:
        (A) LENGTH: 313 acides amins
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..313

(xi) SEQUENCE DESCRIPTION: SEQ ID NO: 44:

```
Met Ser Ala Thr Glu Ile Glu Lys Ala Lys Ala Lys Ile Thr Ala Tyr
1               5                   10                  15

Ser Lys Leu Val Ala Gly Thr Ala Ser Ala Val Val Gly Gly Asp Val
            20                  25                  30

Asn Thr Ala Ala Asn Ala Ala Gln Ile Ala Val Glu Asn Asn Thr Leu
        35                  40                  45

Tyr Pro Arg Cys Val Gly Ala Lys Cys Asp Glu Phe Gln Lys Glu Gln
    50                  55                  60

Gln Lys Trp Ile Arg Glu Asn Pro Glu Glu Tyr Arg Glu Val Leu Leu
65                  70                  75                  80

Phe Gln Thr Gly Phe Ile Pro Ile Ile Gly Asp Ile Gln Ser Phe Val
                85                  90                  95

Gln Ala Gln Thr Ala Ala Asp His Leu Phe Ala Leu Leu Gly Val Val
            100                 105                 110

Pro Gly Ile Gly Glu Ser Ile Gln Ala Tyr Lys Val Ala Lys Ala Ala
        115                 120                 125

Lys Asn Leu Gln Gly Met Lys Lys Ala Leu Asp Lys Ala Ala Thr Val
    130                 135                 140

Ala Thr Ala Gln Gly Tyr Val Ser Lys Thr Lys Ile Lys Ile Gly Gln
145                 150                 155                 160

Thr Glu Leu Arg Val Thr Ala Ala Thr Asp Lys Gln Leu Leu Lys Ala
                165                 170                 175

Ile Gly Glu Gly Arg Asp Thr Thr Gly Lys Met Thr Glu Gln Leu Phe
            180                 185                 190

Asp Ser Leu Ala Lys Gln Asn Gly Phe Arg Val Leu Ser Gly Gly Lys
        195                 200                 205

Tyr Gly Gly Asn Asn Gly Phe Asp His Val Trp Gln Ala Ala Asp Gly
    210                 215                 220

Ser Val Val Leu Ile Val Glu Ser Lys Gln Ile Arg Asn Gly Thr Val
225                 230                 235                 240

Gln Leu Asn Pro Asn Gly Ala Gly Gly Tyr Thr Gln Met Ser Glu Asp
                245                 250                 255

Trp Ile Arg Gln Val Leu Asp Gln Leu Pro Asp Gly Ser Pro Ala Lys
            260                 265                 270

Ala Ala Val Phe Lys Ala Asn Lys Asn Gly Thr Leu Lys Thr Ala Ile
        275                 280                 285

Ala Gly Val Asp Arg Gln Thr Gly Lys Ala Val Ile Leu Pro Val Lys
    290                 295                 300

Val Pro Ser Lys Thr Asn Ile Arg Arg
305                 310
```

(2) INFORMATION FOR SEQ ID NO: 45:

(i) SEQUENCE CHARACTERISTICS:
        (A) LENGTH: 311 acides amins
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1..311

(xi) SEQUENCE DESCRIPTION: SEQ ID NO: 45:

```
Met Gly His Asn Met Met Thr Thr Gln Lys Trp Tyr Glu His Ile Thr
1               5                   10                  15

Asn Val Ile Ile Gly Asn Thr Ala Asn Phe Asn Ser Gly Cys Leu Asp
            20                  25                  30

Ser Ile Asp Tyr Val Asp Glu Arg Lys Gly Val Pro Leu Ala Ala Met
        35                  40                  45

Gln His Ile Phe Met Asp Val Arg Ala Ala Ser His Ala Tyr Leu
    50                  55                  60

Phe Glu His Asp Leu Lys Lys Phe Lys Gln Tyr Ala Tyr Val Ala Gly
65                  70                  75                  80

Lys Leu Gly Val Leu Leu Ser Val Asn Ser Thr Asp Pro Glu Pro Phe
                85                  90                  95

Phe Phe Pro Cys Asp Met Leu Asn Ile Gln Asn Pro Met Phe Leu Met
            100                 105                 110

Leu Met Ser Asp Ser Pro Gln Leu Arg Glu Phe Leu Val Arg Asn Ile
            115                 120                 125

Asp Asn Ile Ala Asn Asp Thr Glu Ala Phe Ile Asn Arg Tyr Asp Leu
        130                 135                 140

Asn Arg His Met Ile Tyr Asn Thr Leu Leu Met Val Glu Gly Lys Gln
145                 150                 155                 160

Leu Asp Arg Leu Lys Gln Arg Ser Glu Lys Val Leu Ala His Pro Thr
                165                 170                 175

Pro Ser Lys Trp Leu Gln Lys Arg Leu Tyr Asp Tyr Arg Phe Phe Leu
            180                 185                 190

Ala Phe Ala Glu Gln Asp Ala Glu Ala Met Lys Ala Ala Leu Glu Pro
        195                 200                 205

Leu Phe Asp Lys Lys Thr Ala Arg Met Ala Ala Lys Glu Thr Leu Ser
210                 215                 220

Tyr Phe Asp Phe Tyr Leu Gln Pro Gln Ile Val Thr Tyr Ala Lys Ile
225                 230                 235                 240

Ala Ser Met His Gly Phe Asp Leu Gly Ile Asp Gln Glu Ile Ser Pro
                245                 250                 255

Arg Asp Leu Ile Val Tyr Asp Pro Leu Pro Ala Asp Glu Tyr Gln Asp
            260                 265                 270

Ile Phe Asp Phe Met Lys Gln Tyr Asp Leu Ser Tyr Pro Tyr Glu Tyr
        275                 280                 285

Leu Gln Asp Trp Ile Asp Tyr Tyr Thr Phe Lys Thr Asp Lys Leu Val
    290                 295                 300

Phe Gly Asn Ala Lys Arg Glu
305                 310
```

(2) INFORMATION FOR SEQ ID NO: 46:

(i) SEQUENCE CHARACTERISTICS:
        (A) LENGTH: 21 base pairs
        (B) TYPE: nucleotide
        (C) STRANDEDNESS: single
        (D) TOPOLOGY: linear (ii) MOLECULE TYPE: DNA (genomic)

(xi) SEQUENCE DESCRIPTION: SEQ ID NO: 46:

```
GCCACCGGTA CGGAAACTGA A                                        21
```

(2) INFORMATION FOR SEQ ID NO: 47:

(i) SEQUENCE CHARACTERISTICS:
        (A) LENGTH: 30 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 47:

```
CCTGAATTCA TGTCTATTCC ATTTTGAAGA                               30
```

(2) INFORMATION FOR SEQ ID NO: 48:

(i) SEQUENCE CHARACTERISTICS:
        (A) LENGTH: 31 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 48:

```
CCGAGATCTT TAACCCTTTG GGCTTAAGCG A                             31
```

(2) INFORMATION FOR SEQ ID NO: 49:

(i) SEQUENCE CHARACTERISTICS:
        (A) LENGTH: 29 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 49:

```
GGGAGATCTC CCGCTCGTGT TGTGCATTA                                29
```

(2) INFORMATION FOR SEQ ID NO: 50:

(i) SEQUENCE CHARACTERISTICS:
        (A) LENGTH: 28 base pairs
        (B) TYPE: nucleotide
        (C) STRANDEDNESS: single
        (D) TOPOLOGY: linear

```
        (ii) MOLECULE TYPE: DNA (genomic)

(iii) HYPOTHETICAL: NO (iv) ANTI-SENSE: NO (xi) SEQUENCE DESCRIPTION: SEQ ID NO: 50:

AAGAGATCTG CAGCCAAGGC TCTCGAAA                                          28

(2) INFORMATION FOR SEQ ID NO: 51:

(i) SEQUENCE CHARACTERISTICS:
            (A) LENGTH: 26 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 51:

GGGAGATCTC AGGCTGCCGC CGTTGA                                            26

(2) INFORMATION FOR SEQ ID NO: 52:

(i) SEQUENCE CHARACTERISTICS:
            (A) LENGTH: 28 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 52:

GGGAGATCTC ACCCCAAGAA CGCCAAAA                                          28

(2) INFORMATION FOR SEQ ID NO: 53:

(i) SEQUENCE CHARACTERISTICS:
            (A) LENGTH: 31 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 53:

GGGAGATCTG AACGTATAGT AATCTATCCA A                                      31

(2) INFORMATION FOR SEQ ID NO: 54:

(i) SEQUENCE CHARACTERISTICS:
            (A) LENGTH: 12 base pairs
            (B) TYPE: nucleotide
            (C) STRANDEDNESS: single
            (D) TOPOLOGY: linear (ii) MOLECULE TYPE: DNA (genomic)
```

```
        (iii) HYPOTHETICAL: NO (iv) ANTI-SENSE: NO (xi) SEQUENCE DESCRIPTION: SEQ ID NO: 54:

AGTGGCTCCT AG                                                            12

(2) INFORMATION FOR SEQ ID NO: 55:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 55:

AGCACTCTCC AGCCTCTCAC CGAG                                               24

(2) INFORMATION FOR SEQ ID NO: 56:

(i) SEQUENCE CHARACTERISTICS:
        (A) LENGTH: 12 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 56:

AGTGGCTCTT AA                                                            12

(2) INFORMATION FOR SEQ ID NO: 57:

(i) SEQUENCE CHARACTERISTICS:
        (A) LENGTH: 10 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 57:

AGTGGCTGGC                                                               10

(2) INFORMATION FOR SEQ ID NO: 58:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO
```

-continued

```
        (xi) SEQUENCE DESCRIPTION: SEQ ID NO: 58:

AGCACTCTCC AGCCTCTCAC CGAC                                            24

(2) INFORMATION FOR SEQ ID NO: 59:

(i) SEQUENCE CHARACTERISTICS:
            (A) LENGTH: 12 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 59:

GTACTTGCCT AG                                                         12

(2) INFORMATION FOR SEQ ID NO: 60:

(i) SEQUENCE CHARACTERISTICS:
            (A) LENGTH: 24 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 60:

ACCGACGTCG ACTATCCATG AACG                                            24

(2) INFORMATION FOR SEQ ID NO: 61:

(i) SEQUENCE CHARACTERISTICS:
            (A) LENGTH: 12 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 61:

GTACTTGCTT AA                                                         12

(2) INFORMATION FOR SEQ ID NO: 62:

(i) SEQUENCE CHARACTERISTICS:
            (A) LENGTH: 10 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 62:
```

```
GTACTTGGGC                                                                       10

(2) INFORMATION FOR SEQ ID NO: 63:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 63:

ACCGACGTCG ACTATCCATG AACC                                                       24

(2) INFORMATION FOR SEQ ID NO: 64:

(i) SEQUENCE CHARACTERISTICS:
        (A) LENGTH: 12 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 64:

AATTCTCCCT CG                                                                    12

(2) INFORMATION FOR SEQ ID NO: 65:

(i) SEQUENCE CHARACTERISTICS:
        (A) LENGTH: 24 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 65:

AGGCAACTGT GCTATCCGAG GGAG                                                       24

(2) INFORMATION FOR SEQ ID NO: 66:

(i) SEQUENCE CHARACTERISTICS:
        (A) LENGTH: 140 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 66:

GATCAACTTT TCCCTGTTTG TCCCATTACC GGTTTGAATG AACCGATTGC GCGCCGCGCG                60

TGTTGTTGGA CATTACCTGC GATTCAGACG GTACGATTGA CCACTACATC GAGGAGAACG               120
```

GCAATCAGGG TACAATGCTA                                                    140

(2) INFORMATION FOR SEQ ID NO: 67:

(i) SEQUENCE CHARACTERISTICS:
        (A) LENGTH: 192 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 67:

GATCCGCGTA CTTGGTTTTT CATATTTTGC ATAGTCTTGT CGGTCGGGCA TCTTCCCCGA         60

CATCATCTAA ATTTGTCTTT ATTGGTTTTT ACGCCACTCA TTGCGGATAA ACAATATTCC        120

GCCTTGCCGT CGCGAATGTT CAAGCTAGCC TGCATCACCG TAATCAGGTT GCCCGTTACC        180

GAGCCTTCGA GA                                                            192

(2) INFORMATION FOR SEQ ID NO: 68:

(i) SEQUENCE CHARACTERISTICS:
        (A) LENGTH: 188 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 68:

GATCCGGCTG CCCGACGCGC GCAAAATTGC CGCCGAGGAA AGCGCGCACA ACCACGACGG         60

CAAAACCAGC GTATGGCAAT ACAAACATCT CGTGTTCGGT ACGGCAGGCA TTTTCTGCTA        120

TGTCGGCGCG GAGGTGTCTA TCGGTTCGTT GATGGTCAAC GTATTGGGTT ATCTGAAAGG        180

GCTGGATC                                                                 188

(2) INFORMATION FOR SEQ ID NO: 69:

(i) SEQUENCE CHARACTERISTICS:
        (A) LENGTH: 304 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 69:

GATCCCCCAC TTTACCTCGG GCAGATTTTG CGCGTTCATT ACAATAGCGT ATTTATGCGT         60

TTGCGTTTGC GCTTGCCGCT GCCCCCCCCC GCCGGTATG GGAAAACATC AATATGGCGG        120

TATAAAGCGC GGTATGGCGG AAAACCTGCC GTTTCCAAGT TTTATTCATC TTTTATTCCT        180

TGAGTTTGCC TTCACGGGAC GGGGCGGCGC GCGGAACGCG GGGTTCGGTA AACCGCCCGA        240

TTCCGCGCCC GCCGAATTGC TGATTGAAAA GCTTACTTCC CCATTTTAAC TTTGCACACT        300

```
GATC                                                               304

(2) INFORMATION FOR SEQ ID NO: 70:

(i) SEQUENCE CHARACTERISTICS:
        (A) LENGTH: 243 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 70:

GATCAGACCC ATTTTCAGCG CACCGTAAGC GCGGATTTTC TCGAATTTTT CCAAAGCTGC    60

GGCATCGTTG TTGATGTCGT CTTGCAACTC TTTGCCCGTG TAGCCCAAGT CGGCGGCATT   120

CAGGAAAACG GTCGGAATGC CCGCGTTGAT GAGCGTGGCT TTCAAACGGC CTATATTCGG   180

CACATCAATT TCATCGACCA AATTGCCGGT TGGGAACATA CTGCCTTCGC CGTCGGCTGG   240

ATC                                                                243

(2) INFORMATION FOR SEQ ID NO: 71:

(i) SEQUENCE CHARACTERISTICS:
        (A) LENGTH: 236 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 71:

CGGCGGCGTA GTCCGCCGCG ACAGCGTTAC CATAAGCGGG ACAGACTACA CCCCTTTATC    60

TAACCCGCAA AGTTTGGATA CGGAATTAAA ATGGTTGCTT CAAGAAGCTC CCGAAATAGA   120

AAATCCTTTC GACCGCGCCG TTTATCTCCA TAATAATTTG GCGTATCTTC AATATTTTAA   180

AGATTGCAAT AAACGTACTG CCAGAAACTG CATGACCTTG TCGCTGATGC GCTCCG       236

(2) INFORMATION FOR SEQ ID NO: 72:

(i) SEQUENCE CHARACTERISTICS:
        (A) LENGTH: 280 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 72:

CGGTCAATCA CAAGAAAGTC AGCCGTCTGA TGGCGAAGAC GGGGCTGAAG GCAGTGATAT    60

GGCGGCGCAA ATACCGCTCG TTCAAAGGAG AAGTCGGCAA AATTGCGCCG AATATCCTGC   120

GACGCTGTTT CCATGCAGAA AAGCCGAATG AGAAATGGGT AACGGACGTT GCCGAGTTCA   180

ATGTAGGCGG AGAAAAGATA TACCTTTCTC CGATTATGGA TTTGTTTAAC GGGGAAATCG   240
```

```
TCAGTTACCG TATTCAGACC CGCCCGACTT TCGATTTGGC                           280

(2) INFORMATION FOR SEQ ID NO: 73:

(i) SEQUENCE CHARACTERISTICS:
        (A) LENGTH: 120 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 73:

CGGTCAGAAA CAGGCAAGGT AATGAAAATG CCTGAGGCAC GGACTGTGCT GCGAACGAAA    60

ACTCCTTACC GAAGTCTTCT ATACCCAGGC TCAATAGCCG CTCAAGGAGA GAGCTATCAT   120

(2) INFORMATION FOR SEQ ID NO: 74:

(i) SEQUENCE CHARACTERISTICS:
        (A) LENGTH: 120 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 74:

CGGTCAGAAA CAGGCAAGGT AATGAAAATG CCTGAGGCAC GGACTGTGCT GCGAACGAAA    60

ACTCCTTACC GAAGTCTTCT ATACCCAGGC TCAATAGCCG CTCAAGGAGA GAGCTATCAT   120

(2) INFORMATION FOR SEQ ID NO: 75:

(i) SEQUENCE CHARACTERISTICS:
        (A) LENGTH: 152 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 75:

CGGTGTTTTT CTTAACAATT CGCCGACTTC ATGGCGATAT TTAAGTGACA GTTGCTCCGC    60

CCACGCAGTT GCGCCGAACT CAGCACCACG ACATTATACT GATTATGCAC ATCGGCAAGA   120

TCAAACTGAC CTATCGTAGT ATCGCAGACT GT                                 152

(2) INFORMATION FOR SEQ ID NO: 76:

(i) SEQUENCE CHARACTERISTICS:
        (A) LENGTH: 381 base pairs
        (B) TYPE: nucleotide
        (C) STRANDEDNESS: single
        (D) TOPOLOGY: linear (ii) MOLECULE TYPE: DNA (genomic)
```

(iii) HYPOTHETICAL: NO (iv) ANTI-SENSE: NO (xi) SEQUENCE DESCRIPTION: SEQ ID NO: 76:

CGGGAGGTTT TGTGCATCCT GATACCGATC GGTTGTTGTT GCTCAAAGGA CAGAAGGCCG      60

CTGATAAACG AGATTACCTG TTTGTCGCTA TTGACGATTT TTATACTCTG CCATTTTGCC     120

AGACAAAACC GCAGACAGTG CTGCCAAGTT TCTGACCGAA CATCTGGCCG ACCCCTGCTT     180

GTACCTGATT GAGTACGCTT ACTCTGACAA TGATAGGTAA TATAAAGAGC CGTCCAACAT     240

GCTTTCGGTG CAGTTTGTTA TGATAATGGG ATTGGTTGGA GGCTTGCCCG ATTTGCTTGT     300

CCGCAGACCA ACGGTAAGGC GGAGCGGGTT ATCCGTACCT TGATGGAGAT GTGGCATGAG     360

GAACAGTCGT TTGACAGACC G                                               381

(2) INFORMATION FOR SEQ ID NO: 77:

(i) SEQUENCE CHARACTERISTICS:
            (A) LENGTH: 269 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 77:

CGGAGCATAA AATCGTTATT AAAGATAATG GTATAGGAAC GAGCTTCGAT GAAATCAATG      60

ATTTTTATTT GAGAATCGGT CGGAACAGAA GGGAAGAAAA ACAAGCCTCC CCGTGCGGAA     120

GAATTCCAAC GGGTAAAAAA GGCCTTGGTA AATTGGCATT ATTCGGGCTT GGCAACAAAA     180

TTGAAATTTC TACTATCCAG GGAAACGAAA GGGTTACTTT TACTTTGGAT TATGCAGAGA     240

TTCGAAGAAG CAAGGGTATT TATCAACCG                                       269

(2) INFORMATION FOR SEQ ID NO: 78:

(i) SEQUENCE CHARACTERISTICS:
            (A) LENGTH: 203 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 78:

CGGATGAAAA CGGCATACGC GCCAAAGTAT TTACGAACAT CAAAGGCTTG AAGATACCGC      60

ACACCTACAT AGAAACGGAC GCGAAAAAGC TGCCGAAATC GACAGATGAG CAGCTTTCGG     120

CGCATGATAT GTACGAATGG ATAAAGAAGC CCGAAAATAT CGGGTCTATT GTCATTGTAG     180

ATGAAGCTCA AGACGTATGG CCG                                             203

(2) INFORMATION FOR SEQ ID NO: 79:

(i) SEQUENCE CHARACTERISTICS:
            (A) LENGTH: 229 base pairs
            (B) TYPE: nucleotide
            (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 79:

```
CGGTTTCAGG TTGTCGCGAA GGCTCGGTAA CGGGCAACCT GATTACGGGT GATGCAGGCA      60
GCTTGAACAT TCGCGACGGC AAGGCGGAAT ATGTTTATCC GCAATGAGTG GCGTAAAAAC     120
CAATAAAGAC AAATTTAGAT GATGTCGGGG AAGATGCCCG ACCGCAAGA CTATGCAAAA      180
TATGAAAAAC CAAGTACGCG GATCAGGCAT GGATGCACGA TCCAATCCG                 229
```

(2) INFORMATION FOR SEQ ID NO: 80:

(i) SEQUENCE CHARACTERISTICS:
        (A) LENGTH: 207 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 80:

```
CGGGTCGCTT TATTTTGTGC AGGCATTATT TTTCATTTTT GGCTTGACAG TTTGGAAATA      60
TTGTGTATCG GGGGGGGGTA TTTGCTGACG TAAAAAACTA TAAACGCCGC GCAAAATATG     120
GCTGACTATA TTATTGACTT TGATTTTGTC CTGCGCGGTG ATGGATAAAA TCGCCAGCGA     180
TAAAGAATTT GCGAGAACCT GATGCCG                                         207
```

(2) INFORMATION FOR SEQ ID NO: 81 :

(i) SEQUENCE CHARACTERISTICS:
        (A) LENGTH: 224 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 81:

```
CGGCAACGAT TTGAGCTATC GCGGTTACGA CATTCTGGAT TTGGCACAAA AATGCGAGTT      60
TGAAGAAGTC GCCCACCTGC TGATTCACGG CCATCTGCCC AACAAATTCG AGCTGGCCGC     120
TTATAAAACC AAGCTCAAAT CCATGCGCGG CCTGCCTATC CGTGTGATTA AAGTTTTGGA     180
AAGCCTGCCT GCACATACCC ATCCGATGGA CGTAATGCGT ACCG                      224
```

(2) INFORMATION FOR SEQ ID NO: 82:

(i) SEQUENCE CHARACTERISTICS:
        (A) LENGTH: 212 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 82:

CGGGAACAGC CATTGCCCAC GCCCACGCCC CCCAAGAAAG ACGGAAACTA CTGCCTAAAT    60

TTTCGGCAAT CAAGTTGACG ATTAAAGGGT TGGGGGCAGT TGCAGTAATA AACATAGCCG   120

ACGAAATGGG ATTGGAATGA TAGTTGACCA AAGCCAAATA TTTACCCATC TTGCCTTCTG   180

TGCCTTTTGC GGGATTGGAG CCGTAACTGC CG                                 212

(2) INFORMATION FOR SEQ ID NO: 83:

(i) SEQUENCE CHARACTERISTICS:
        (A) LENGTH: 353 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 83:

CGGGAATTCT GAGCAGAATG AAAGAAAGCA GGCTTGATAA TTTCATAAAG TTATTGGAAG    60

AAAAAGGATT TACCGTCCAT TTCGGTATTC ACAATACGGC TGATTACGGA ATTCCCAAA   120

GCCGTAAAAG ATTTACGTTA ATTGCAAACA GAATAACCAA AGAAAGCTG GAACCAGTCA   180

AGTATTCGGG CAAACGGCTT ACGGTAGCCG ATGTTTTGGG AATGGAAATG GCTTTCCCAA   240

CATTATTGCA GGACACCAAG ACGAAACGGA TTTTATGCAT AGCTGTGCGG GAATTATCTG   300

ATATCACTTG AACGATTGGC TTGATACCTA AAAACGGAGG AACCGTTGGC TTT          353

(2) INFORMATION FOR SEQ ID NO: 84:

(i) SEQUENCE CHARACTERISTICS:
        (A) LENGTH: 308 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 84:

AATTCCGTAT CCAAACTTTG CGGGTTAGAT AAAGGGGTGT AGTCTGTCCC GCTTATGGTA    60

ACGCTGTCGC GGCGGACTAC GCCCGGAGCC TTTTTCCAGT AAGTTTTCGG AAATCAGGCT   120

GTGGGTGGTT TTTAAGAAAT CCAACCAGTC AAACGGCTCG GGGCTGTCCA AACCGGACAC   180

AGGTGCCGGT AACTTTCCCT CAGGTTGATT AACATTACGG CATCCGAATA TAACTTCCCG   240

CCTGCGGTTT GCCCGAGTTT AAGCAATGCC TGCGTATCGT ATTGATTATA AAGTGTTTCC   300

TTCCAATT                                                            308

(2) INFORMATION FOR SEQ ID NO: 85:

(i) SEQUENCE CHARACTERISTICS:
        (A) LENGTH: 104 base pairs
        (B) TYPE: nucleotide
        (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 85:

AATTCGTGTG CCGCGTCGAC AAACCGCTGA CGTAGCGGAT GTCTCATGCC ACGTTTCAAA      60

GCAGGTTGAT GGCGGTTAGC AACCCTCTGA TTTCACTGGG ATAT     104

(2) INFORMATION FOR SEQ ID NO: 86:

(i) SEQUENCE CHARACTERISTICS:
        (A) LENGTH: 89 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 86:

AATTGCGTAG AGTGGGCTTC AGCCACGTTT TTTCTTTTTC GGTCGTTGAT TGGTGGGCTG      60

AACCACTTGT TTCGGAAATC CGTATCATG     89

(2) INFORMATION FOR SEQ ID NO: 87:

(i) SEQUENCE CHARACTERISTICS:
        (A) LENGTH: 273 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 87:

AATTTCCACC TATGCCCTAC GCAGCGATTA TCCGTGGTTT ACCCAAAGGG TGATTATGGC      60

AAAAGCGCGG GGTTGAGCGA CCGCCTTTTG TTGCCGGCGT TCAAACGGGT TTTGATAGGA     120

AATGCAGGCA CGAAGCCTCG GCTGATTGTG ATGCACCTGA TGGGTTCGCA CAGTGATTTT     180

TGCACACGTT TGGATAAGGA TGCGCGGCGG TTTCAGTATC AAACTGAAAA AATATCCTGC     240

TATGTTTCCA TCAATCGCGC AAACCGATAA ATT     273

(2) INFORMATION FOR SEQ ID NO: 88:

(i) SEQUENCE CHARACTERISTICS:
        (A) LENGTH: 270 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 88:

| AATTCTTCCG CACGGGGAGG CTTGTTTTTC TTCCCTTCTG TTCCGACCGA TTCTCAAATA | 60 |
| AAAATCATTG ATTTCATCGA AGTTCATTCC TATACCATTA TCTTTAATAA CGATTTTATG | 120 |
| CTCCGGTTTA TCGAATAACC TAACTTCCAC TTCCGTAGCA CATGCATCGT AGGCATTCGC | 180 |
| TATCAACTCG GCAATCGCAG GAACAGTGTG CGAATACAAT CTTTACACCC AAATGTTCGA | 240 |
| TTACGGTTGG CTCGAAACTC AATTTCAATT | 270 |

(2) INFORMATION FOR SEQ ID NO: 89:

(i) SEQUENCE CHARACTERISTICS:
        (A) LENGTH: 267 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 89:

| AATTATGAAC ACACGCATCA TCGTTTCGGC TGCGTTCGTT GCGTTGGCAT TAGCAGGTTG | 60 |
| CGGCTCAATC AATAATGTAA CCGTTTCCGA CCAGAAACTT CAGGAACGTG CCGCGTTTGC | 120 |
| CTTGGGCGTC ACCAATGCCG TAAAAATCAG CAACCGCAGC AATGAAGGCA TACGCATCAA | 180 |
| CTTTACCGCA ACTGTGGGTA AGCGCGTGAC CAATGCTATG TTACCAGTGT AATCAGCACA | 240 |
| ATCGGCGTTA CCACTTCCGA TGCAATT | 267 |

(2) INFORMATION FOR SEQ ID NO: 90:

(i) SEQUENCE CHARACTERISTICS:
        (A) LENGTH: 234 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 90:

| AATTTTTATT TGGTTCGTAG TCATTTGTG CAACTGAACG ATATTCGTTT TCATCATTGC | 60 |
| TAACGTCTAG TGCCCATTGT GGCCCGTAAT AAGAGATTTC GTCTCCTTTT ACATGTTTGA | 120 |
| CGCTGACGGC ATACTGGGGA TCGATGACGG ATAATGTACG TCTGTTGACA TCTGCAACGC | 180 |
| TAAATCAATC ATCGGTATTG GATAATGCGT TGCCGATGTT TTGACTTGTA TGTT | 234 |

(2) INFORMATION FOR SEQ ID NO: 91:

(i) SEQUENCE CHARACTERISTICS:
        (A) LENGTH: 295 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 91:

```
AATTCGGCCG GCTGTGTCAA ATAATGCGTT ACTTTGGCCG GGTCTTGTTC TTTGTAAGTG      60

GTGGTCTTTT TTTGCGCGTT ATCCCCATCT GTTTGAGTGC ATAGCAAATG GTGGCTGCCG     120

TACAATCAAA TGTTTGGCGT TCATGCAGAT AGGCATCATG GTGTTGCCCA ATATATTGAG     180

CCGGTTTTTG CCTATCCGAT TTGACGGCAT TTAGACCGGT AACTTGATGT TTTAAGCTGC     240

CTGTTTGTTT AAAGGCGAAT CCACAAGTAA AGCGTGTTTC TTGACAGGTT AAACG         295

(2) INFORMATION FOR SEQ ID NO: 92:

(i) SEQUENCE CHARACTERISTICS:
        (A) LENGTH: 259 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 92:

AATTGTGTAT ATCAAGTAGG ATGGGCATTT ATGCCTGACC TACAAAACCA AAACAACCT      60

ACCACCCTTA ATCAACTCCA CAAACCCTCT TCAGACAACC TCGTTTTTTG AAAAACAATC    120

TGTAAACAGA TAACTGCTGA AGAATACCGT TGCCAGCCCC AAAACCCGT ACTGCAACTT    180

TTATTGTGAA CTTCCCATTA TGAGAAAATC CCTTTTCGTC CTCTTTCTGT ATTCGTCCCT    240

ACTTACTGCC AGCGAAATT                                                 259

(2) INFORMATION FOR SEQ ID NO: 93:

(i) SEQUENCE CHARACTERISTICS:
        (A) LENGTH: 379 base pairs
        (B) TYPE: nucleotide
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 93:

AATTGCACCA CGCGATGATG GGTACGCCTC TGTTGCCATT GCGACCGCCG CCGCCGTGCC      60

CGGTACGCTG GTCAACCTTG CCGCGGCGGA ACGGGTAAAG AAGTGCGCTT CGGGCATCCT    120

TCCGGTACAT TGCGCGTCGG TGCAGCGCCG AATGTCAGGA CGGACAATGG ACGGCCACCA    180

AAGCGGTTAT GAGCCGCAGC GCACGCGTGA TGATGGAAGG TTGGGTCAGG GTGCCGGAAG    240

ATTGTTTTTA AATTGGACGG CGAACCGGTC TATTCGTATT GGCGTTATAC CGCCGCAAAG    300

GCAGACCTTG AAACTGGTGC GTGCCGTGCA GGGCATGTAC GGCTATGTGT GCGTGGCGGG    360

CGGATTTGAT GTGCGGAAT                                                 379

(2) INFORMATION FOR SEQ ID NO: 94:

(i) SEQUENCE CHARACTERISTICS:
        (A) LENGTH: 308 base pairs
        (B) TYPE: nucleotide
        (C) STRANDEDNESS: single
        (D) TOPOLOGY: linear (ii) MOLECULE TYPE: DNA (genomic)
```

(iii) HYPOTHETICAL: NO (iv) ANTI-SENSE: NO (xi) SEQUENCE DESCRIPTION: SEQ ID NO: 94:

AATTTGTTGG GCAGATGGCC GTGAATCAGC AGGTGGGCGA CTTCTTCAAA CTCGCATTTT      60

TGTGCCAAAT CCAGAATGTC GTAACCGCGA TACGTCAAAT CGTTGCCGGT ACGCAACGGT     120

ACACAAAGCG GTATTACCGG CCGCAACGCC AGAAAGCGCA ACGGATTTTT AGGTTTGAGG     180

GTCGGGGTTT GAGTAGTTTC AGTCATGGTA TTTCTCCTTT GTGTTTTTAT GGGTTTCGGG     240

TTTTCAGACG ACCGATGCGG ATTTGTTGAA AGGCAGTCTG AAAGCGGTAA ATCATTTTTG     300

AAACAATT                                                              308

(2) INFORMATION FOR SEQ ID NO: 95:

(i) SEQUENCE CHARACTERISTICS:
            (A) LENGTH: 286 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 95:

AATTCGGAGG AGCAGTACCG CCAAGCGTTG CTCGCCTATT CCGGCGGTGA TAAAACAGAC      60

GAGGGTATCC GCCTGATGCA ACAGAGCGAT TACGGCAACT TGTCCTACCA CATCCGTAAT     120

AAAAACATGC TTTTCATTTT TTCGGCAAGC AATGACGCAC AAGCTCAGCC CAACACAACT     180

GACCCTATTG CCATTTTATG AAAAAGACGC TCAAAAGGC ATTATCACAG TTGCAGGCGT     240

AGACCGCAGT GGAGAAAAGT TCAATGGCTC CAACCATTGC GGAATT                   286

(2) INFORMATION FOR SEQ ID NO: 96:

(i) SEQUENCE CHARACTERISTICS:
            (A) LENGTH: 238 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 96:

AATTTGGATA CGTTGGAAAA GGGATATTTG ATTGGGAATG GGATGAAGAT AAGCGTAGAT      60

GAGTTGGGGA AAAAGTGTT AGAACATATC GGTAAGAATG AACCGTTATT GTTGAAAAAT     120

CTACTGGTTA ACTTCAATCA GGGAAAACAT GAAGAAGTTA GGAAGTTGAT TTATCAGTTG     180

ATAGAGTTAG ATTTTCTGGA ACTTTTGTGA GGGATTCTAT GAAAAACTGG AAGCAATT      238

(2) INFORMATION FOR SEQ ID NO: 97:

(i) SEQUENCE CHARACTERISTICS:
            (A) LENGTH: 322 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 97:

```
AATTCGGCAC GCAGGTTTTC TAAAAAAAGG CCGTTGATGA CTTTGTCGAT ATTGGCGGCT      60
TCGGTGTAGT GCGCGCCCGC TTCGGCCGCT CTTGCGCGTC CATGACGGAT TGGAAGAGCG     120
TGCCGAAGAT TTCTGGACTG ATGTTGCGCC AGTCGAAATT GCCGACACGG GAGGAATACC     180
TGCCAACAAG AGTGCAGGCA GCGTAATCAA ACCACCCCCA CCCGCAATCG CATCGATAAA     240
TCCGGCAATC ATCGCAACCA AACCCAAAGC GAGTATTATG TATAAATCTT CCATGTTTCT     300
TAATCCTGTT AACTTGCACC AA                                              322
```

(2) INFORMATION FOR SEQ ID NO: 98:

(i) SEQUENCE CHARACTERISTICS:
            (A) LENGTH: 316 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 98:

```
AATTTGTCGG CAATCTTCCC GGGTCGCTTT ATTTTGTGCA GGCATTATTT TTCATTTTTG      60
GCTTGACAGT TTGGAGATAT TGTGTATCGG GGGGGGGTAT TTGCTGACGT AAAAAACTAT     120
AAACGCCGCA GCAAAATATG GCTGACTATA TTATTGACTT TGATTTTGTC CTGCGCGGTG     180
ATGGATAAAA TCGCCAGCGA TAAAGATTTG CGAGAACCTG ATGCCGGCCT GTTGTTGAAT     240
ATTTTCGACC TGTAATTACG ATTTGGCTTC CGCGCCGGCA CAATATGCCG CCAAGCGGCG     300
CCCACATTTT GGAAGC                                                     316
```

(2) INFORMATION FOR SEQ ID NO: 99:

(i) SEQUENCE CHARACTERISTICS:
            (A) LENGTH: 217 base pairs
            (B) TYPE: nucleotide
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO: 99:

```
AATTCGGACA GTATGAATAC AGCGGATTAA TACAAGGTAA GTTCATTACA ACGGAAAAAC      60
CTTTAAAGAA TAATATGAAA GGTATTACCT TGTTTGCCAA CGGGAATGGT AAATATGCCC     120
GAGTTTTTCA CTGAATAGCG AATCCAGCCA TTTCTATTCA TATTTGACTG GATGGCTGAA     180
TGTGGACTTT ATAGATAATG ACGATGAAGA TTTAATT                              217
```